US012680067B2

(12) United States Patent
Zobi et al.

(10) Patent No.: US 12,680,067 B2
(45) Date of Patent: Jul. 14, 2026

(54) METHOD AND DEVICE FOR PROCESSING TISSUES AND CELLS BY ROTATING MICROFLUIDIC CHIPS MOUNTED ON A SUPPORT PLATE

(71) Applicant: Syntr Health Technologies, Inc., Irvine, CA (US)

(72) Inventors: Ahmed Zobi, Cerritos, CA (US); Adrian Bahani, Cerritos, CA (US); Justin Stovner, Cerritos, CA (US); Hugo Salas, Cerritos, CA (US)

(73) Assignee: Syntr Health Technologies, Inc., Irvine, CA (US)

( * ) Notice: Subject to any disclaimer, the term of this patent is extended or adjusted under 35 U.S.C. 154(b) by 707 days.

(21) Appl. No.: 17/924,962

(22) PCT Filed: May 10, 2021

(86) PCT No.: PCT/US2021/031620
§ 371 (c)(1),
(2) Date: Nov. 11, 2022

(87) PCT Pub. No.: WO2021/231321
PCT Pub. Date: Nov. 18, 2021

(65) Prior Publication Data
US 2024/0318117 A1      Sep. 26, 2024

Related U.S. Application Data

(60) Provisional application No. 63/023,060, filed on May 11, 2020.

(51) Int. Cl.
*B04B 5/04*          (2006.01)
*C12M 1/42*          (2006.01)
(Continued)

(52) U.S. Cl.
CPC ........... *C12M 35/04* (2013.01); *B04B 5/0407* (2013.01); *C12M 23/16* (2013.01); *C12M 23/42* (2013.01); *C12M 23/48* (2013.01)

(58) Field of Classification Search
CPC ...... C12M 35/04; C12M 23/16; C12M 23/42; C12M 23/48; A61K 35/28;
(Continued)

(56) References Cited

U.S. PATENT DOCUMENTS 2,928,591 A  *  3/1960  George ................. B01L 3/5021
                                                                209/172
4,883,763 A      11/1989  Holen et al.
(Continued)

FOREIGN PATENT DOCUMENTS

AT            478942 T       9/2010
AT            500319 T       3/2011
(Continued)

OTHER PUBLICATIONS

International Search Report for International Application No. PCT/US2021/031620 dated Aug. 27, 2021.
(Continued)

*Primary Examiner* — Charles Cooley
(74) *Attorney, Agent, or Firm* — Snell & Wilmer LLP

(57)                ABSTRACT

Devices and methods of processing a sample that includes rotating one or more microfluidic chips that are mounted on a support plate. Each microfluidic chip can be rotated 180° on the support plate so that the sample can be run bidirectionally through each of the microfluidic chips. Each of the microfluidic chips can include a fluid path comprising a plurality of expansion and compression regions that increase in radius in more than two dimensions. The support plate
(Continued)

may be configured to reversibly interact with one or more carriage assemblies, which may be operatively coupled to the support plate.

20 Claims, 52 Drawing Sheets

(51) Int. Cl.
  *C12M 3/00* (2006.01)
  *C12M 3/06* (2006.01)

(58) Field of Classification Search
  CPC ... C12N 2527/00; C12N 5/0068; A61P 17/02;
                        B04B 5/00; B04B 5/0421
  USPC ...................................................... 494/16–21
  See application file for complete search history.

(56) References Cited

U.S. PATENT DOCUMENTS

| | | | |
|---|---|---|---|
| 6,527,432 B2 | 3/2003 | Kellogg et al. | |
| 7,074,239 B1 | 7/2006 | Cornwall et al. | |
| 7,090,668 B1 | 8/2006 | U et al. | |
| 7,104,994 B1 | 9/2006 | Amis et al. | |
| 7,390,484 B2 | 6/2008 | Fraser et al. | |
| 7,429,488 B2 | 9/2008 | Fraser et al. | |
| 7,473,420 B2 | 1/2009 | Fraser et al. | |
| 7,501,115 B2 | 3/2009 | Fraser et al. | |
| 7,514,075 B2 | 4/2009 | Hedrick et al. | |
| 7,553,647 B2 | 6/2009 | Yuan et al. | |
| 7,585,670 B2 | 9/2009 | Hedrick et al. | |
| 7,595,043 B2 | 9/2009 | Hedrick et al. | |
| 7,651,684 B2 | 1/2010 | Hedrick et al. | |
| 7,687,059 B2 | 3/2010 | Fraser et al. | |
| 7,771,716 B2 | 8/2010 | Hedrick et al. | |
| 7,819,138 B2 | 10/2010 | Lee et al. | |
| 7,887,795 B2 | 2/2011 | Fraser et al. | |
| 7,901,672 B2 | 3/2011 | Fraser et al. | |
| 8,048,387 B2 | 11/2011 | Lee et al. | |
| 8,101,138 B2 | 1/2012 | Lee et al. | |
| 8,105,580 B2 | 1/2012 | Fraser et al. | |
| 8,119,121 B2 | 2/2012 | Fraser et al. | |
| 8,163,276 B2 | 4/2012 | Hedrick et al. | |
| 8,191,715 B2 | 6/2012 | Cho et al. | |
| 8,246,947 B2 | 8/2012 | Hedrick et al. | |
| 8,337,834 B2 | 12/2012 | Fraser et al. | |
| 8,404,229 B2 | 3/2013 | Fraser et al. | |
| 8,691,216 B2 | 4/2014 | Fraser et al. | |
| 8,771,678 B2 | 7/2014 | Hedrick et al. | |
| 8,784,801 B2 | 7/2014 | Alfonso et al. | |
| 8,883,499 B2 | 11/2014 | Hedrick et al. | |
| 9,101,935 B2 | 8/2015 | Park et al. | |
| 9,162,227 B2 | 10/2015 | Borch | |
| 9,198,937 B2 | 12/2015 | Fraser et al. | |
| 9,213,040 B2 | 12/2015 | Hwang et al. | |
| 9,441,219 B2 | 9/2016 | Williams et al. | |
| 9,442,108 B2 | 9/2016 | Clime et al. | |
| 9,442,109 B2 | 9/2016 | Oosterbroek et al. | |
| 9,463,203 B2 | 10/2016 | Hedrick et al. | |
| 9,480,718 B2 | 11/2016 | Fraser et al. | |
| 9,486,484 B2 | 11/2016 | Alfonso et al. | |
| 9,492,483 B2 | 11/2016 | Fraser et al. | |
| 9,504,716 B2 | 11/2016 | Hedrick et al. | |
| 9,504,718 B2 | 11/2016 | Fraser et al. | |
| 9,511,094 B2 | 12/2016 | Fraser et al. | |
| 9,511,096 B2 | 12/2016 | Fraser et al. | |
| 9,557,316 B2 | 1/2017 | Kim et al. | |
| 9,597,395 B2 | 3/2017 | Fraser et al. | |
| D784,518 S | 4/2017 | Tremolada | |
| 9,631,176 B2 | 4/2017 | Yoshimura et al. | |
| 9,737,889 B2 | 8/2017 | Moon et al. | |
| 9,737,890 B2 | 8/2017 | Lin et al. | |
| 9,808,802 B2 | 11/2017 | Dothie et al. | |
| 9,849,149 B2 | 12/2017 | Fraser et al. | |
| 9,872,877 B2 | 1/2018 | Fraser et al. | |
| 10,058,864 B2 | 8/2018 | Lee et al. | |
| 10,307,757 B2 | 6/2019 | Boehm et al. | |
| 10,589,268 B2 * | 3/2020 | Zobi | B04B 9/10 |
| 11,130,127 B2 * | 9/2021 | Zobi | B04B 5/0407 |
| 12,201,978 B2 * | 1/2025 | Zobi | B04B 5/0407 |
| 2002/0142470 A1 | 10/2002 | Clarke et al. | |
| 2004/0137607 A1 | 7/2004 | Tanaami et al. | |
| 2006/0083667 A1 * | 4/2006 | Kohara | B01L 3/50273 |
| | | | 422/209 |
| 2006/0204556 A1 | 9/2006 | Daniels et al. | |
| 2007/0025876 A1 | 2/2007 | Nishijima et al. | |
| 2007/0224591 A1 | 9/2007 | Gui et al. | |
| 2008/0140451 A1 | 6/2008 | Hedrick et al. | |
| 2009/0075801 A1 | 3/2009 | Hodko et al. | |
| 2009/0304644 A1 | 12/2009 | Hedrick et al. | |
| 2010/0015104 A1 | 1/2010 | Fraser et al. | |
| 2010/0081189 A1 | 4/2010 | Zantl et al. | |
| 2010/0120148 A1 | 5/2010 | Tsuchida | |
| 2010/0136689 A1 | 6/2010 | Tsuchida | |
| 2010/0303774 A1 | 12/2010 | Hedrick et al. | |
| 2010/0317094 A1 | 12/2010 | Ricco et al. | |
| 2010/0330673 A1 | 12/2010 | Fraser et al. | |
| 2011/0003388 A1 | 1/2011 | Fraser et al. | |
| 2011/0045959 A1 | 2/2011 | Kurihara et al. | |
| 2011/0085950 A1 | 4/2011 | Lee et al. | |
| 2011/0158968 A1 | 6/2011 | Fraser et al. | |
| 2011/0177518 A1 | 7/2011 | Kartalov et al. | |
| 2011/0230328 A1 | 9/2011 | Kinoshita et al. | |
| 2011/0294203 A1 | 12/2011 | Tsuchida et al. | |
| 2012/0058093 A1 | 3/2012 | Fraser et al. | |
| 2012/0093783 A1 | 4/2012 | Pinkernell et al. | |
| 2012/0121556 A1 | 5/2012 | Fraser et al. | |
| 2012/0221253 A1 | 8/2012 | Hedrick et al. | |
| 2012/0259289 A1 | 10/2012 | Byrnes et al. | |
| 2012/0264200 A1 | 10/2012 | Hedrick et al. | |
| 2012/0308518 A1 | 12/2012 | Fraser | |
| 2012/0308536 A1 | 12/2012 | Hedrick et al. | |
| 2012/0315257 A1 | 12/2012 | Fraser et al. | |
| 2013/0060338 A1 | 3/2013 | Hedrick et al. | |
| 2013/0108592 A1 | 5/2013 | Pinkernell et al. | |
| 2013/0121974 A1 | 5/2013 | Fraser et al. | |
| 2013/0288290 A1 | 10/2013 | Hedrick et al. | |
| 2013/0344035 A1 | 12/2013 | Fraser et al. | |
| 2014/0227234 A1 | 8/2014 | Fraser et al. | |
| 2014/0227341 A1 | 8/2014 | Fraser et al. | |
| 2014/0369970 A1 | 12/2014 | Alfonso et al. | |
| 2014/0377866 A1 | 12/2014 | Haun et al. | |
| 2015/0023931 A1 | 1/2015 | Hedrick et al. | |
| 2015/0138567 A1 | 5/2015 | Huang et al. | |
| 2015/0152375 A1 | 6/2015 | Hedrick et al. | |
| 2015/0196601 A1 | 7/2015 | Fraser et al. | |
| 2015/0218505 A1 | 8/2015 | Hedrick et al. | |
| 2015/0231244 A1 | 8/2015 | Chi et al. | |
| 2016/0113967 A1 | 4/2016 | Hedrick et al. | |
| 2016/0137970 A1 | 5/2016 | Hedrick et al. | |
| 2016/0143952 A1 | 5/2016 | Fraser et al. | |
| 2016/0177250 A1 | 6/2016 | Arm et al. | |
| 2016/0310540 A1 | 10/2016 | Fraser et al. | |
| 2017/0025930 A1 | 1/2017 | Roswech | |
| 2017/0036208 A1 | 2/2017 | Veres et al. | |
| 2017/0052105 A1 | 2/2017 | Appleyard et al. | |
| 2017/0065638 A1 | 3/2017 | Fraser | |
| 2017/0080422 A1 | 3/2017 | Maaskant et al. | |
| 2017/0114325 A1 | 4/2017 | Alfonso et al. | |
| 2017/0136066 A1 | 5/2017 | Fraser et al. | |
| 2017/0136067 A1 | 5/2017 | Hedrick et al. | |
| 2017/0136069 A1 | 5/2017 | Hedrick et al. | |
| 2017/0173589 A1 | 6/2017 | Clime et al. | |
| 2017/0205322 A1 | 7/2017 | Arm et al. | |
| 2017/0281771 A1 | 10/2017 | Fraser et al. | |
| 2017/0296697 A1 | 10/2017 | Fraser et al. | |
| 2018/0136243 A1 | 5/2018 | Boehm | |
| 2018/0361382 A1 * | 12/2018 | Zobi | B01L 9/527 |
| 2019/0024033 A1 | 1/2019 | Chander et al. | |
| 2019/0091680 A1 | 3/2019 | Lee | |
| 2019/0201900 A1 | 7/2019 | Shachar et al. | |
| 2019/0224675 A1 | 7/2019 | Stahl et al. | |
| 2020/0078411 A1 | 3/2020 | Gimble et al. | |

(56) References Cited

U.S. PATENT DOCUMENTS

| | | | | |
|---|---|---|---|---|
| 2020/0164374 A1* | 5/2020 | Zobi | ........................ | B04B 9/10 |
| 2022/0097050 A1* | 3/2022 | Zobi | ........................ | B04B 9/10 |
| 2024/0318117 A1* | 9/2024 | Zobi | ........................ | A61P 17/02 |

FOREIGN PATENT DOCUMENTS

| AT | 501247 T | 3/2011 |
|---|---|---|
| AT | 524070 T | 9/2011 |
| AU | 2004318008 A | 10/2006 |
| AU | 2010242780 A1 | 12/2011 |
| AU | 2005332046 B2 | 5/2013 |
| AU | 2011254198 B2 | 3/2015 |
| AU | 2014323629 A1 | 5/2016 |
| AU | 2013216683 B2 | 6/2016 |
| CA | 2327789 C | 9/2007 |
| CA | 2760574 A1 | 11/2010 |
| CA | 2799901 A1 | 11/2011 |
| CA | 2924883 A1 | 3/2015 |
| CA | 162188 S | 1/2016 |
| CA | 2963468 A1 | 4/2016 |
| CA | 2572113 C | 4/2017 |
| CA | 2609361 C | 11/2017 |
| CN | 101443023 A | 5/2009 |
| CN | 106434542 A | 1/2010 |
| CN | 201389496 Y | 1/2010 |
| CN | 102458302 A | 5/2012 |
| CN | 102002478 B | 1/2013 |
| CN | 102861105 A | 1/2013 |
| CN | 103038333 A | 4/2013 |
| CN | 104630139 A | 5/2015 |
| CN | 105934155 A | 9/2016 |
| CN | 106834121 A | 6/2017 |
| DK | 1778834 T3 | 11/2010 |
| DK | 1778833 T3 | 6/2011 |
| DK | 1885382 T3 | 6/2011 |
| DK | 1599575 T3 | 1/2012 |
| DK | 1778834 T5 | 1/2012 |
| DK | 1921133 T3 | 8/2015 |
| DK | 1638507 T3 | 6/2017 |
| DK | 1670315 T3 | 8/2017 |
| DK | 2571975 T3 | 10/2017 |
| DK | 3046417 T3 | 10/2017 |
| EP | 2145951 A1 | 1/2010 |
| EP | 2145952 A1 | 1/2010 |
| EP | 1778833 B1 | 3/2011 |
| EP | 1885382 B1 | 3/2011 |
| EP | 2332555 A3 | 6/2011 |
| EP | 2343360 A1 | 7/2011 |
| EP | 2305276 A3 | 9/2011 |
| EP | 2308963 A3 | 9/2011 |
| EP | 2371943 A1 | 10/2011 |
| EP | 1778834 B9 | 11/2011 |
| EP | 1599575 B9 | 3/2012 |
| EP | 2348103 A3 | 7/2012 |
| EP | 2571975 A2 | 3/2013 |
| EP | 1743021 B1 | 3/2014 |
| EP | 1778293 B1 | 4/2015 |
| EP | 1776126 B1 | 5/2015 |
| EP | 1921133 B1 | 5/2015 |
| EP | 2980206 A1 | 2/2016 |
| EP | 2617427 B1 | 8/2016 |
| EP | 3046417 A4 | 9/2016 |
| EP | 3106511 A1 | 12/2016 |
| EP | 2422622 B1 | 1/2017 |
| EP | 1638507 B1 | 3/2017 |
| EP | 1670315 B1 | 4/2017 |
| EP | 2571975 B1 | 7/2017 |
| EP | 3046417 B1 | 7/2017 |
| EP | 2574663 B1 | 8/2017 |
| EP | 2380970 B1 | 12/2017 |
| EP | 3106512 B1 | 3/2018 |
| EP | 3299451 A1 | 3/2018 |
| EP | 2465923 B1 | 4/2018 |
| ES | 2364957 T3 | 9/2011 |
| ES | 2364689 T3 | 2/2012 |
| ES | 2373551 T3 | 2/2012 |
| ES | 2545385 T3 | 9/2015 |
| ES | 2633604 T3 | 9/2017 |
| ES | 2641547 T3 | 11/2017 |
| ES | 2649387 T3 | 1/2018 |
| HK | 1078009 A1 | 6/2011 |
| HK | 1096424 A1 | 2/2013 |
| HK | 1165261 A1 | 8/2015 |
| HR | P 20171471 T1 | 11/2017 |
| JP | 2006110523 A | 4/2006 |
| JP | 2008278821 A | 11/2008 |
| JP | 2008278822 A | 11/2008 |
| JP | 2009075067 A | 4/2009 |
| JP | 2009189280 A | 8/2009 |
| JP | 2009189281 A | 8/2009 |
| JP | 2009189282 A | 8/2009 |
| JP | 2009269930 A | 11/2009 |
| JP | 2010032444 A | 2/2010 |
| JP | 2010043876 A | 2/2010 |
| JP | 2010075066 A | 4/2010 |
| JP | 2010075114 A | 4/2010 |
| JP | 2010095531 A | 4/2010 |
| JP | 2010127620 A | 6/2010 |
| JP | 2010127708 A | 6/2010 |
| JP | 2010148450 A | 7/2010 |
| JP | 2010148451 A | 7/2010 |
| JP | 2011010615 A | 1/2011 |
| JP | 2011010616 A | 1/2011 |
| JP | 2012051923 A | 3/2012 |
| JP | 2012075439 A | 4/2012 |
| JP | 2012149088 A | 8/2012 |
| JP | 2014031389 A | 2/2014 |
| JP | 05960689 B2 | 8/2016 |
| JP | 2016136956 A | 8/2016 |
| JP | 06208787 B2 | 10/2017 |
| JP | 2018030815 A | 3/2018 |
| JP | 2009510481 A | 3/2019 |
| KR | 20050109941 A | 11/2005 |
| KR | 20060025180 A | 3/2006 |
| KR | 20060030861 A | 4/2006 |
| KR | 20070002058 A | 1/2007 |
| KR | 20070017974 A | 2/2007 |
| KR | 20070038538 A | 4/2007 |
| KR | 20070089254 A | 8/2007 |
| KR | 10-779812 B1 | 11/2007 |
| KR | 20080017389 A | 2/2008 |
| KR | 10-811995 B1 | 3/2008 |
| KR | 20080103611 A | 11/2008 |
| KR | 10-0930139 B1 | 12/2009 |
| KR | 20100029272 A | 3/2010 |
| KR | 10-1083454 B1 | 11/2011 |
| KR | 2012003961 A | 1/2012 |
| KR | 20120020143 A | 3/2012 |
| KR | 10-1127305 B1 | 4/2012 |
| KR | 20120038534 A | 4/2012 |
| KR | 10-1145508 B1 | 5/2012 |
| KR | 10-1150666 B1 | 7/2012 |
| KR | 10-1197909 B1 | 11/2012 |
| KR | 20130038412 A | 4/2013 |
| KR | 10-1278437 B1 | 6/2013 |
| KR | 10-1310578 B1 | 9/2013 |
| KR | 10-1400544 B1 | 5/2014 |
| KR | 20160055827 A | 5/2016 |
| KR | 20170115296 A | 10/2017 |
| KR | 20170115377 A | 10/2017 |
| MX | 2011011402 A | 2/2012 |
| MX | 2016003127 A | 10/2016 |
| WO | WO 2003/024215 A1 | 3/2003 |
| WO | WO 2003/053346 A1 | 7/2003 |
| WO | WO 2003/053362 A1 | 7/2003 |
| WO | WO 2005/012480 A1 | 2/2005 |
| WO | WO 2006/014156 A1 | 2/2006 |
| WO | WO 2006/075986 A1 | 7/2006 |
| WO | WO 2006/069349 A9 | 9/2006 |
| WO | WO 2006/039129 A8 | 12/2006 |
| WO | WO 2007/041692 A2 | 4/2007 |
| WO | WO 2007/061530 A1 | 5/2007 |
| WO | WO 2007/139551 A1 | 12/2007 |
| WO | WO 2008/060466 A3 | 8/2008 |

(56)　　　　　References Cited

FOREIGN PATENT DOCUMENTS

| WO | WO 2008/013863 A3 | 10/2008 |
| WO | WO 2008/140044 A8 | 11/2008 |
| WO | WO 2008/140046 A1 | 11/2008 |
| WO | WO 2006/112941 B1 | 12/2008 |
| WO | WO 2006/127007 A3 | 4/2009 |
| WO | WO 2009/055610 A1 | 4/2009 |
| WO | WO 2009/076548 A1 | 6/2009 |
| WO | WO 2009/101910 A1 | 8/2009 |
| WO | WO 2010/021993 A1 | 2/2010 |
| WO | WO 2010/035709 A1 | 4/2010 |
| WO | WO 2010/073808 A1 | 7/2010 |
| WO | WO 2010/124235 A1 | 10/2010 |
| WO | WO 2010/127310 A1 | 11/2010 |
| WO | WO 2011/145075 A2 | 11/2011 |
| WO | WO 2013/075145 A1 | 5/2013 |
| WO | WO 2013/144883 A2 | 10/2013 |
| WO | WO 2013/144883 A3 | 11/2013 |
| WO | WO 2014/016750 A1 | 1/2014 |
| WO | WO 2014/064642 A1 | 5/2014 |
| WO | WO 2014/130391 A1 | 8/2014 |
| WO | WO 2015/042182 A1 | 3/2015 |
| WO | WO 2015/120388 A1 | 8/2015 |
| WO | WO 2015/127126 A1 | 8/2015 |
| WO | WO 2015/140737 A1 | 9/2015 |
| WO | WO 2015/181725 A1 | 12/2015 |
| WO | WO 2016/007434 A1 | 1/2016 |
| WO | WO 2016/054592 A1 | 4/2016 |
| WO | WO 2017/096296 A1 | 6/2017 |
| WO | WO 2017/100328 A1 | 6/2017 |
| WO | WO 2017/115289 A1 | 7/2017 |
| WO | WO 2017/125159 A1 | 7/2017 |
| WO | WO 2017/195156 A1 | 11/2017 |
| WO | WO-2019091650 A1 * | 5/2019 | ............... B04B 9/12 |

OTHER PUBLICATIONS

PCT Written Opinion of the International Search Authority for PCT/US2017/036429, Applicant: The Regents of the University of California, Form PCT/ISA/237, dated Sep. 8, 2017 (12 pages).
PCT International Search Report for PCT/US2017/036429, Applicant: The Regents of the University of California, Form PCT/ISA/210 and 220, dated Sep. 8, 2017 (8 pages).

* cited by examiner

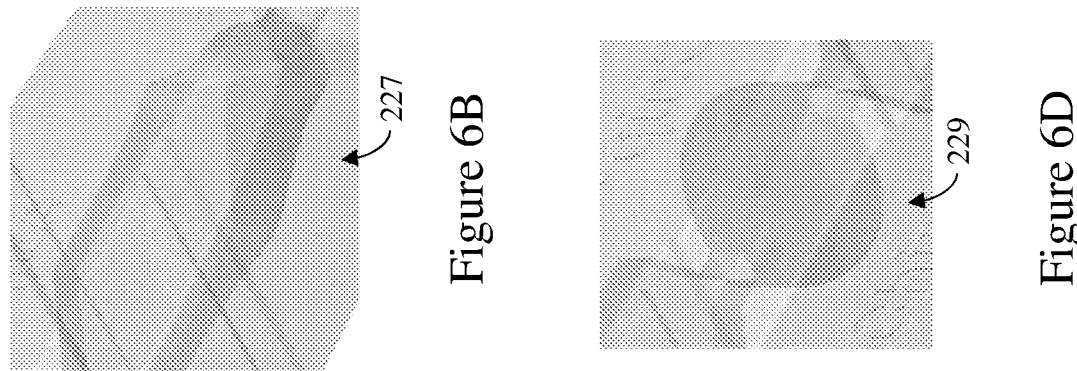
Figure 6B
Figure 6D
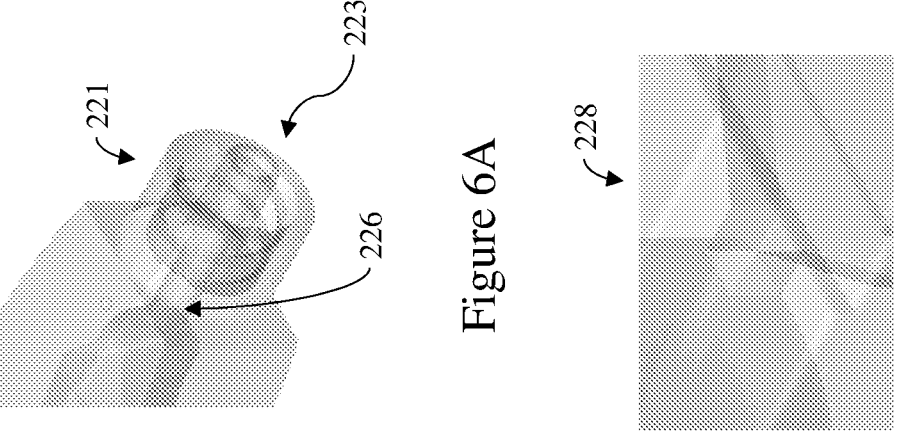
Figure 6A
Figure 6C

METHOD AND DEVICE FOR PROCESSING TISSUES AND CELLS BY ROTATING MICROFLUIDIC CHIPS MOUNTED ON A SUPPORT PLATE

STATEMENT REGARDING FEDERALLY SPONSORED RESEARCH OR DEVELOPMENT

This invention was made with U.S. Government support under Contract No. 1R43DK116389-01, awarded by the National Institutes of Health (NIH) National Institute of Diabetes and Digestive and Kidney Diseases (NIDDK). The US government may have certain rights in this invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

The present application relates generally to devices and methods for applying shear stress to live cells, tissue, reagents, particles, and fluids and uses of the resultant cells in the treatment of damaged tissue. In particular, the technical field relates to utilizing rotational forces in conjunction with microfluidic-based devices for applying shear stress to live cells, and/or tissue, reagents, particles, and fluids. In several embodiments, the methods and device described herein can be used for the treatment of wounds, such as diabetic ulcers, venous stasis ulcers, arterial ulcers, and pressure ulcers (i.e., bedsores). The methods and devices described herein can be used in treatments relating to the following surgical specialties when the transfer of processed and harvested adipose tissue is desired: orthopedic surgery, arthroscopic surgery, neurosurgery, gastrointestinal and affiliated organ surgery, urological surgery, general surgery, gynecological surgery, thoracic surgery, laparoscopic surgery, and plastic and reconstructive surgery when aesthetic body contouring is desired.

BACKGROUND

The diabetic foot ulcer (DFU) is a significant complication of diabetes mellitus (DM) and is the leading cause of nontraumatic lower limb amputations with lower extremity amputations in diabetes occur at a rate of 2 to 1 in men compared to women. The lifetime incidence of DFU formation in individuals suffering DM may be as high as 25%. In 2013, it was estimated that 384 million suffer from DM and this number is expected to climb to 592 million by 2035. The etiology of the DFU is multifactorial and primarily includes some combination of neuropathy, poor vascularity and isolated or repeated trauma. Once a DFU has formed, the wound microenvironment is characterized by poor healing due to continued pressure and/or trauma, chronic infections, and displacement of the plantar fat pad. Current methods for DFU treatment are laden with expense and unpredictable outcomes; however, emerging evidence indicates that autologous stem cell treatment may be a safe and effective alternative to the current treatment options.

A variety of techniques and procedures can be used to process tissue. In some applications, chemicals or enzymes are added to tissue to break-up larger clumps or aggregates of tissue into smaller and smaller pieces. For example, digestive enzymes such as collagenase, trypsin, or dispase are used to digest tissue such as adipose tissue. Such enzymatic processing typically involves washing, followed by enzymatic degradation and centrifugation. This enzymatic approach may suffer from variability due to different activity levels of the digesting enzymes. Moreover, these methods require added costs for reagents including expensive enzymes that are derived from bacteria and take considerable time to complete. As well, the methods may require additional processing and/or washing steps to minimize the effects of enzyme contamination.

Non-enzymatic approaches have also been developed to process tissue, including fat tissue. For example, ultrasonic cavitation has been proposed for the isolation of stromal vascular fraction from adipose tissue. See U.S. Pat. No. 8,440,440, which is incorporated in its entirety by reference herein. Still other methods involve the use of beads to homogenize adipose tissue such as that disclosed in International Patent Publication No. WO2014/036094, which is incorporated in its entirety by reference herein. U.S. Pat. No. 9,580,678 (which is incorporated in its entirety by reference herein) discloses a microfluidic tumor dissociation device that uses a plurality of serially arranged channels or stages with expansion and constriction regions that are used to break-up the tumor tissue. A syringe pump is used to pass tumor tissue back-and-forth through the microfluidic device.

Processing of tissues such as fat tissue has particular importance to the field of plastic and reconstructive surgery where fat tissue is transferred from one location to another to fill soft tissue defects (i.e., fat grafting). Cell-assisted lipotransfer (CAL) is a technique that involves the addition of the stromal vascular fraction (SVF) to fat grafts, and has resulted in significant improvements in fat graft retention. Typically, the SVF is harvested from adipose tissue by a short digestion step using the enzyme collagenase. More recently, a technique called 'nanofat grafting' was developed, whereby standard lipoaspirate is homogenized by manually passing it vigorously between two connected syringes, and then reinjecting the homogenized lipoaspirate in human patients for the correction of superficial rhytides and pigmentation. It was also found that the nanofat processing methods can serve as a means of mechanically dissociating SVF while also stressing the cells to generate multipotent or even pluripotent populations. For example, nanofat-derived SVF is known to have a greater proportion of mesenchymal stem cells (MSCs), adipose derived stem cells (ADSCs), endothelial progenitor cells (EPCs), and Muse cells. It was postulated that the amount of stress that is applied to cells directly correlates with stem-like properties.

MSCs, for example, may be used to treat diabetic ulcers. Current treatments of diabetic foot ulcers, such as allografts, are costly and may not be effective due to the potential rejection by the patient. If such ulcers are left untreated, patients have to undergo limb amputation which, in turn, leads to additional health complications. One innovative solution to treat these ulcers is through the use of MSCs for the direct treatment of these ulcers. However, current approaches of obtaining such cells are lengthy, complicated, and yield variable results in terms of cell yield, quantity and reproducibility. There is a need for quick and cost-effective methods for obtaining processed tissue.

SUMMARY

In view of the need for devices, systems and method for processing tissue in an efficient, effective and reproducible manner, various embodiments of such devices, methods and systems are provided herein, as well as uses for same in developing, producing, or otherwise preparing cells for treating or administering to a subject. Various details about devices to generate activated stem cells as disclosed herein can be found in PCT Patent Publication No. WO 2017/214323 A1, which is incorporated in its entirety by reference herein.

In some embodiments, a system is provided for processing biological samples comprising a support plate. The support plate comprises a central portion configured to reversibly interact with a motor for providing rotational force, and at least one lateral arm, wherein each of the at least one lateral arm includes a first opening and at least one securement opening. The system comprises at least one carriage assembly, wherein the at least one carriage assembly is configured to reversibly interact with one of the at least one lateral arm. The at least one carriage assembly of the system comprises a base, a spring platform, and a securing element. The base of the at least one carriage assembly comprises a top surface comprising at least one circular groove, a bottom surface comprising a post configured to extend through the first opening of one of the at least one lateral arm, a first arm, and a second arm. The spring platform comprises at least one circular groove positioned on a bottom surface of the spring platform, a first engagement portion, and a second engagement portion. The spring platform is positioned adjacent to the top surface of the base. The securing element is configured to secure a chip assembly on the at least one carriage assembly. The at least one carriage assembly can include at least one spring retained between the base and the spring platform, wherein the at least one spring is secured at a first end in the at least one circular groove of the base and at a top end in the at least one circular groove of the spring platform, wherein the at least one spring is configured to provide an upward force on the spring platform. Each of the plurality of carriage assemblies can at least be rotatable about 180 degrees.

In other embodiments, the spring platform can be configured to move between a first position and a second position in response to the insertion or removal of the chip assembly. In other embodiments, the spring platform can further include a tab and the securing element further comprises a channel configured to receive the tab of the spring platform, and wherein the tab is configured to move within the channel of the securing element as the spring platform is configured to move between the first position and the second position. In other embodiments, the securing element include at least one guide rail configured to guide and position the chip assembly. In other embodiments, the first engagement portion of the spring platform is configured to retain the first arm of the base, and wherein the second engagement portion of the spring platform is configured to retain the second arm of the base. In other embodiments the spring platform further comprises a platform configured to guide the chip assembly into the at least one carriage assembly. In other embodiments, the spring platform comprises a splash guard on the bottom surface of the spring platform, the splash guard configured to prevent fluid from being introduced to the at least one spring.

In other embodiments, the chip assembly comprises a microfluidic chip comprising a fluid path that extends from a first end of the microfluidic chip to a second end of the microfluidic chip, a first sample chamber fluidly connected at a first end of the microfluidic chip, and a second sample chamber fluidly connected at a second end of the microfluidic chip. In other embodiments, the fluid path comprises at least one expansion region and a plurality of compression regions. In other embodiments, the at least one expansion region increases in radius along a first, second, and third axis, wherein the first, second, and third axes are perpendicular to a central axis of the fluid path, and wherein the at least one compression region has a diameter less than the diameter of the at least one expansion region, wherein the at least one compressed region does not change in diameter. In other embodiments, the first axis, the second axis, and the third axis are perpendicular to each other. In other embodiments, the at least one expansion region increases in more than two dimensions. In other embodiments, the fluid path comprises a plurality of tear drop expansion regions. In other embodiments, the fluid path comprises a spherical or elliptical expansion region. In other embodiments, the fluid path comprises a plurality of half tear drop expansion regions. In other embodiments, the fluid path comprises a half spherical or half elliptical expansion region. In other embodiments, the fluid path comprises a D-shaped expansion region. In other embodiments, the fluid path comprises an hour-glass. In other embodiments, the fluid path comprises at least two expansion regions and at least one compression region positioned between the at least two expansion regions. In other embodiments, the fluid path comprises at least three expansions regions and at least two compression regions positioned, wherein each of the at least two compression regions is positioned between adjacent expansion regions.

In other embodiments, a filter is positioned between at least one of the microfluidic chip and the first sample chamber or the microfluidic chip and the second sample chamber. In other embodiments, the microfluidic chip of any of the disclosed systems comprises a luer lock on the first end of the microfluidic chip and on the second end of the microfluidic chip.

In some embodiments, a system is provided for processing biological samples comprising a support plate comprising a central portion configured to reversibly interact with a motor for providing rotational force, and at least one lateral arm, wherein each of the at least one lateral arm includes an interacting region. The system can include at least one carriage assembly, wherein the at least one carriage assembly is configured to reversibly interact with one of the at least one lateral arm. In some embodiments, each of the at least one carriage assembly comprises a base, a spring platform positioned above the base, at least one spring retained between the base and the spring platform, wherein the at least one spring is configured to provide an upward force on the spring platform, and a securing element. The system can include at least one chip assembly comprising a microfluidic chip comprising a fluid path that extends from a first end of the microfluidic chip to a second end of the microfluidic chip. The fluid path can include at least one expansion region and at least one compression region. The at least one expansion region can increases in diameter along a first, second, and third axis, wherein the first, second, and third axes are perpendicular to a central axis of the fluid path. The at least one compression region can have a diameter less than the diameter of the at least one expansion region, wherein the at least one compressed region does not change in diameter. The chip assembly can include a first sample chamber fluidly connected at a first end of the microfluidic chip and a second sample chamber fluidly connected at a second end of the microfluidic chip. The at least one chip assembly can be received within the at least one carriage assembly, and each of the at least one carriage assemblies is at least rotatable about 180 degrees.

In other embodiments, the first axis, the second axis, and the third axis are perpendicular to each other. In other embodiments, the at least one expansion region increases in more than two dimensions. In other embodiments, the fluid path comprises a plurality of tear drop expansion regions. In other embodiments, the fluid path comprises a spherical or elliptical expansion region. In other embodiments, the fluid path comprises a plurality of half tear drop expansion regions. In other embodiments, the fluid path comprises a half spherical or half elliptical expansion region. In other embodiments, the fluid path comprises a D-shaped expansion region. In other embodiments, the fluid path comprises an hour-glass. In other embodiments, the fluid path comprises at least two expansion regions and at least one compression region positioned between the at least two expansion regions. In other embodiments, the fluid path comprises at least three expansions regions and at least two compression regions positioned, wherein each of the at least two compression regions is positioned between adjacent expansion regions. In other embodiments, a filter is positioned between at least one of the microfluidic chip and the first sample chamber or the microfluidic chip and the second sample chamber. In other embodiments, the microfluidic chip comprises a luer lock on the first end of the microfluidic chip and on the second end of the microfluidic chip.

In some embodiments, a system is provided processing biological samples. The system can include a support plate comprising a central portion configured to reversibly interact with a motor for providing rotational force, and a plurality of lateral arms, wherein each of the plurality of lateral arms includes an interacting region. The support plate can include a plurality of holding arms, wherein each of the plurality of holding arms are positioned between each of the plurality of lateral arms, wherein each of the plurality of holding arms are configured to retain a syringe. The system can include at least one carriage assembly, wherein the at least one carriage assembly is configured to reversibly interact with one of the at least one lateral arm and the at least one chip assembly is received within the carriage assembly. In some embodiments, each of the at least one carriage assemblies is at least rotatable about 180 degrees.

In some embodiments, a method of treating damaged tissue is disclosed. The method can include administering to a subject having a damaged or diseased tissue a population of activated adipose stem cells in an amount ranging between about $1\times10^4$ and $1\times10^{10}$ cells per g. The activated adipose stem cells can lead to one or more of an upregulation of regenerative phenotypes (e.g., CD34, CD13, CD73, CD146), reduction of inflammation, quicker tissue growth, quicker tissue remodeling, increased vascularization or combinations thereof.

In other embodiments, the administration of the method is by subcutaneous injection. In other embodiments the administration of the method is by intravenous injection. In other embodiments, the damaged tissue is the result of an ulcer. In other embodiments, the ulcer is selected from the group consisting of diabetic foot ulcer, pressure ulcer (i.e., bed sores), venous stasis ulcers, and arterial ulcers. In other embodiments, the damaged tissue is the result of a wound. In other embodiments, the wound is a burn-related wound, an abrasion (e.g., road rash), a laceration (e.g., a wound sustained from a knife), a puncture wound, or an avulsion (e.g., a bullet wound or a wound sustained from other weapons). In other embodiments, the administration results in at least a 10% reduction in the time for the damaged tissue to heal, as compared to damaged tissue not exposed to the activated adipose stem cells. In other embodiments, the administration results in at least a 50% reduction in the time for the damaged tissue to heal, as compared to damaged tissue not exposed to the activated adipose stem cells.

In some embodiments, a method of treating damaged tissue is disclosed. The method can include administering to a subject having a damaged or diseased tissue a population of activated adipose stem cells in an amount sufficient to increase vascularization at the site of damage.

In some embodiments, use of a population of activated adipose stem cells for the treatment of damaged tissue, wherein the population of activated adipose stem cells is provided in an amount ranging between about $1\times10^4$ and $1\times10^{10}$ cells per g of a subject having damaged tissue, and wherein exposure of the damaged tissue to the activated adipose stem cells results in at least a 10% reduction in the time for the damaged tissue to heal, as compared to damaged tissue not exposed to the activated adipose stem cells.

In other embodiments, the activated adipose stem cells lead to one or more of an upregulation of regenerative phenotypes (e.g., CD34, CD13, CD73, CD146), reduction of inflammation, quicker tissue growth, quicker tissue remodeling, increased vascularization, or combinations thereof. In other embodiments, the administration results in at least a 50% reduction in the time for the damaged tissue to heal, as compared to damaged tissue not exposed to the activated adipose stem cells.

In some embodiments, a method of activating adipose stem cells for use in tissue repair is disclosed. The method can include extracting a sample of adipose tissue from a patient in an amount sufficient to create a sufficient amount of a mechanically processed adipose-derived stem cells. The method can include inserting the sample of adipose tissue into a first sample chamber that is located at one end of a microfluidic chip. The method can include using a motor driven rotational chuck to rotate the microfluidic chip to subject the sample of adipose tissue to shear forces. In the method disclosed, while the microfluidic chip is rotating, the sample of adipose tissue is travelling back-and-forth along a plurality of microfluidic channels from the first sample chamber to a second sample chamber that is located at an opposing end of the microfluidic chip. The method can include removing the mechanically processed adipose-derived stem cells from the microfluidic chip. The method can include administering to the patient the mechanically processed adipose-derived stem cells at the site of damage.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIGS. 6A-6D illustrate enlarged view of the microfluidic chip of FIGS. 5A-5C configured to be secured in the chip assembly of FIGS. 4A-4B.

FIG. 30A shows the degree of CD26+/CD55+ cells derived from adipose samples from healthy and diabetic patients. FIG. 30B shows the degree of CD34+ cells derived from adipose samples from healthy and diabetic patients.

FIG. 31A shows the cell density resulting from processing of adipose samples from healthy and diabetic patients. FIG. 31B shows the cell viability resulting from processing of adipose samples from healthy and diabetic patients.

FIG. 32A shows the percentage of endothelial progenitor cells (EPC) in a cell population derived from processing of adipose samples from healthy and diabetic patients. FIG. 32B shows the percentage of mesenchymal stem cells (MSC) in a cell population derived from processing of adipose samples from healthy and diabetic patients. FIG. 32C shows the percentage of Muse cells in a cell population derived from processing of adipose samples from healthy and diabetic patients.

FIG. 33A shows the cell viability for cells derived from adipose samples under the indicated conditions. FIG. 33B shows the cell counts for cells derived from adipose samples under the indicated conditions. FIG. 33C shows the subpopulations of types of cells derived from adipose samples under the indicated conditions.

FIG. 34A shows histology data related to the presence of certain markers and tissue regeneration. FIG. 34B shows photographs of wound healing progression over time in a mouse injury model. FIG. 34C provides summary data of wound healing for the indicated groups.

DETAILED DESCRIPTION

Figure 1:
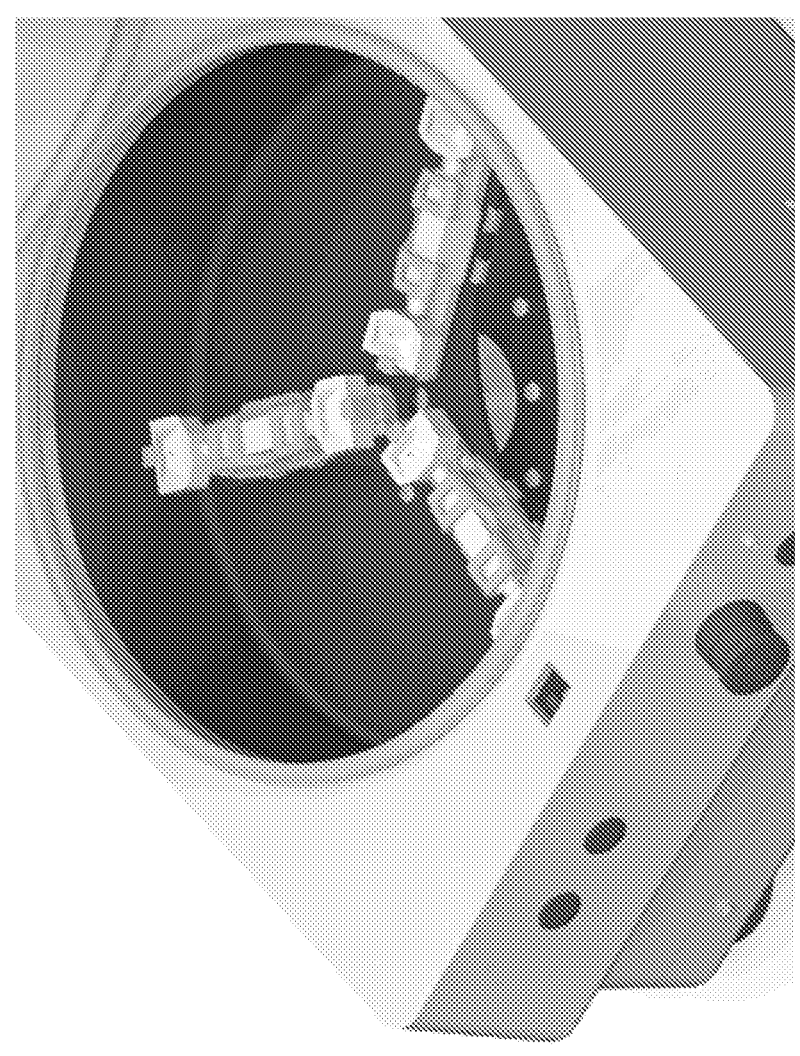
FIG. 1 illustrates an embodiment of a system for processing biological samples

Although certain examples are described below, those of skill in the art will appreciate that the disclosure extends beyond the specifically disclosed examples and/or uses and obvious modifications and equivalents thereof. Thus, it is intended that the scope of the disclosure herein disclosed should not be limited by any particular examples described below.

In several embodiments, there is provided a system for processing biological samples comprising a support plate comprising a central portion comprising a receiving element, a lateral portion comprising a plurality of interacting regions, each configured to reversibly interact with a plurality of carriages, a plurality of carriages, wherein each of the plurality of carriages is configured to be operatively coupled to the lateral portion of the support plate.

In several embodiments, the receiving element is configured to reversibly interact with a drive shaft of a motor, the motor configured to apply centrifugal movement to the support plate. In one embodiment, the central portion lies in a plane perpendicular to an axis of rotation of the drive shaft of the motor and the lateral portion extends radially from the central portion and at least partially lies within a plane parallel to the plane of the central portion.

In several embodiments, each of the plurality of carriages comprises a first end and a second end and a base portion extending between the first and second ends, and a receiving region configured to reversibly interact with a microfluidic chip that is fluidically coupled to at least one sample chamber configured to receive a sample for processing. In several embodiments, each of the plurality of carriages comprises a post, rod, shaft, or other extension that extends substantially orthogonally from the base portion and is configured to interact (e.g., to connect, attach, or otherwise cause to interact with) with one of the plurality of interacting regions of the lateral portion. In several embodiments, each of the plurality of carriages is positioned co-axially about one of a plurality of axes, wherein during operation each axis extends substantially parallel to the axis of rotation of the drive shaft of the motor, and wherein each of the plurality of carriages is at least intermittently rotatable about one of the plurality of axes. Depending on the embodiment, the carriages can rotate to various degrees. For example, in several embodiments, the carriages are induced to rotate through an arc of about 180 degrees.

In several embodiments, the system further comprises at least one microfluidic chip that serves to hold and process the sample according to the system In several embodiments, each microfluidic chip comprises a central body portion positioned between a first end and a second end and at least one microfluidic channel extending between the first and second ends, the at least one channel comprising varied dimensions and configured to allow passage of the sample from the first end to the second end. In several embodiments, each of the first and second end are configured to fluidically interact with the sample chamber. For case of use, each individual microfluidic chip is dimensioned to fit within a corresponding receiving region on a corresponding carriage. In several embodiments, each microfluidic chip is reversibly fluidically coupled to a sample chamber on each of the first and second ends.

Optionally, some embodiments comprise a sample chamber comprising a vent and a vent channel that is fluidly connected to the interior of the sample chamber. In several embodiments, each sample chamber is reversibly fluidically coupled to the microfluidic chip via an adapter.

In several embodiments, each carriage comprises a capture element on the first and second ends of the carriage, the capture elements configured to communicate with a release element on the lateral portion of the support plate, wherein the communication between the capture elements and release element allows the intermittent rotation of each of the plurality of carriages. In other words, the capture elements serve to hold the carriage in a desired position until such time as there is a signal (or force, or lack thereof) that allows the capture elements to disengage or otherwise cease interaction with the release element, which subsequently allows rotation of the carriage, to be followed be a reengagement of the capture element in order to stop the motion of the carriage (in several embodiments, this allows the rotation of the carriage through an arc of 180 degrees at a desired time in a tissue processing protocol). In several embodiments, the capture elements comprise magnets of a first polarity and the release element comprises a magnet of an opposite polarity.

In several embodiments, the lateral portion of the support plate comprises a disc, with the interacting regions spaced circumferentially around the disc. In some such embodiments, the lateral portion and the central portion are a unitary structure, though in other embodiments the support plate comprises multiple pieces that are connected or integrated prior to use.

In several embodiments, the lateral portion of the support plate comprises a plurality of arms, with each arm comprising a corresponding interacting region. In one embodiment, the arms and the central portion are a unitary structure. In additional embodiments, the arms and the central portion are separate structures joined together. In some embodiments, the arms are hinged relative to the central portion. In some such embodiments, the hinges allow the arms to move into the plane of the axis that is substantially parallel to the axis of rotation of the drive shaft of the motor during operation. In several embodiments, this allows for a gentle start up and stop process such that acute application or removal of centrifugal force does not disrupt the cells/tissue sample.

In several embodiments, the interacting regions of the lateral portion comprise a through hole that receives the post (or other structure) from the corresponding carriage. In several embodiments, the receiving region is positioned on an upper surface of the base portion of the carriage. In several embodiments, the post extends from a bottom surface of the base portion of the carriage. In such embodiments, the post (or other structure) extends from the bottom of the carriage and passes through the hole (receiving region) of the lateral portion (e.g., arm) and is secured (though allowing rotation relative to the lateral portion), for example by a nut, pin, clamp or other such mechanism. In several embodiments, the intermittent rotation of each of the carriages is accomplished via the interaction of gears positioned on the lateral portion with fixed teeth that induce rotation of each carriage.

In several embodiments, the lateral portion comprises at least three arms, each of the three arms comprising an interacting region configured to interact with one of at least three carriages comprising a first and second end, each of the carriages configured to reversibly interact with one of at least three microfluidic chips, each chip comprising a first end, a second end, and a body there between, each end of the microfluidic chip being fluidically coupled to a sample chamber, and the body of the chip comprising a plurality of microfluidic pathways extending between the first and second ends, and wherein the carriages are configured to intermittently rotate between a first position where the first end is positioned at a first location at a first distance from the receiving element of the central portion and a second position wherein the first end is positioned at a second location at a second distance from the receiving element of the central portion, wherein the first distance is greater than the second distance.

Depending on the embodiment, the system can optionally include an enclosure, wherein the enclosure separates the system from an external environment.

Depending on the embodiment, the system optionally further comprises a motor operably connected to the drive shaft. In several embodiments, the motor is controlled by a controller unit that allows control of the rotational speed of the motor, the controller unit comprising an interface that allows a user to program (or select from preprogrammed) a protocol to process tissue.

Also provided herein are methods for processing a biological sample. For example, in several embodiments, there is provided a method for processing a biological sample, comprising loading a biological sample into a first sample chamber that is configured to be fluidically coupled to a microfluidic chip, the chip comprising a central body portion positioned between a first end and a second end, the first end configured to be fluidically coupled to the first sample chamber and the second end fluidically coupled with a second sample chamber, at least one microfluidic channel extending between the first and second ends, the at least one channel comprising varied dimensions and configured to allow passage of the sample from the first end to the second end, reversibly coupling the microfluidic chip with a receiving region of one of a plurality of carriages that is part of a centrifugal device, the centrifugal device comprising a support plate comprising a central portion and a lateral portion, the lateral portion extending radially from the central portion and lying within a plane parallel to the plane of the central portion, each of the carriages operatively coupled to the lateral portion of the support plate and comprising a first end, a second end, and a base portion extending between the first and second ends, the base portion comprising the receiving region, each of the carriages configured to be rotatable about an axis substantially perpendicular to the plane of the central portion, wherein the carriage starts in a first position in which the first end is positioned at a first distance from the central portion of the support plate and is rotatable to a second position where the second end is positioned such that the second end is positioned at the first distance from the central portion of the support plate, and applying a rotational force to the centrifugal device, thereby causing the sample to pass from the first sample chamber coupled to the first end of the microfluidic chip through the at least one microfluidic channel extending between the first and second ends and into the second sample chamber, allowing rotation of the carriage between the first and second positions; and applying additional rotational force to cause the sample to pass from the second sample chamber through the at least one microfluidic channel extending between the second and first ends and back into the first sample chamber. In several embodiments, the biological sample comprises adipose tissue, though other tissue types can be processed using the systems and methods disclosed herein. For example, adipose tissue, tumor tissue, cellular preparations, lipoaspirates, cultured cells, and the like can readily be processed.

Further provide, in several embodiments, is a system for processing samples comprising, a support plate containing a plurality of rotatable carriages positioned radially about the support plate; and at least one microfluidic chip disposed on one of the rotatable carriages, the at least one microfluidic chip defining a fluid path formed by one or more microfluidic channels disposed therein and extending between a first port of the microfluidic chip to a second port located at an opposing end of the microfluidic chip.

In several embodiments, the support plate comprises a plurality of arms and wherein each of the plurality of arms holds a rotatable carriage. In some such embodiments, the plurality of arms are secured to a separate central hub. In several embodiments, the support plate comprises a first magnetic element disposed therein or thereon and disposed adjacent to an end of the rotatable carriage, the rotatable carriage further comprising a second magnetic element disposed therein or thereon.

Alternatively, in several embodiments, the rotatable carriages are coupled to a gear set disposed in a gear assembly mounted to the support plate, wherein the gear set includes an exposed gear on a radially outward portion of the gear assembly. In several embodiments, the gear assembly or the support plate further comprises a stationary magnet disposed therein and the rotatable carriages contains a pair of magnetic elements disposed at opposing ends thereof.

In several embodiments, the plurality of rotatable carriages is rotatable in a plane that is substantially parallel to a rotational plane of the support plate. In several embodiments, the plurality of rotatable carriages is rotatable in a plane that is substantially orthogonal to a rotational plane of the support plate.

In several embodiments, the system further comprises an electromagnet disposed in the support plate beneath each of the plurality of rotatable carriages, wherein the rotatable carriages comprise a magnetic post element extending through an aperture formed in the support plate.

In several embodiments, at least one of the first sample holding chamber and a second sample holding chamber comprise a syringe barrel, for example a standard 2 mL, 5 mL, 10 mL, 20 mL, or 60 mL syringe barrel. In several embodiments, there is additionally included a filter interposed between the at least one microfluidic chip and one of the first sample holding chamber or the second sample holding chamber. In some embodiments, the filter is located upstream of or before the microfluidic chip and is configured to filter the sample to prevent clogging of the microfluidic chip. In some examples, the upstream filter can include a mesh that is configured to cut or micronize tissue or tissue fragments to allow the sample to pass through the microfluidic chip without clogging. The cutting or micronization of the sample is configured to produce macroscopic aggregates for the purpose of microfluidic shearing in the microfluidic chips. In some embodiments, the filter is located downstream of or after the microfluidic chip to only allow a certain sized sample to pass out of the device for collection.

In several embodiments, the system also includes a sample holding chamber disposed in the rotatable carriage and coupled to the first port of the microfluidic chip and a syringe coupled to the second port of the microfluidic chip, wherein the syringe is mounted generally perpendicular to a rotational plane of the microfluidic chip. In several embodiments, the system disclosed herein can optionally comprise a vertically moveable plate or ring coupled to a plunger of the syringe. In several embodiments, the vertically moveable plate or ring comprises an internally threaded bearing mounted on rotatable, threaded rod. Optionally, certain embodiments further comprise a second motor coupled to the threaded rod.

In some embodiments, the systems have at least one of the first sample holding chamber and the second sample holding chamber comprising an inlet having a one-way valve disposed therein.

In several embodiments, there is provided a method of using the systems disclosed herein, comprising rotating the support plate to move the sample into the one or more microfluidic channels of the at least one microfluidic chip via the first port and out the second port, rotating the rotatable carriage containing the at least one microfluidic chip through approximately 180°, rotating the support plate to move the sample into the one or more microfluidic channels via the second port and out the first port, rotating the rotatable carriage containing the at least one microfluidic chip through approximately 180°, and repeating these steps a plurality of times, until a sample is processed to a desired degree.

In several such methods, the sample moves between a first sample holding chamber fluidically coupled to the first port and a second sample holding chamber fluidically coupled to the second port. In several embodiments, at least one of the first sample holding chamber and the second sample holding chamber comprises a syringe barrel.

In several embodiments, the sample comprises tumor tissue. In several embodiments, the sample comprises fat tissue. In several embodiments, the sample comprises a fluid with one or more reagents. In several embodiments, the sample comprises particles (e.g., nanoparticles, magnetic particles, particles coated with a reagent or antibody, and the like). In several embodiments, the sample comprises a cell containing fluid.

In some embodiments, after processing tissue, the methods disclosed herein further comprise injecting the processed tissue (e.g., adipose tissue) into a subject.

Supplementing the above described systems, devices and methods, there is also provided herein a system for processing samples comprising a support plate including a plurality of arms, wherein the plurality of arms extends radially from the support plate, a motor, coupled to the support plate and configured to rotate the support plate; and a plurality of carriages, wherein each of the plurality of carriages is arranged on one of the plurality of arms on the support plate, wherein each of the plurality of carriages is positioned co-axially about one of a plurality of axes, wherein each axis extends perpendicularly from the arm that the carriage is arranged on, wherein each of the plurality of carriages is configured to receive a microfluidic chip and at least one sample chamber for receiving a sample for processing, wherein the at least one sample chamber includes an opening that is fluidly connected to the microfluidic chip, and wherein each of the plurality of carriages is rotatable about one of the plurality of axes.

In several embodiments, the system further comprising a controller configured to drive the motor, wherein the controller is configured to adjust the rotational speed or rotations per minute (RPM) of the motor. In several embodiments, the controller is adjustable or programmable with a pre-determined spin program or sequence of operations. In several embodiments, the controller is configured (or configurable) to ramp up the spin rate of the motor to an RPM rate such that the sample is configured to flow from a first end of the microfluidic chip to a second end of the microfluidic chip. In several embodiments, the controller is configured to accelerate or decelerate the RPMs of the motor such that each of the plurality of carriages is configured to rotate about one of the plurality of axes.

In several embodiments, each of the plurality of carriages is configured to rotate 180 degrees about one of the plurality of axes. Moreover, in several embodiments, each of the plurality of carriages is configured to receive a first sample chamber and a second sample chamber, wherein the first sample chamber is positioned on a first end of the microfluidic chamber, and wherein the second sample chamber is positioned on a second end of the microfluidic chamber.

Some embodiments, include the at least one sample chamber being attached to an end of the microfluidic chip using an adaptor. The adaptor can include any one of a Luer slip, slip tip connectors, a Luer lock, and a rotating collar. The adaptor can comprise metal or polymer materials, depending on the embodiment, and also on whether the microfluidic chip is disposable or reusable (e.g., can be sterilized).

In several embodiments, the support plate is placed inside an encasement, the encasement configured to protect a user from the system for processing samples. The encasement comprises any material such as a plastic material or a metal, the material being provided at a thickness sufficient to prevent penetration or rupture of the encasement by decreased vacuum pressure, cold temperatures, changes in heat, or debris created by the centrifugal rotation of the support plate. In several embodiments, the encasement is configured to be opened and closed in order to place a sample, remove a sample, or manually rotate one or more carriages, if needed. In several embodiments, the encasement is optically transparent and is configured to allow the operation of the system for processing samples to be monitored.

In embodiments, comprising a plurality of arms, in some such embodiments, each of the plurality of arms further comprises a first engagement structure, a second engagement structure located a distance from the first engagement structure, wherein the first engagement structure and the second engagement structure are each configured to engage with one of a first structure located on a first end of the carriage and a second structure located on a second end of the carriage. In several such embodiments, the first and second engagement structures are configured to release and engage the first structure and the second structure interchangeably such that the carriage is configured to move between a plurality of orientations about one of the plurality of axes.

In several embodiments, the first engagement structure and the second engagement structure are magnets and the first structure and second structure comprise magnetically responsive materials. In several embodiments, the first engagement structure and the second engagement structure comprise magnetically responsive materials and the first structure and second structure are magnets. In several embodiments, the first engagement structure is located distally from the second engagement structure along a length of each of the plurality of arms. In order to cause movement of the carriage(s), in several embodiments, an acceleration or deceleration force is configured to move the carriage between the plurality of orientations. In several embodiments, the carriage comprises a gear assembly, the gear assembly is configured to move the carriage between the plurality of orientations. In some embodiments, the carriage comprises a centripetal ratchet, the centripetal ratchet configured to move the carriage between the plurality of orientations.

To enable proper flow of a sample through the microfluidic chip(s), in several embodiments, the at least one sample chamber includes a vent and a vent channel that is fluidly connected to the interior of the sample channel, wherein the vent is configured to provide laminar flow through the sample chamber (e.g., by preventing vacuum). In several embodiments, the vent is located on an opposite end of the sample chamber as the opening. Depending on the embodiment, the sample chamber can be any desired shape, including rectangular, square, ellipsoid, columnar, oval, or other polygonal shape. In one embodiment, the sample chamber is rectangular. In some alternative embodiments, the sample chamber is a syringe. In some such embodiments, the syringe comprises a chamber having an adaptor end, the adaptor end having an opening configured to fluidly connect to the microfluidic chip, a plunger comprising a seal disposed in the chamber; and a depressor attached to a distal end of the plunger and configured to advance and withdraw the plunger. In some embodiments, the syringe includes a vent and a vent channel that is fluidly connected to the interior of the chamber, wherein the vent is configured to provide laminar flow through the syringe. Additionally, in several embodiments, the syringe can optionally include a secondary syringe plunger, the secondary syringe plunger disposed within the vent channel and is configured to selectively open and close the vent channel. In such embodiments, the secondary syringe is optionally coupled to the depressor such that movement of the depressor is configured to advance and withdraw both the plunger and secondary plunger. In several embodiments, the adaptor end of the syringe is configured to receive a needle. In several embodiments, the syringe is configured to be removable from the microfluidic chip and the sample is configured to be directly injected into an injection site.

In several embodiments, each of the plurality of chambers (e.g., chambers to retain a microfluidic chip) is retained in an opening of each of the plurality of arms, wherein each of the plurality of chambers extends through the opening of each of the plurality of arms. In several embodiments, each of the plurality of chambers is retained along a plane of each of the plurality of arms. In several embodiments, each of the plurality of chambers is retained in the opening of each of the plurality of arms with at least one pin that is configured to allow out-of-plane rotation for each of the plurality of chambers. In several embodiments, the out-of-plane rotation of each of the plurality of chambers is configured to move each of the plurality of chambers between a plurality of orientations. In several embodiments, each of the plurality of chambers moves between 180 degrees of rotation (whether in-plane or out of plane). In several embodiments, each of the plurality of chambers moves between orientations where each of the plurality of chambers lies along a plane of each of the plurality of arms.

In several embodiments, the systems disclosed herein further comprise at least one filter configured to prevent larger sized sample components from passing into and clogging the microfluidic chip. In several embodiments, the filter is attached to the sample chamber in order to filter the sample prior to having the sample pass into the microfluidic passageways of the microfluidic chip. In some embodiments, the filter is located upstream of or before the microfluidic chip and is configured to filter the sample to prevent clogging of the microfluidic chip. In some examples, the upstream filter can include a mesh that is configured to cut or micronize the tissue or tissue fragments to allow the sample to pass through the microfluidic chip without clogging. The cutting or micronization of the sample is configured to produce macroscopic aggregates for the purpose of microfluidic shearing in the microfluidic chips. In some embodiments, the filter is located downstream or after the microfluidic chip to only allow a certain sized sample to pass out of the device for collection.

Additional systems are also provided for herein. For example, there is provided a system for processing samples comprising a support plate, a motor, coupled to the support plate and configured to rotate the support plate; and at least one carriage arranged on the support plate, wherein the at least one carriage is configured to receive a microfluidic chip and at least one sample chamber for receiving a sample for processing, and wherein the at least one carriage is configured to rotate in a plane parallel to a plane of the support plate.

Further, there is provided a system for processing samples comprising a support plate, a motor, coupled to the support plate and configured to rotate the support plate, and at least one carriage arranged on the support plate, wherein the at least one carriage is configured to rotate in a plane parallel to a plane of the support plate, a microfluidic chip received within the at least one carriage, wherein the microfluidic chip includes a port and at least one microfluidic channel extending along a length of the microfluidic chip, and at least one sample chamber for receiving a sample for processing, the at least one sample chamber fluidly connected to the first port of the microfluidic chip and configured to allow the sample to flow from the at least one sample chamber and along the length of the microfluidic chip.

In several embodiments, the microfluidic chip has a length between about 10 mm and 100 mm. In some embodiments, the length can be about 10 mm, about 20 mm, about 30 mm, about 40 mm, about 50 mm, about 60 mm, about 70 mm, about 80 mm, about 90 mm, about 100 mm, and between about 10-20 mm, about 30-40 mm, about 40-50 mm, about 50-60 mm, about 60-70 mm, about 70-80 mm, about 80-90 mm, about 90-100 mm and any value in between those ranges listed, including endpoints. In several embodiments, the length of the at least one microfluidic channel is less than (or equal to) a length of the microfluidic chip. In several embodiments, the width and depth of the microfluidic channel is within the range of between 5 μm and 8 mm. In some embodiments, the microfluidic channel can be between about 5-200 μm, about 200-400 μm, about 400-600 μm, about 600-800 μm, about 800-1000 μm, about 1-2 mm, about 2-4 mm, about 4-6 mm, about 6-8 mm and any value in between those ranges listed, including endpoints. It shall be appreciated that in several embodiments the microfluidic chip is removable.

The microfluidic channel can have a variety of configurations, depending on the embodiment, and the tissue to be processed. For example, in one embodiment, the microfluidic channel(s) has an hourglass configuration. In several embodiments, the at least one microfluidic channel comprises a first region comprising a stepwise taper that gradually decreases in width along a length of the at least one microfluidic channel, a constriction region, and a second region comprising a stepwise taper gradually increasing in width along a length of the at least one microfluidic channel. In additional embodiments, the at least one microfluidic channel has a series of regions of increasing width and regions of decreasing width. In several embodiments, the at least one microfluidic channel has a diamond pattern. In several embodiments, the at least one microfluidic channel includes a plurality of pockets, which are optionally fin-shaped. In several embodiments, the at least one microfluidic channel comprises a first region comprising a series of bifurcations and a second region wherein pairs of bifurcated channels are recombined. In additional embodiments, the at least one microfluidic channel comprises a plurality of wells, wherein the plurality of wells are configured to sort portions of the sample of a predetermined size.

Still additional methods are provided for herein, such as, for example, a method for processing samples comprising a sample in a sample chamber, inserting the sample chamber into at least one of a plurality of carriages, wherein the sample chamber is fluidly connected to a microfluidic chip comprising at least one microfluidic channel, wherein one of the plurality of carriages is attached to a support plate, the support plate configured to rotate about a first axis, and wherein the at least one of the plurality of carriages is configured to rotate about a second axis, the second axis parallel to the first axis, and rotating the support plate about the first axis, wherein the rotation is configured to drive the sample from the sample chamber through the at least one microfluidic channel in a first direction away from the sample chamber. In several embodiments, the method further comprises rotating the at least one of the plurality of carriages about the second axis into a second orientation. In several embodiments, the methods further comprise rotating the support plate about the first axis, wherein the rotation is configured to drive the sample through the at least one microfluidic channel in a second direction toward the sample chamber. Additionally, the methods optionally further comprise removing the sample chamber from the at least one of a plurality of carriages.

An additional system is provided, comprising a support plate including a plurality of arms, wherein the plurality of arms extends radially from the support plate, a motor, coupled to the support plate and configured to rotate the support plate, a plurality of carriages, wherein each of the plurality of carriages is arranged on one of the plurality of arms on the support plate, wherein each of the plurality of carriages is positioned co-axially about one of a plurality of axes, wherein each axis extends perpendicularly from the arm that the carriage is arranged on, wherein each of the plurality of carriages is configured to receive a microfluidic chip and at least one sample chamber for receiving a sample for processing, and wherein each of the plurality of carriages is rotatable about one of the plurality of axes, and, an encasement configured to receive the support plate, the encasement configured to protect a user form the system for processing samples, wherein the encasement includes an opening that is configured to provide access to the sample chamber. In several embodiments, the at least one sample chamber includes a vent and a vent channel that is fluidly connected to the interior of the sample channel, wherein the vent is configured to provide laminar flow through the sample chamber. In several embodiments, the at least one sample chamber includes an opening that is fluidly connected to the microfluidic chip. In several embodiments, the at least one sample chamber includes an inlet configured to allow the sample for processing to be inserted or removed from the at least one sample chamber. In one embodiment, the inlet is located opposite of the opening, though other positions may optionally be used. In several embodiments, the at least one sample chamber includes a one-way valve configured to ensure the sample stays inside the chamber during processing. In several embodiments, the interior of the sample chamber has a sloped, beveled, or otherwise shaped surface adjacent to the inlet, the surface configured to cause the sample to aggregate adjacent the inlet for easy removal of the sample after processing. In one embodiment, the vent is located on an opposite end of the sample chamber as the opening. In some embodiments, the inlet is configured to engage with a syringe, the syringe is configured to remove the sample and allow the sample to be injected directly into a target site.

In several embodiments, each of the plurality of chambers is retained in an opening of each of the plurality of arms, wherein each of the plurality of chambers extends through the opening of each of the plurality of arms. In such embodiments, each of the plurality of chambers is optionally retained along a plane of each of the plurality of arms. In several embodiments, each of the plurality of chambers is optionally retained in the opening of each of the plurality of arms with at least one pin that is configured to allow out-of-plane rotation for each of the plurality of chambers. In several such embodiments, the out-of-plane rotation of each of the plurality of chambers is configured to move each of the plurality of chambers between a plurality of orientations. In several embodiments, each of the plurality of chambers moves between 180 degrees of rotation (e.g., 0 to 45 degrees, 45-90 degrees, 90 to 135 degrees, 135 degrees to 180 degrees, etc.) In several embodiments, each of the plurality of chambers moves between orientations where each of the plurality of chambers lies along a plane of each of the plurality of arms. In several embodiments, the system further comprising a filter configured to prevent larger sized sample components from passing into and clogging the microfluidic chip. In one embodiment, the filter is attached to the sample chamber. In some embodiments, the filter is located upstream of or before the microfluidic chip and is configured to filter the sample to prevent clogging of the microfluidic chip. In some examples, the upstream filter can include a mesh that is configured to cut or micronize the tissue or tissue fragments to allow the sample to pass through the microfluidic chip without clogging. The cutting or micronization of the sample is configured to produce macroscopic aggregates for the purpose of microfluidic shearing in the microfluidic chips. In some embodiments, the filter is located downstream or after the microfluidic chip to only allow a certain sized sample to pass out of the device for collection.

In several embodiments, there is provided a system for processing samples comprising a support plate including a plurality of arms, wherein the plurality of arms extends radially from the support plate, a motor, coupled to the support plate and configured to rotate the support plate, a plurality of carriages, wherein each of the plurality of carriages is arranged on one of the plurality of arms on the support plate, wherein each of the plurality of carriages is positioned co-axially about one of a plurality of axes, wherein each axis extends perpendicularly from the arm that the carriage is arranged on, wherein each of the plurality of carriages is configured to receive a microfluidic chip and at least one sample chamber for receiving a sample for processing, and wherein each of the plurality of carriages is rotatable about one of the plurality of axes, an encasement comprising a body portion and a cover, wherein the body portion is configured to receive the processing system, and wherein the cover is disposed over the body portion and is configured to seal the processing system within the body portion and protects a user from the system for processing samples, a spin stand comprising a motor, an externally threaded rod attached to the motor, wherein rotation of the motor rotates the externally threaded rod, a plate comprising a plurality of engagement structures for retaining a syringe, wherein the plate is attached to a bearing having an internal thread, the internal thread configured to engage with the external thread of the rod, wherein rotation of the motor is configured to raise or lower the plate in a vertical direction, wherein the syringe comprises, a chamber having an opening configured to fluidly connect to the at least one sample chamber, and a plunger disposed within the chamber, wherein advancing and withdrawing the plunger evacuates and intakes the sample for processing, and wherein the plate retains a distal end of the plunger and movement of the plate in a vertical direction lower or raises the plunger within the chamber of the syringe to evacuate or intake the sample for processing.

In several embodiments, the rotary motor is attached to the cover of the encasement, while in other embodiments, the rotary motor is located external of the encasement. In several embodiments, the plate is circular, while in some embodiments, the plate comprises a ring attached to the bearing by a plurality of arms. In one embodiment, the plate comprises a central circular plate and a co-axial ring. In some embodiments, the engagement structures are hook shaped and are configured to allow insertion and removal of the distal end of a plunger. In several embodiments, the system comprises a plurality of spaced apart engagement structures to secure the syringe when it is attached to the at least one sample chamber on a first end of the microfluidic chamber or when it is attached to the at least one sample chamber on a second end of the microfluidic chamber. In several embodiments, each of the plurality of arms further comprises an engagement structure configured to engage with a corresponding structure located on each of the plurality of carriages to retain each of the plurality of carriages in a first orientation. In several embodiments, engagement structures are configured to release and engage the corresponding structure such that the carriage is configured to move between a plurality of orientations about one of the plurality of axes. In several embodiments, the engagement structures comprise magnets and the corresponding structure comprises a magnetically responsive material. Conversely, in several embodiments, the engagement structure comprises a magnetically responsive material and the corresponding structures are magnets. In certain embodiments, acceleration or deceleration forces are configured to move the carriage between the plurality of orientations. In several embodiments, the carriage comprises a gear assembly, the gear assembly is configured to move the carriage between the plurality of orientations. In several embodiments, the carriage comprises a centripetal ratchet, the centripetal ratchet configured to move the carriage between the plurality of orientations.

Methods are provided, such as a method for processing samples comprising providing a sample in at least one sample chamber, inserting the sample chamber into at least one of a plurality of carriages, wherein the sample chamber is fluidly connected to a microfluidic chip comprising at least one microfluidic channel, wherein one of the plurality of carriages is attached to a support plate, the support plate configured to rotate about a first axis, and wherein the at least one of the plurality of carriages is configured to rotate about a second axis, the second axis parallel to the first axis, and securing a syringe to the sample chamber, wherein an opening of the syringe is fluidly connected to the sample chamber and a distal end of a plunger of the syringe is removably attached to a plate, wherein the plate is attached to a motor and is configured to be rotatable and movable in a vertical direction, and wherein movement of the plate in a vertical direction lowers or raises the plunger within a barrel of the syringe to evacuate or intake the sample for processing within the sample chamber, and rotating the support plate about the first axis, wherein the rotation is configured to drive the sample from the sample chamber through the at least one microfluidic channel in a first direction away from the sample chamber. In several embodiments, the method further comprises lowering the plate in a vertical direction such that the plunger is lowered within the barrel of the syringe to evacuate the sample for processing into the sample chamber. In such methods, there is optionally a step in which the plate is raised in a vertical direction such that the plunger is raised within the barrel of the syringe to remove the sample for processing from the sample chamber. In several embodiments, the method further comprises rotating the at least one of the plurality of carriages about the second axis into a second orientation.

As discussed above, the microfluidic chip comprises one or more microfluidic flow paths. In several embodiments, the paths comprise regions of compression (e.g., the walls of the path are a lesser distance from one another) and regions of expansion (e.g., the walls of the path are a greater distance from one another). FIG. 16 shows a non-limiting embodiment of a chip with two inlet/outlets, and a single expanded flow region positioned between two compressed flow regions. In several embodiments, a plurality of expansion and compression regions are formed in a microfluidic flow path within the chip. FIG. 17 shows a non-limiting embodiment in which the chip comprises two inlets/outlets, and three expansion regions positioned between alternating compression regions. As discussed above, in several embodiments the compression/expansion regions facilitate activation of certain cells within the biological sample.

In some embodiments the carriage comprises a spring-like material (e.g., coiled spring, elastomer, etc.) that causes the floor of the carriage to be pushed upward towards the fixed top, and thus hold the microfluidic chip in position during operation of the device. In some examples, the floor of the carriage comprises a wedge-shaped lateral extension on one side (coming out of the plane of the figure towards the viewer) that can be depressed in order to move the floor downwards (optionally in an arcuate fashion) in order to position and/or remove the microfluidic chip.

In still additional embodiments, there is provided the use of a processed tissue sample for treatment of a medical condition. In several embodiments, the condition is diabetic ulcers. In several embodiments, the condition is one that is improved or benefits from activated cells, such as stem cells. In several embodiments, there is provided use of activated stem cells from adipose tissue that result from the processing methods and systems disclosed herein, for use in the manufacture of medicament for treating a disease or ailment.

In certain embodiments, treatment of a subject with mechanically processed adipose-derived stem cells (AD-SCs) described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy. Administration can be by a variety of routes, including, without limitation, intravenous, intra-arterial, subcutaneous, intramuscular, intrahepatic, intraperitoneal and/or local delivery to an affected tissue.

System for Processing Biological Samples

Disclosed are systems for processing biological samples. FIGS. 1A-1B, 2A-2B, 23A-23B. 24, 25A-25B, 26A-26B, and 27A-27F illustrate non-limiting embodiments of systems for processing biological samples. In some embodiments, each of the systems for processing biological samples can comprise a motor coupled to a vertically oriented rotatable chuck, wherein the support plate is mounted on or secured to the rotatable chuck.

Overview of Centrifugal Device

FIG. 1 illustrates an embodiment a centrifugal device for the processing of a biological sample. As will be described in more detail below, the centrifugal device includes a base with a plurality of carriages and at least one chip assembly attached to the base portion. Application of rotational and/or centrifugal force to the at least one chip assembly can allow bidirectional flow of the biological sample in the chip assembly which can help to process the biological sample for subsequent use in treatment.

Figure 1A:
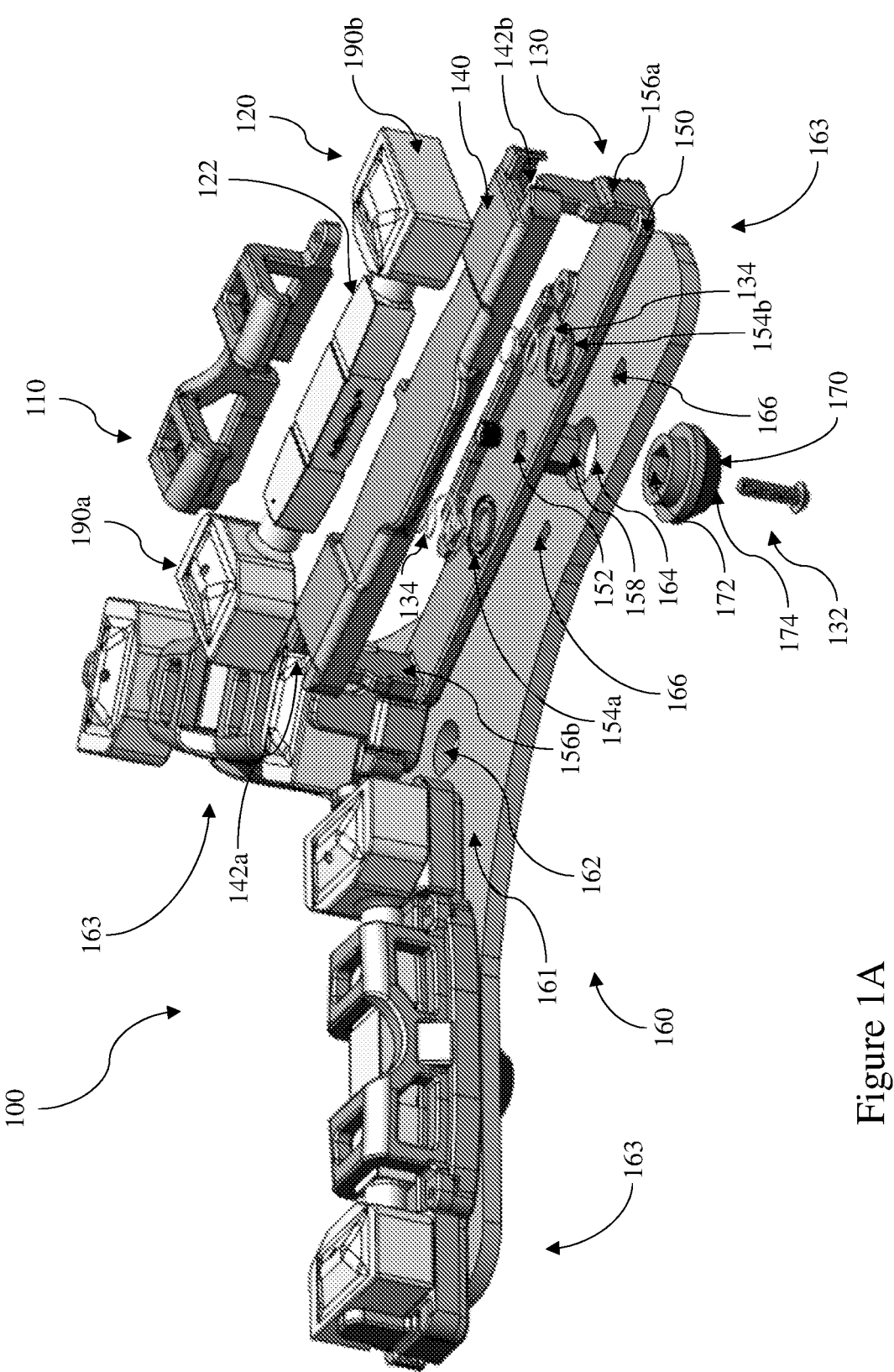
FIGS. 1A-1B illustrate an exploded view of an embodiment of a system for processing biological samples.
Figure 1B:
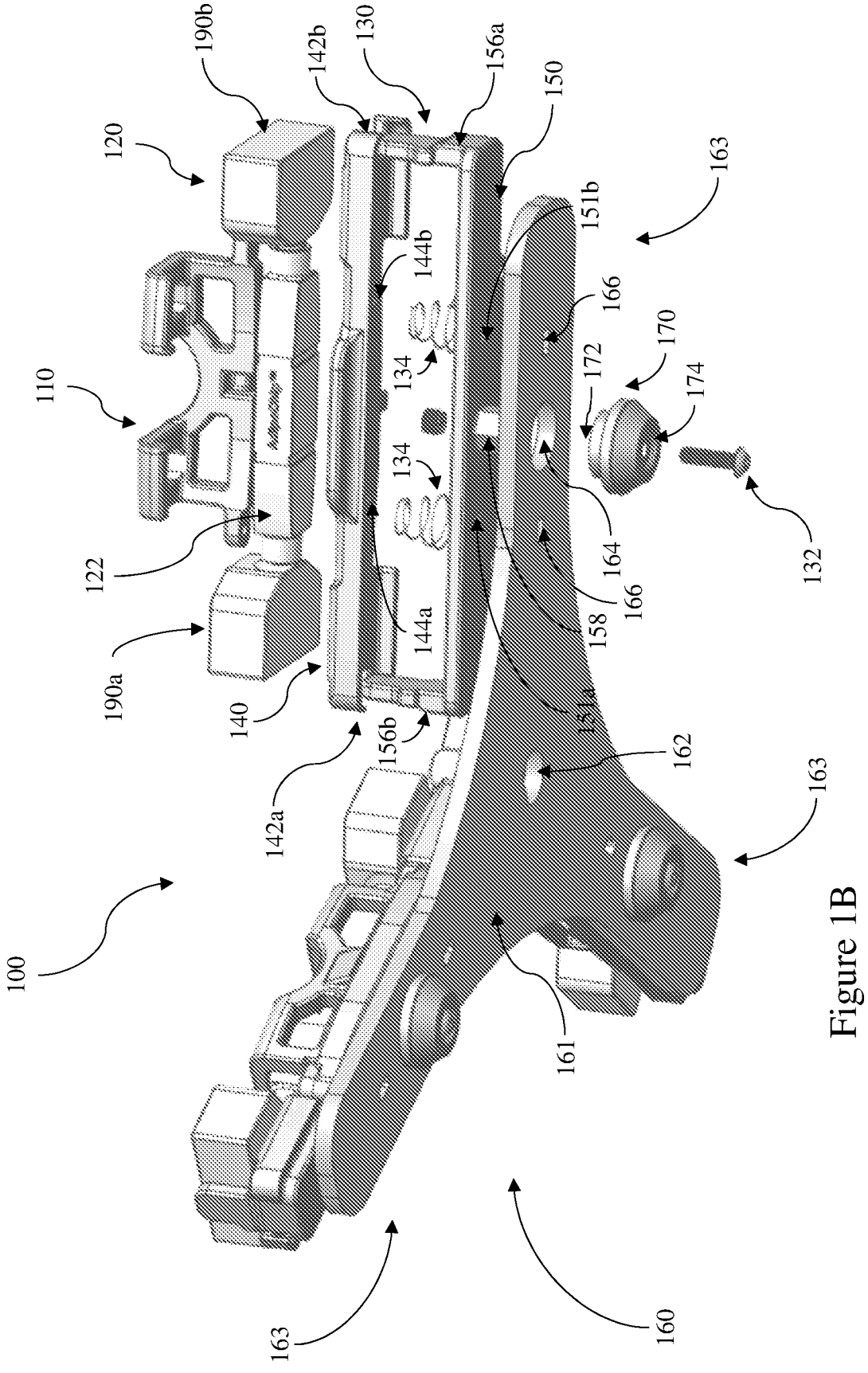

FIGS. 1A-1B illustrate an embodiment of a centrifugal device 100 for the processing of a biological sample. As shown in FIGS. 1A and 1B, the centrifugal device 100 can include a base 160 with a central portion 161 and a plurality of lateral arms 163. The central portion 161 can engage with a portion of a component of a motor, wherein the motor can rotate the base 160. Each of the lateral arms 163 can extend radially from the central portion 161 of the base 160. As shown in FIGS. 1A-1B, each of the lateral arms 163 can include an opening 164 and a plurality of pedestal mating openings 166 configured to receive and retain a base of a carriage 130. In some embodiments, the carriage 130 can be secured to each of the lateral arms 163 with a screw cap 170 and a screw 132.

As shown in FIGS. 1A-1B, the centrifugal device 100 can retain a plurality of carriages 130. Depending on the embodiment, the plurality of carriages 130 are of the same quantity as the number of lateral arms 163, though in some embodiments, fewer carriages 130 are used than the number of lateral arms 163. As will be discussed in more detail below, each of the carriages 130 can include a clamp 110, a spring platform 140, and a base platform 150. Each of the base platforms 150 can include a first arm 156a and a second arm 156b that engages a corresponding a first mating area 142a and a second mating area 142b of the spring platform 140. As will be discussed in more detail below, the carriage 130 can include one or a plurality of springs 134 between the base platform 150 and the spring platform 140. In some examples, the carriage 130 can include a clamp 110 that can secure a chip assembly 120 on the carriage 130.

Each of the carriages 130 can secure a chip assembly 120. As will be discussed in more detail below, each of the chip assembly 120 can include a microfluidic chip 122 and a sample chamber 190a secured at a first end of the microfluidic chip 122 and a sample chamber 190b secured at a second end of the microfluidic chip 122.

Figure 2A:
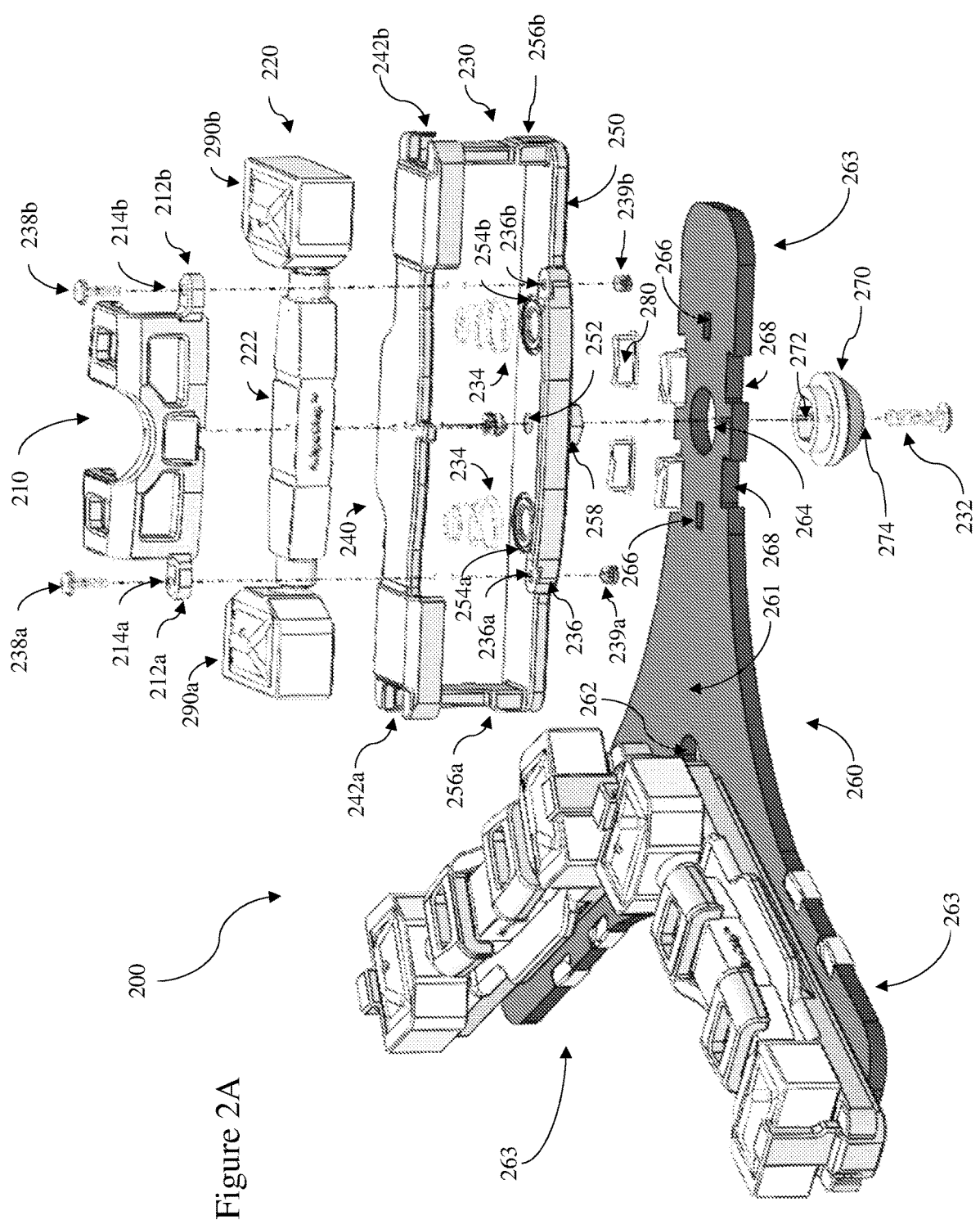
FIGS. 2A-2B illustrate an exploded view of another embodiment of a system for processing biological samples.
Figure 2B:
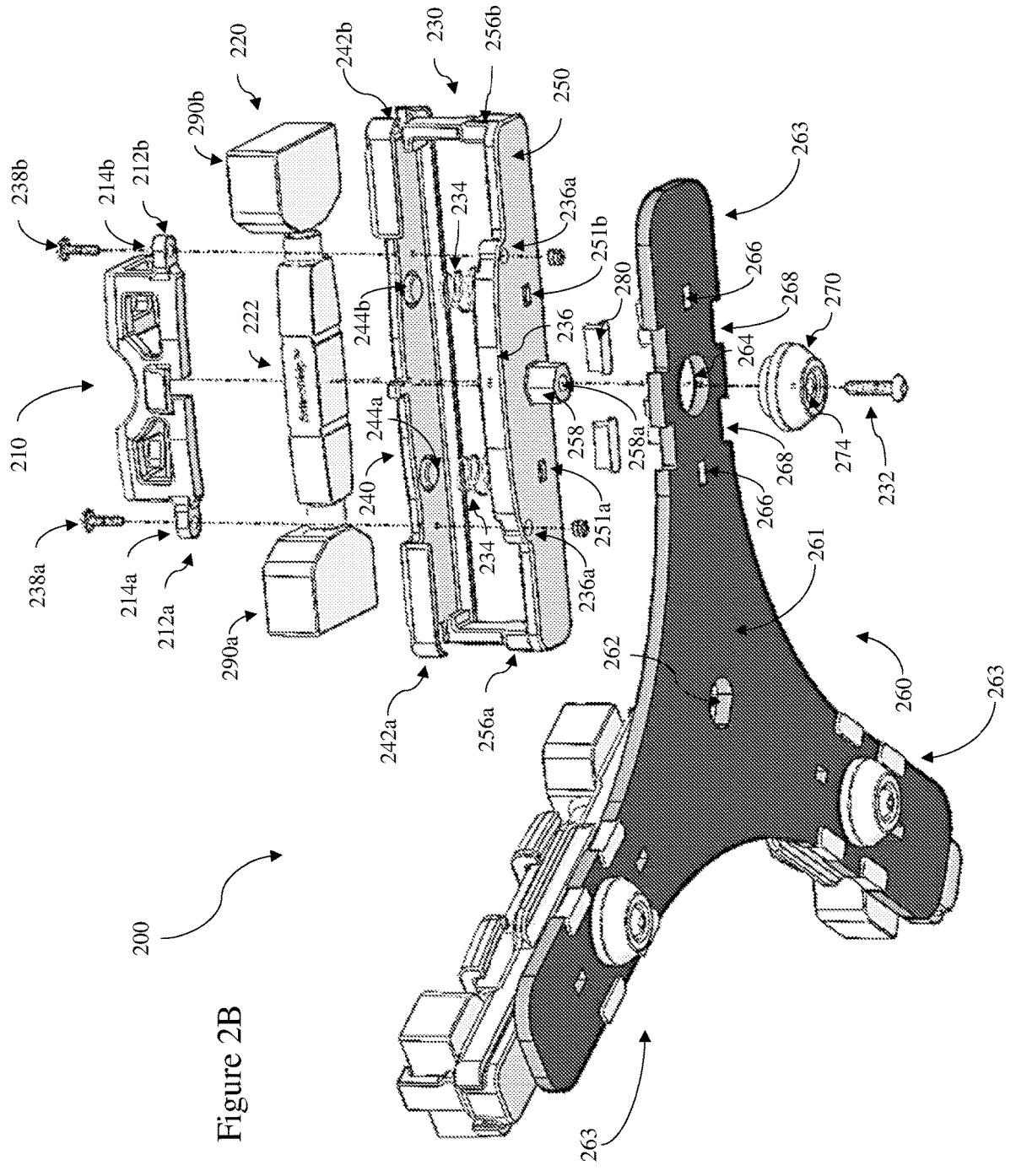

FIGS. 2A-2B illustrate another embodiment of a centrifugal device 200 for processing a biological sample. The centrifugal device 200 is similar to the centrifugal device 100 illustrated in FIGS. 1A and 1B. As shown in FIGS. 2A and 2B, the centrifugal device 200 can include a base 260 with a central portion 261 and a plurality of lateral arms 263. The central portion 261 can engage with a portion of a component of a motor, wherein the motor can rotate the base 260. Each of the lateral arms 263 can extend radially from the central portion 261 of the base 260. In some embodiments, as shown in FIGS. 2A-2B, each of the lateral arms 263 can include an opening 264 and a plurality of pedestal mating opening 266 configured to receive and retain a base of a carriage 230. Like the centrifugal device 200, the carriage 230 of the centrifugal device 200 can be secured to each of the lateral arms 263 with a screw cap 270 and a screw 232. As will be discussed in more detail below, each of the lateral arms 263 of the base 260 can include a plurality of cutouts 268 that can engage a plurality of rotor feet inserts 280.

As shown in FIGS. 2A-2B, the centrifugal device 200 can retain a plurality of carriages 230. The carriage 230 is similar to the carriage 130 discussed above and includes a clamp 210, a spring platform 240, and a base platform 250. Each of the base platforms 250 can include a first arm 256a and a second arm 256b retaining the spring platform 240 at a corresponding first mating area 242a and second mating area 242b. The carriage 230 can include one or a plurality of springs 234 between the base platform 250 and the spring platform 240. The carriage 230 can also include a clamp 210 that can secure a chip assembly 220 to the carriage 230. The clamp 210 can include a first mounting flange 212a and a second mounting flange 212b that are configured to engage with a shoulder 236 of the base platform 250. In some embodiments, each of the first mounting flange 212a and the second mounting flange 212b include a first opening 214a and a second opening 214b that are aligned with a first opening 236a and a second opening 236b. In some examples, the clamp 210 can be secured on the carriage 130 by inserting a plurality of screws through the holes of the clamp 210 and the base platform 250. As shown in FIGS. 2A-2B, the first screw 238a can be inserted through the first opening 214a and the first opening 236a and the second screw 238b can be inserted through the second opening 214b and the second opening 236b.

Each of the carriage 230 can secure a chip assembly 220. Like the chip assembly 120, each of the chip assembly 220 can include a microfluidic chip 222 and a sample chamber

290a secured at a first end of the microfluidic chip 222 and a sample chamber 290b at a second end of the microfluidic chip 222.

Overview of Carriage Assembly

Figure 3A:
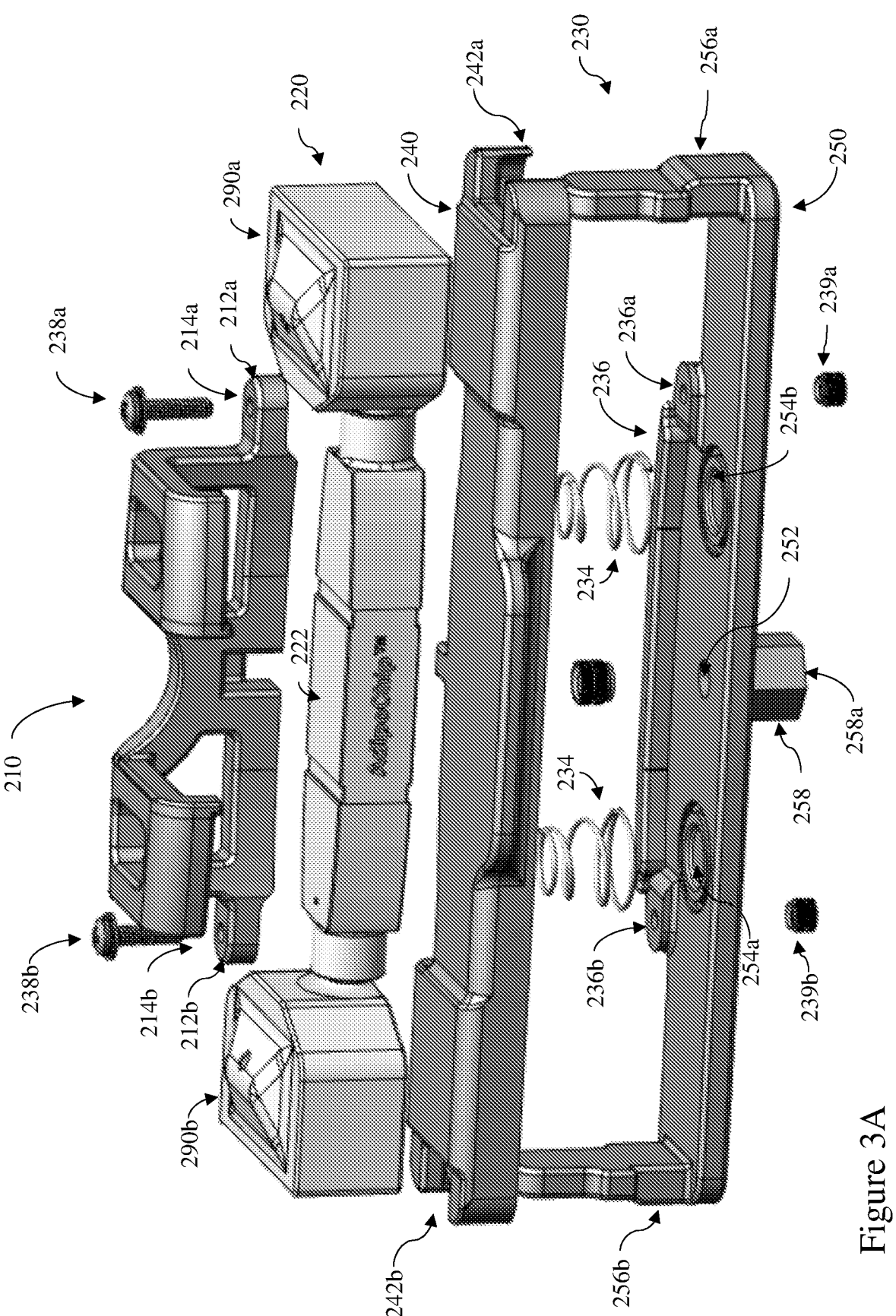
FIGS. 3A-3B illustrate view of a carriage assembly.
Figure 3B:
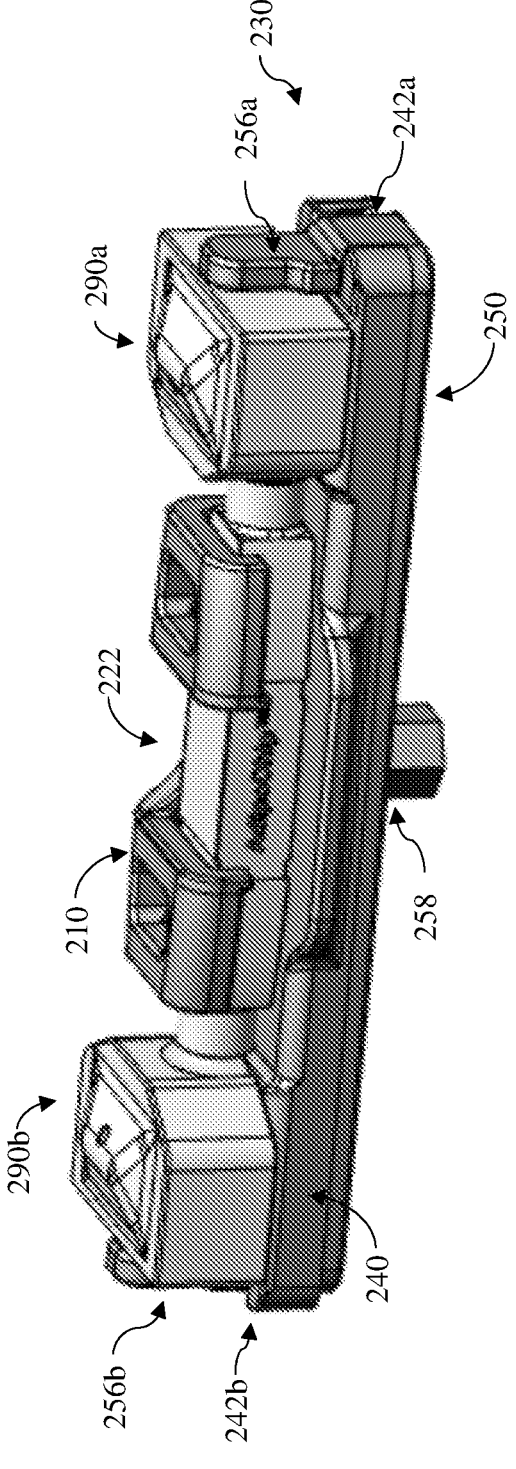

FIGS. 3A-3B illustrates an enlarged view of an embodiment of the carriage 230. Unless mentioned otherwise, the discussion of the carriage 230 and its components below can be largely applied to the carriage 130 illustrated in FIGS. 1A-1B.

As discussed above, the carriage 230 can include the base platform 250, the spring platform 240, and the clamp 210 to secure the chip assembly 220. The base platform 250 can include the first arm 256a and the second arm 256b to receive the spring platform 240. The base platform 250 can include a post 258 that extends from a base of the base platform 250 to extend through one of the opening 264 of the lateral arms 263 of the base 260. In some embodiments, the post 258 can include a channel with a distal opening 258a and an opening 252 through a top surface of the base platform 250. The distal opening 258a can receive the screw 232 through the post 258 and into the base platform 250. In some embodiments, the outside surface of the post 258 can be shaped to be received into a proximal opening 272 of the screw cap 270. The screw 232 can be configured to extend through a distal end 270b of the screw cap 270, the distal opening 258a of the post 258, and the opening 252 to secure one of the carriages 230 to one of the lateral arms 263. In some embodiments, the screw 232 is secured via a threaded fixture (e.g., a nut and bolt) that provides sufficient force to affix the carriage 230 to the lateral arm 263 but still allow rotation of the carriage. In some embodiments, as shown in FIG. 2B, a bottom side of the base platform 250 can include a first pedestal 251a and a second pedestal 251b that can each engage with one of the pedestal mating openings 266.

The carriage 230 can also include a spring platform 240. The spring platform 240 can include a first mating area 242a and a second mating area 242b. The first mating area 242a and the second mating area 242b are configured to receive each of the first arm 256a and the second arm 256b. Although FIGS. 3A-3B illustrate the spring platform 240 and the base platform 250 as separate components, in some embodiments, the spring platform 240 and the base platform 250 can be integrally formed.

The carriage 230 can include a clamp 210 that is configured to secure the chip assembly 220 on the base platform 250 of the carriage 230. As discussed above, the clamp 210 can include the first mounting flange 212a with the first opening 214a and the second mounting flange 212b with the second opening 214b that are configured to align with the first opening 236a and the second opening 236b on the shoulder 236 of the base platform 250. In some embodiments, the clamp 210 can be secured to the base platform 250 by inserting the first screw 238a through the first opening 214a and the first opening 236a and by inserting the second screw 238b through the second opening 214b and the second opening 236b.

In some embodiments, an upper surface of the base platform 250 has positioned on it one or more springs (e.g., coil springs, leaf springs, etc.) or another deformable material that returns, at least substantially, to an original position after a force is applied to it and released (e.g., elastomeric material). As shown in FIGS. 3A and 3B, a plurality of springs 234 can be secured between the spring platform 240 and the base platform 250. As illustrated in FIG. 3A, the base platform 250 can include a distal spring holder 254a and a distal spring holder 254b that can receive a base portion of each of the springs 234. FIG. 2B illustrates the spring platform 240 with a proximal spring holder 244a and a proximal spring holder 244b on an underside of the spring platform 240. The proximal spring holder 244a and the proximal spring holder 244b can receive a top portion of each of the springs 234. As shown in FIG. 3B, when the chip assembly 220 is secured to the carriage 230, the plurality of springs 234 are compressed between the spring platform 240 and base platform 250. In some embodiments, the plurality of springs 234 are configured to provide an upward force against the spring platform 240. This upward force can help to push the spring platform 240 upward against the chip assembly 220 such that the chip assembly 220 is snugly secured between the spring platform 240 and the clamp 210. The spring-tension movement of the spring platform 240 can be allow a microfluidic chip 222 to be held in position by being pushed upward against a bottom surface of the clamp 210. In operation, the spring pressure can allow the microfluidic chip 222 to be securely held in the carriage 230 as the central portion of the device is subjected to rotational force, and also as the carriages are rotated about an axis substantially parallel to the axis of rotational forced applied to the device.

To insert or remove the microfluidic chip 222 from the carriage 230, a user applies a downward force to the microfluidic chip 222 or the base platform 250 which further compresses the springs 234 and increases the distance between the microfluidic chip 222 and the base of the clamp 210. This can allow movement (e.g., insertion or removal) of the microfluidic chip 222 relative to the carriage 230. As will be discussed in more detail below, the clamp 210 can have reliefs or other openings to assist in the removal of the chip.

Chip Assembly

Figures 4A, 4B:
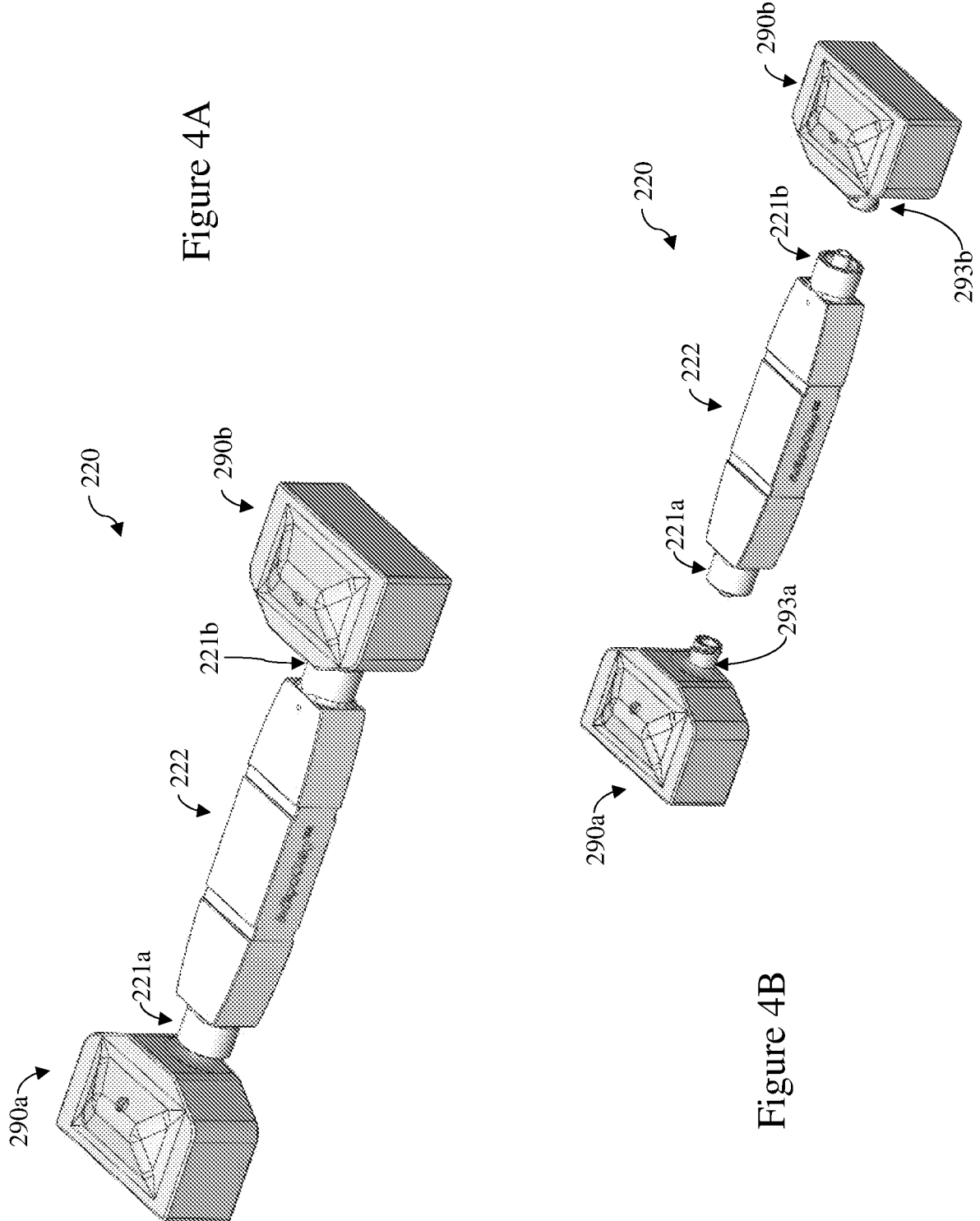
FIGS. 4A-4B illustrate an embodiment of a chip assembly.

FIGS. 4A-4B illustrates an embodiment of the chip assembly 220. As discussed above, unless mentioned otherwise, the discussion of the chip assembly 220 and its components below can be largely applied to the chip assembly 120 illustrated in FIGS. 1A-1B.

The chip assembly 220 can include a microfluidic chip 222 that is fluidly coupled to a first sample holding chamber 290a and a second sample holding chamber 290b. The sample holding chamber 290a can be fluidically coupled to the at least one microfluidic chip via the first port 221a and the second sample holding chamber 290b fluidically coupled to one of the microfluidic chips 222 via the second port 221b. As illustrated in FIGS. 4A-4B and FIGS. 14A-14F, each of the first sample holding chamber 290a and the second sample holding chamber 290b can be fluidically coupled to one of the microfluidic chip 222. The sample holding chamber 290a can be fluidly connected to a first end of the microfluidic chip 222 by engaging a first port 293a of the sample holding chamber 290a with the first port 221a of the microfluidic chip 222. The sample holding chamber 290b can be fluidly connected to a second end of the microfluidic chip 222 by engaging a second port 293b of the sample holding chamber 290b with the second port 221b of the microfluidic chip 222.

In some embodiments, adapters are interposed between the first port 221a and the first sample holding chamber 290a and the second port 221b and the second sample holding chamber 290b. In some embodiments, the at least one microfluidic chip comprises a first sample holding chamber and a second sample holding chamber disposed in the at least one microfluidic chip.

As will be discussed in more detail below, the chip assembly 220 can allow sample in either or both of the sample holding chamber 290a and the sample holding chamber 290b to move bidirectionally through the sample holding chamber 290a, the microfluidic chip 222, and the sample holding chamber 290b.

Microfluidic Chip

FIGS. 5A-5C, 7A-7C, 8A-8B, 9-10, 11A-11B, 12A-12B, and 13A-13B illustrate various embodiments of the microfluidic chip for use in the chip assembly 220. The disclosed microfluidic chips can include a fluid path with a microfluidic channel with a plurality of expansion and constriction regions along a length of the channel. In some embodiments, the plurality of expansion and constriction regions are defined by curved walls in the microfluidic channel. In some examples, the plurality of expansion and constrictions regions are defined by angled walls in the microfluidic channel. In some embodiments, the fluid path can include a plurality of branching channels of decreased dimensions that recombine with a plurality of branching channels of increased dimensions. Each branching channel can include a bifurcation. In some embodiments, the bifurcation can be a sharpened edge. In some embodiments, the microfluidic chips can be used in a pump system. The microfluidic chip can be fluidly connected to a luer lock and a syringe fluidly connected to the luer lock.

Figures 5A, 5B:
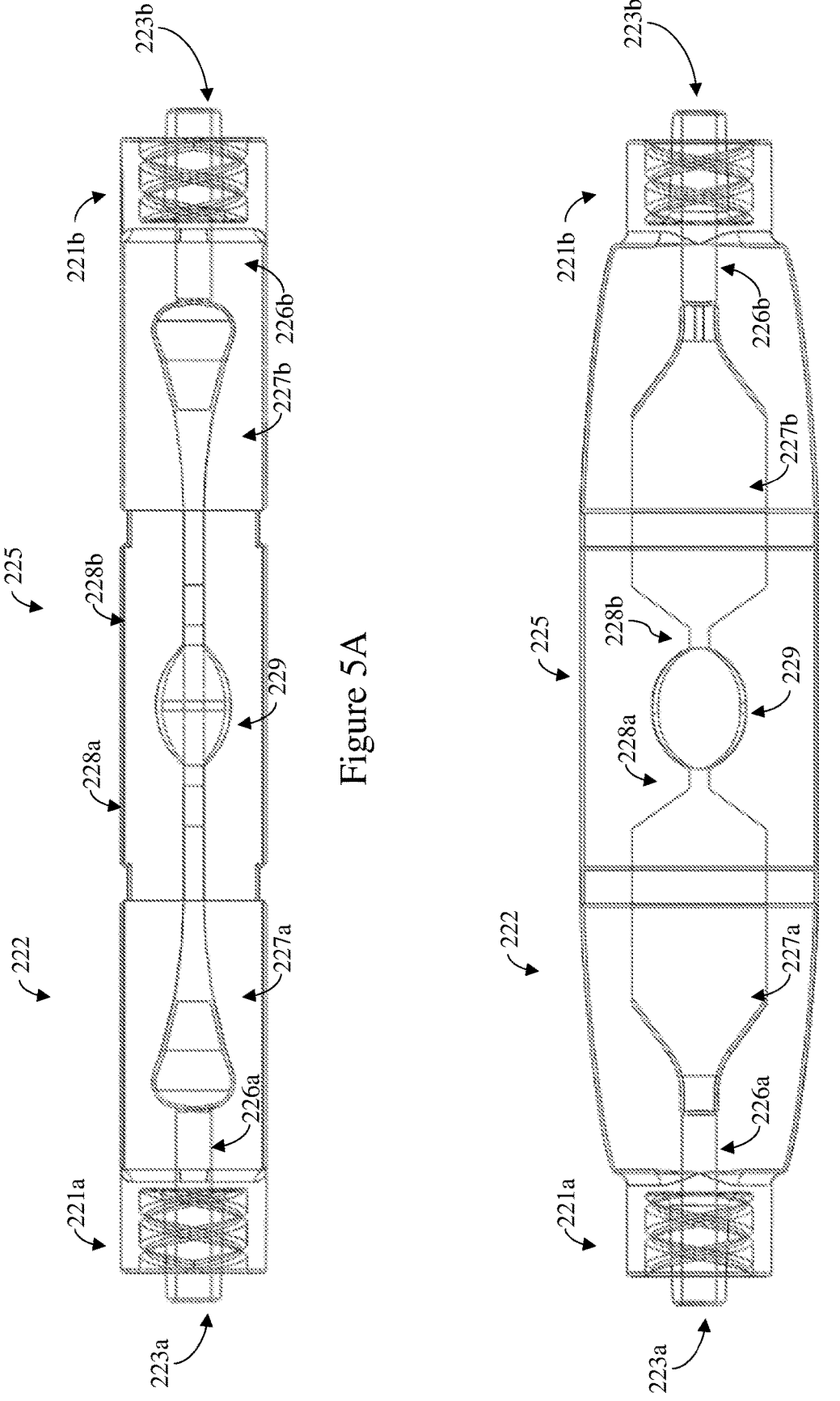
FIGS. 5A-5C illustrate an embodiment of a microfluidic chip configured to be secured in the chip assembly of FIGS. 4A-4B.
Figure 5C:
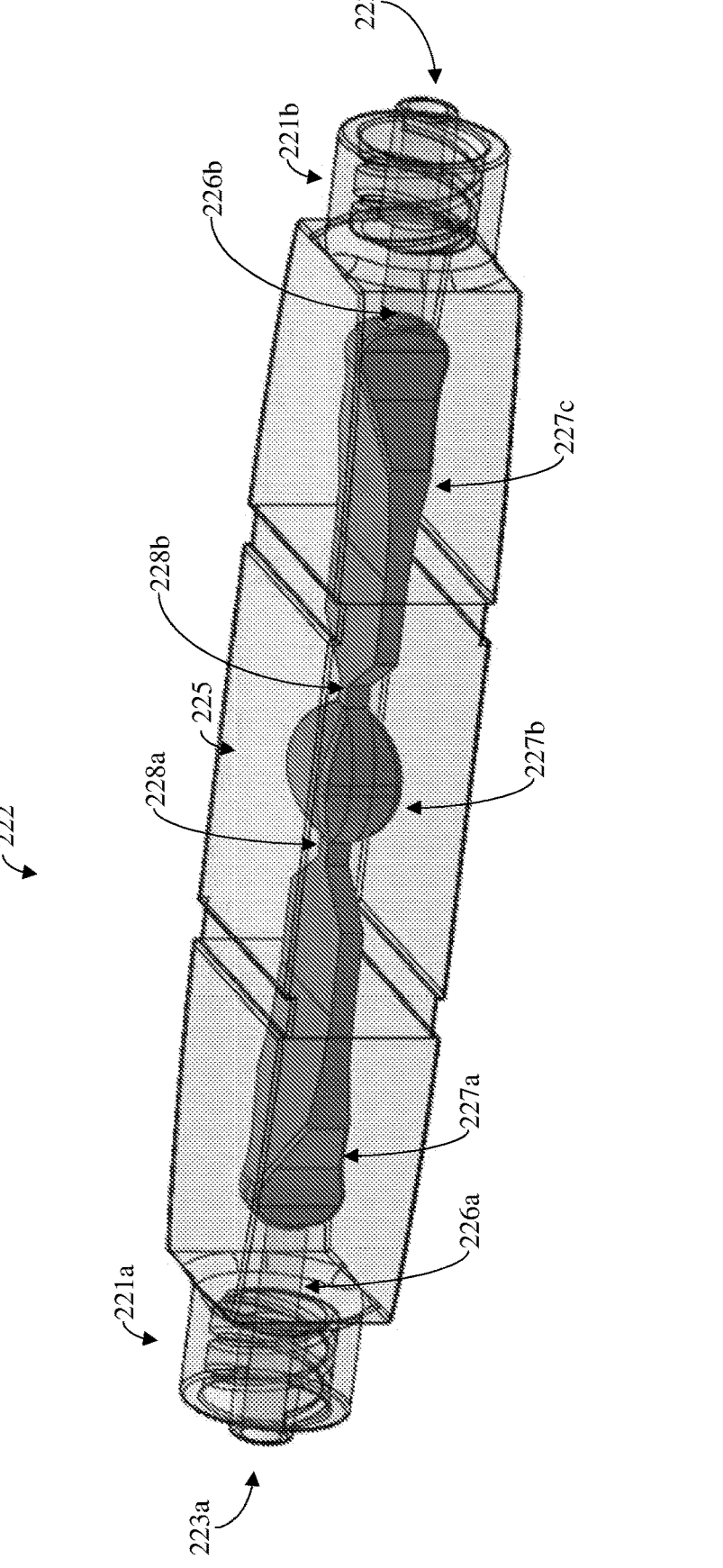

FIGS. 5A-5C illustrates an embodiment of a microfluidic chip 222. FIG. 5A illustrates a side view of the microfluidic chip 222, FIG. 5B illustrates a top view of the microfluidic chip 222, and FIG. 5C illustrates an isometric three-dimensional view of the microfluidic chip 222. The microfluidic chip 222 can include a body 225 with a first port 221a at a first end and a second port 221b at a second end of the body 225. The first port 221a can include an opening 223a that is fluidly connected to a first end of the fluid path of the microfluidic chip 222. The second port 221b can include an opening 223b that is fluidly connected to a second end of the fluid path of the microfluidic chip 222. The fluid path of the microfluidic chip 222 can extend from the opening 223a and the opening 223b. In some embodiments, the fluid path of the microfluidic chip 222 is symmetrical. However, in other embodiments, the fluid path of the microfluidic chip 222 can be asymmetrical, or a combination of symmetrical and asymmetrical portions. Although the present disclosure discusses the microfluidic chip 222 and the associated fluid path as extending between "first" and "second" ends, the orientation of the microfluidic chip 222 can be interchangeable as the flow within the chip assembly 220 and the microfluidic chip 222 can be bidirectional.

As illustrated in FIGS. 5A-5C, the fluid path of the microfluidic chip 222 can include a plurality of expansion and compression portions. For example, as illustrated, the fluid path of the microfluidic chip 222 can include a first channel 226a, a first expansion portion 227a, a first compression portion 228a, an expansion region 229, a second compression portion 228b, a second expansion portion 227b, and a second channel 226b.

In some embodiments, the fluid path of the microfluidic chip 222 includes a constricting first channel 226a that is closest to the opening 223a of the first port 221a. The first port 221a can have a length, width, or diameter from between about 0.5 mm to about 4 mm in size. In some embodiments, the length, width, or diameter can be about 0.5 mm, about 1 mm, about 1.5 mm, about 2.0 mm, about 2.5 mm, about 3.0 mm, about 3.5 mm, about 4.0 mm, between about 0.5-1 mm, about 1-1.5 mm, about 1.5-2.0 mm, about 2.5-3.0 mm, about 3.0-3.5 mm, about 3.5-4.0 mm, and any value in between those ranges listed, including endpoints. The first channel 226a can expand and increase in width, height, and/or diameter as the first channel 226a is fluidly connected with the first expansion portion 227a. As shown in FIG. 5C, the first expansion portion 227*a* is in the shape of a three-dimensional tear drop. The first expansion portion 227*a* can have a width, height, and/or diameter that is greater than the first channel 226*a*. The first expansion portion 227*a* can range from between about 0.3 mm to about 5 mm. In some embodiments, the length, width, or diameter can be about 0.3 mm, about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.3-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. The first expansion portion 227*a* can be fluidly connected to a first compression portion 228*a*. The flow path can constrict in the first compression portion 228*a* wherein the first compression portion 228*a* has a smaller width, height, and/or diameter than the first expansion portion 227*a*. The first compression portion 228*a* can range from between about 0.3 mm to about 3 mm in width, height and/or diameter. In some embodiments, the length, width, or diameter can be about 0.3 mm, about 0.5 mm, about 1 mm, about 1.5 mm, about 2.0 mm, about 2.5 mm, about 3.0 mm, between about 0.3-1 mm, about 1-1.5 mm, about 1.5-2.0 mm, about 2.5-3.0 mm, and any value in between those ranges listed, including endpoints. The fluid path can expand and increase in width, height, and/or diameter as the first compression portion 228*a* is fluidly connected with the second expansion region 229. The second expansion region 229 can range from between about 0.3 mm to about 5 mm. In some embodiments, the length, width, or diameter can be about 0.3 mm, about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.3-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. In some embodiments, the second expansion region 229 is in the shape of a spherical or elliptical expansion that has a greater length, width, and/or diameter than the first compression portion 228*a*. The second expansion portion 229 is fluidly connected to the second compression portion 228*b*. The fluid path constricts at the second compression portion 228*b* such that the width, height, and/or diameter of the compression portion 228*b* is less than the width, height, and/or diameter of the second expansion portion 227*b*. The second compression portion 228*b* can range from about 0.3 mm to about 3 mm in length, width and/or diameter. In some embodiments, the length, width, or diameter can be about 0.3 mm, about 0.5 mm, about 1 mm, about 1.5 mm, about 2.0 mm, about 2.5 mm, about 3.0 mm, between about 0.3-1 mm, about 1-1.5 mm, about 1.5-2.0 mm, about 2.5-3.0 mm, and any value in between those ranges listed, including endpoints. The second compression portion 228*b* is fluidly connected to the third expansion portion 227*c* and the fluid path expands to a third expansion portion 227*b*. The third expansion portion 227*b* expands such that the width, height, and/or diameter of the third expansion portion 227*b* is greater than the width, height, and/or diameter is greater than the second compression portion 228*b*. The second expansion portion 227*b* can range from between about 0.3 mm to about 5 mm. In some embodiments, the length, width, or diameter can be about 0.3 mm, about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.3-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. The third expansion portion 227*b* can have a three-dimensional tear-drop or other arcuate shape. The third expansion portion 227*b* can be fluidly connected and constrict to the second channel 226*b*. The second channel 226*b* can have a width, height, and/or diameter that is less than the width, height, and/or diameter of the expansion portion 227*b*. The second channel 226*b* can have a size range from about 0.5 mm to about 4 mm in length, width and/or diameter. In some embodiments, the length, width, or diameter can be about 0.5 mm, about 1 mm, about 1.5 mm, about 2.0 mm, about 2.5 mm, about 3.0 mm, about 3.5 mm, about 4.0 mm, between about 0.5-1 mm, about 1-1.5 mm, about 1.5-2.0 mm, about 2.5-3.0 mm, about 3.0-3.5 mm, about 3.5-4.0 mm, and any value in between those ranges listed, including endpoints. In some embodiments, the fluid path of the microfluidic chip 222 is symmetrical, however, in other embodiments, the fluid path of the microfluidic chip 222 can be asymmetrical, or a combination of symmetrical and asymmetrical portions. In some embodiments, the ratio between the first channel 226*a* and the expansion portion 227*a* can range between 1:1 and 1:17. In some examples, the ratio between the expansion portion 227*b* and the expansion portion 227*b* can range between 1:1 and 1:17. In some embodiments, the ratio between the compression portion 228*a* or the compression portion 228*b* and the expansion region 229 can range between 1:1 and 1:17.

FIGS. 6A-6D illustrates enlargements of the fluid path of the microfluidic chip 222. FIG. 6A illustrates an enlarged view of the port 221 (i.e., the first port 221*a* and/or the second port 221*b*) and the opening 223 (i.e., the opening 223*a* and/or the opening 223*b*) on either end of the microfluidic chip 222. In some embodiments, the port 221 can be a luer lock adapter for use with a syringe or other luer lock connections. In some embodiments, the port 221 can instead be a slip luer, or any other type of luer connection. The opening 223 of the port 221 is fluidly connected with the inlet channel 226 (i.e., the first channel 226*a* and the second channel 226*b*). The inlet channel 226 can allow for an increase in velocity of the fluid moving through it and cause laminar flow. FIG. 6B illustrates the expansion portions 227 of first expansion portion 227*a* and third expansion portion 227*c*. In some embodiments, the expansion portions 227 can be in the shape of a "tear drop." The expansion portions 227 can lower the velocity to allow for turbulent flow that mixes and vortexes the fluid flowing through the fluid path of the microfluidic chip 222. FIG. 6C illustrates the compression zones 228 of compression portion 228*a* and compression portion 228*b*. The compression zones can change the flow again to a laminar flow profile that helps to increase the velocity of the fluid. The compression zones 228 can provide high shear force due to interaction of the sample against the walls of the fluid path. FIG. 6D illustrates the second expansion region 229. As discussed above, the expansion region 229 can have a spherical and/or elliptical shape. The expansion region 229 can lower the velocity of the fluid by causing turbulent and vortexing flow. The increasing and decreasing of the velocity of fluid flow can help with breaking down tissue, for example adipose tissue, for reinjection.

The microfluidic chips disclosed above can be manufactured by various methods. For example, the microfluidic chips can be manufactured using additive manufacturing, subtractive manufacturing, injection molding, resin molding, urethane casting, 3D printing, or layer lamination. The microfluidic chips can be made of a range of materials that can include, for example, plastics (polycarbonate, acrylic, etc.), polyurethane, or metals (aluminum, steel, stainless steel, surgical steel, brass, copper, etc.).

Figures 7A, 7B, 7C:
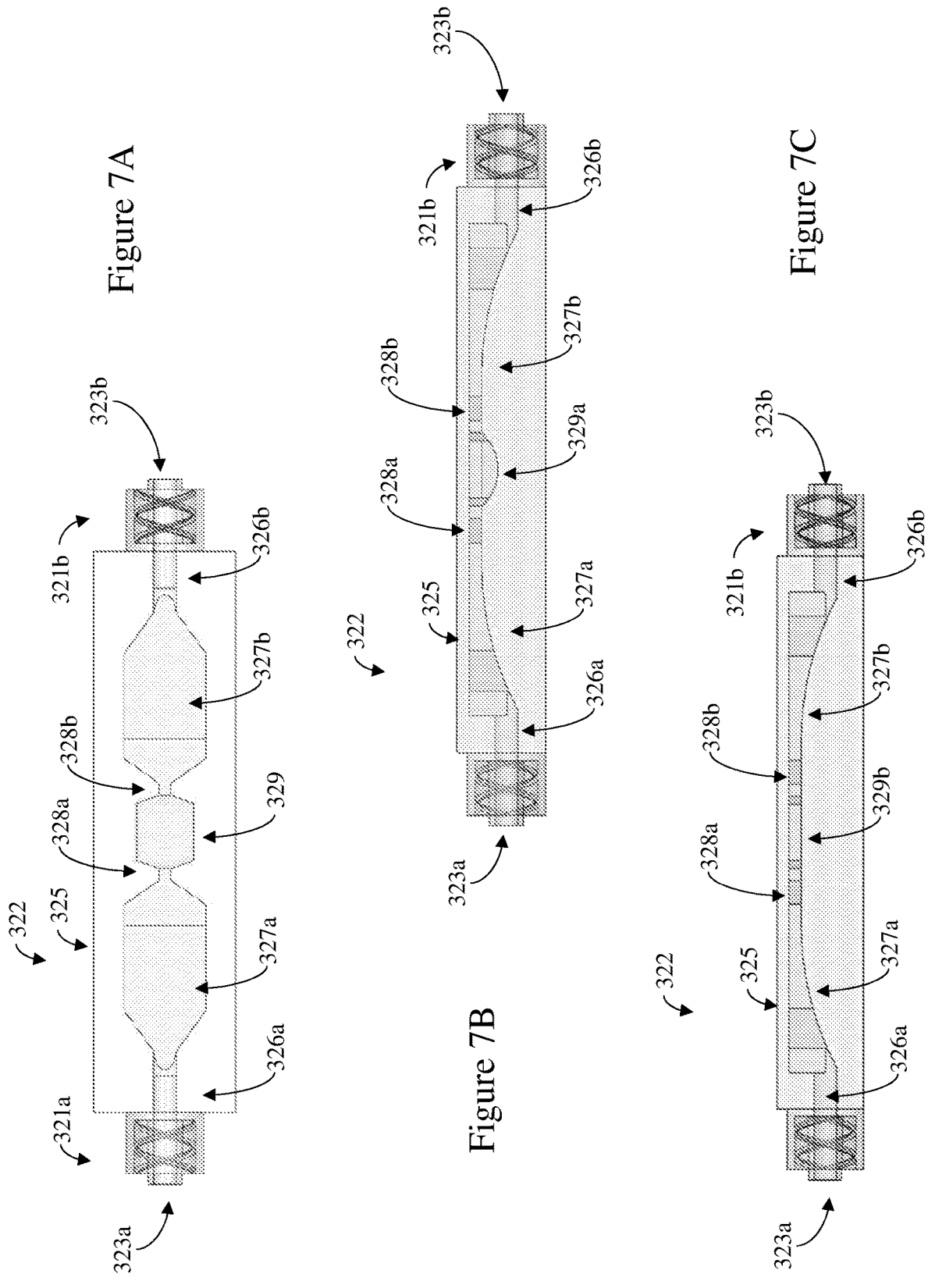
FIGS. 7A-7C illustrate another embodiment of a microfluidic chip configured to be secured in the chip assembly of FIGS. 4A-4B.

FIGS. 7A-7C illustrates an embodiment of a microfluidic chip 322. FIG. 7A illustrates a top view of the microfluidic chip 322, FIG. 7B illustrates a side view of the microfluidic chip 322 wherein a second expansion region 329 has a half-sphere shape, and FIG. 7C illustrates a side view of the microfluidic chip 322 where the second expansion region 329b forms a flat-channel expansion. The microfluidic chip 322 serves a similar purpose as the microfluidic chip 222 except the shape of the expansion and compression regions are different. The microfluidic chip 322 can include a body 325 with at least a first port 321a at a first end and at least a second port 321b at a second end of the body 325. The first port 321a can include an opening 323a that is fluidly connected to a first end of the fluid path of the microfluidic chip 322. The second port 321b can include an opening 323b that is fluidly connected to a second end of the fluid path of the microfluidic chip 322. The fluid path of the microfluidic chip 322 can extend from the opening 323a and the opening 323b. In some embodiments, the fluid path of the microfluidic chip 322 is symmetrical. In other embodiments, the fluid path of the microfluidic chip 322 can be asymmetrical, or a combination of symmetrical and asymmetrical portions. Although the present disclosure discusses the microfluidic chip 322 and the associated fluid path as extending between "first" and "second" ends, the orientation of the microfluidic chip 322 can be interchangeable as the flow within the chip assembly 320 and the microfluidic chip 322 can be bidirectional.

As illustrated in FIGS. 7A-7C, the fluid path of the microfluidic chip 322 can include a plurality of expansion and compression portions. For example, as illustrated, the fluid path of the microfluidic chip 322 can include a first channel 326a, a first expansion portion 327a, a first compression portion 328a, a second expansion region 329, a second compression portion 328b, a third expansion portion 327b, and a second channel 326b.

In some embodiments, the fluid path of the microfluidic chip 322 includes a constricting first channel 326a that is closest to the opening 323a of the first port 321a. The first port 321a can have a length, width, or diameter from between about 0.5 mm to about 4 mm in size. In some embodiments, the length, width, or diameter can be about 0.5 mm, about 1 mm, about 1.5 mm, about 2.0 mm, about 2.5 mm, about 3.0 mm, about 3.5 mm, about 4.0 mm, between about 0.5-1 mm, about 1-1.5 mm, about 1.5-2.0 mm, about 2.5-3.0 mm, about 3.0-3.5 mm, about 3.5-4.0 mm, and any value in between those ranges listed, including endpoints. The first channel 326a can expand and increase in width, height, and/or diameter as the first channel 326a is fluidly connected with the first expansion portion 327a. In some embodiments, the shape of the first expansion portion 327a can be in the shape of a half tear-drop or other arcuate shape. The first expansion portion 327a can have a width, height, and/or diameter that is greater than the first channel 326a. The first expansion portion 327a can range from between about 0.5 mm to about 5 mm. In some embodiments, the length, width, or diameter can be about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.5-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. The first expansion portion 327a can be fluidly connected to a first compression portion 328a. The flow path can constrict in the first compression portion 328a wherein the first compression portion 328a has a smaller width, height, and/or diameter than the first expansion portion 327a. The first compression portion 328a can range from between about 0.3 mm to about 3 mm in width, height and/or diameter. In some embodiments, the length, width, or diameter can be about 0.3 mm, about 0.5 mm, about 1 mm, about 1.5 mm, about 2.0 mm, about 2.5 mm, about 3.0 mm, between about 0.3-1 mm, about 1-1.5 mm, about 1.5-2.0 mm, about 2.5-3.0 mm, and any value in between those ranges listed, including endpoints. The fluid path can expand and increase in width, height, and/or diameter as the first compression portion 328a is fluidly connected with the second expansion region 329. As illustrated in FIG. 7B, the second expansion region 329 is in the shape of a half spherical or elliptical expansion that has a greater length, width, and/or diameter than the first compression portion 328a. The second expansion region 329 can range from between about 0.3 mm to about 5 mm. In some embodiments, the length, width, or diameter can be about 0.3 mm, about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.3-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. As illustrated in FIG. 7C, the second expansion region 329 can be in the shape of a flat-channel expansion. The second expansion region 329 is fluidly connected to the compression portion 328b. The second expansion region 329 can be fluidly connected with the compression portion 328b. The fluid path can constrict at the second compression portion 328b such that the width, height, and/or diameter of the compression portion 328b is less than the width, height, and/or diameter of the second expansion portion 328b. The second compression portion 328b can range from about 0.3 mm to about 3 mm in length, width and/or diameter. In some embodiments, the length, width, or diameter can be about 0.3 mm, about 0.5 mm, about 1 mm, about 1.5 mm, about 2.0 mm, about 2.5 mm, about 3.0 mm, between about 0.3-1 mm, about 1-1.5 mm, about 1.5-2.0 mm, about 2.5-3.0 mm, and any value in between those ranges listed, including endpoints. The second compression portion 328b is fluidly connected to the third expansion portion 327b such that the fluid path expands at the third expansion portion 327b. The third expansion portion 327b can have a width, height, and/or diameter that is greater than the width, height, and/or diameter of the second compression portion 328b. The first expansion portion 327a can range from between about 0.5 mm to about 5 mm. In some embodiments, the length, width, or diameter can be about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.5-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. The third expansion portion 327b can have a three-dimensional half tear-drop shape or other arcuate shape. The third expansion portion 327b can be fluidly connected to constrict at the second channel 326b. The second channel 326b can have a width, height, and/or diameter that is less than the width, height, and/or diameter of the third expansion portion 327b. The second channel 326b can have a size range from about 0.5 mm to about 4 mm in length, width, and/or diameter. In some embodiments, the length, width, or diameter can be about 0.5 mm, about 1 mm, about 1.5 mm, about 2.0 mm, about 2.5 mm, about 3.0 mm, about 3.5 mm, about 4.0 mm, between about 0.5-1 mm, about 1-1.5 mm, about 1.5-2.0 mm, about 2.5-3.0 mm, about 3.0-3.5 mm, about 3.5-4.0 mm, and any value in between those ranges listed, including endpoints. In some embodiments, microfluidic chip 322 is a half-cut design of the microfluidic chip 222. In some examples, the 322 is symmetrical. In other embodiments, the microfluidic chip 322 can be asymmetrical, or a combination of symmetrical and asymmetrical portions. In some embodiments, the ratio between the first channel 326*a* and the expansion portion 327*a* can range between about 1:1 to about 1:10. In some examples, the ratio between the second channel 326*b* and the second channel 326*b* can range between about 1:1 to about 1:10. In some embodiments, the ratio between the compression portion 328*a* or the compression portion 328*b* and the expansion region 329 can range between about 1:1 to about 1:17.

Figures 8A, 8B:
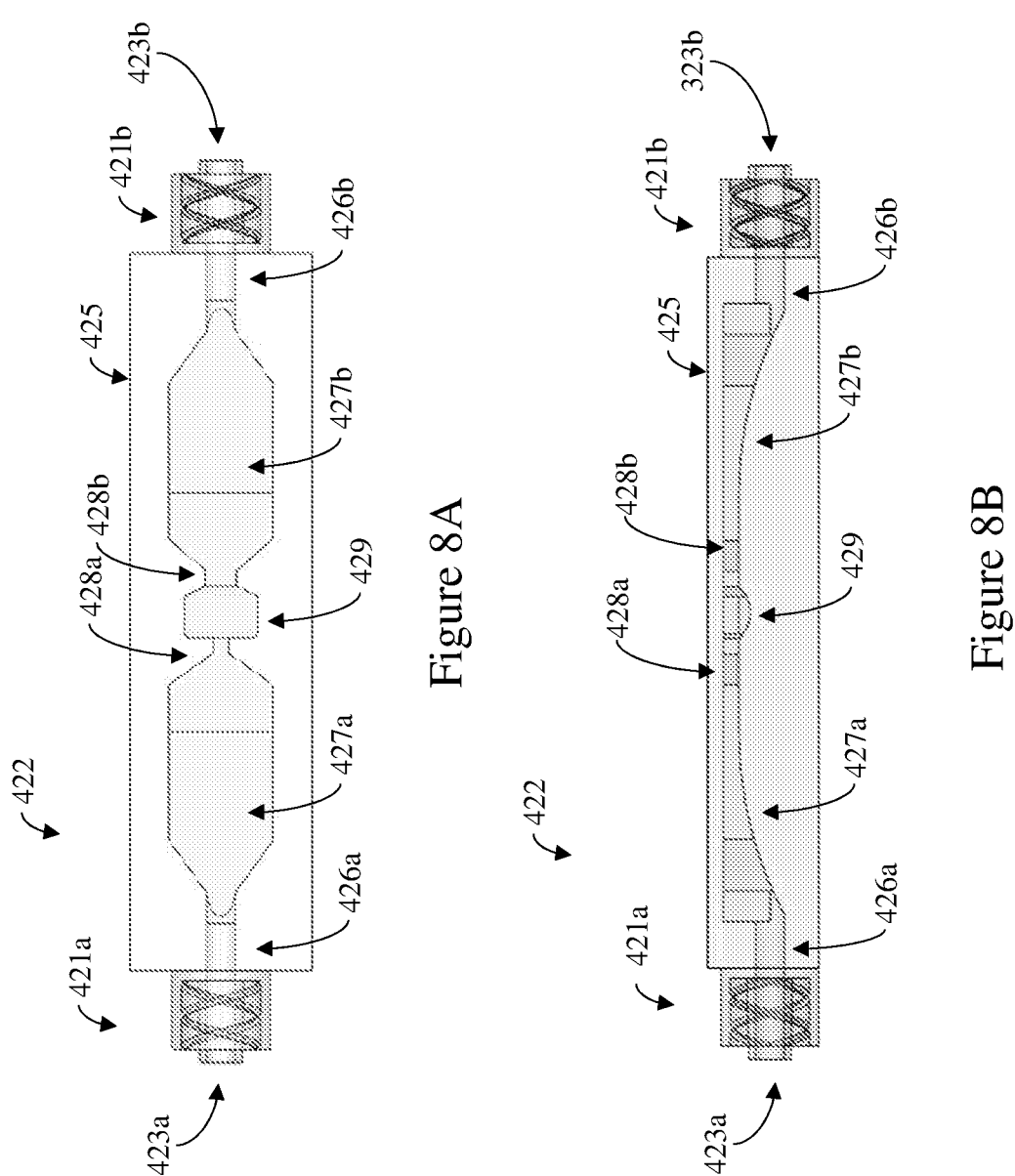
FIGS. 8A-8B illustrate another embodiment of a microfluidic chip configured to be secured in the chip assembly of FIGS. 4A-4B.

FIGS. 8A-8B illustrate another embodiment of a microfluidic chip 422 wherein the fluid path includes a plurality of expansion and compression portions. FIG. 8A illustrates a top view of the microfluidic chip 422 and FIG. 8B illustrates a side view of the microfluidic chip 422. The microfluidic chip 422 serves a similar purpose as the microfluidic chip 222 and microfluidic chip 322 discussed above, except the shapes of the expansion and compression regions of the fluid path differ. The microfluidic chip 422 can include a body 425 with a first port 421*a* at a first end of the microfluidic chip 422 and a second port 421*b* at a second end of the body 425. The first port 421*a* can include an opening 423*a* that is fluidly connected to a first end of the fluid path of the microfluidic chip 422. The second port 421*b* can include an opening 423*b* that is fluidly connected to a second end of the fluid path of the microfluidic chip 422. The fluid path of the microfluidic chip 422 can extend from the opening 423*a* to the opening 423*b*. In some embodiments, the fluid path of the microfluidic chip 422 is symmetrical. In other embodiments, the fluid path of the microfluidic chip 422 can be asymmetrical, or a combination of symmetrical and asymmetrical portions. Although the present disclosure discusses the microfluidic chip 422 and the associated fluid path as extending between "first" and "second" ends, the orientation of the microfluidic chip 422 can be interchangeable as the flow within the chip assembly and the microfluidic chip 422 can be bidirectional.

As illustrated in FIGS. 8A-8B, the fluid path of the microfluidic chip 422 can include a plurality of expansion and compression portions. For example, as illustrated, the fluid path of the microfluidic chip 422 can include a first channel 426*a*, a first expansion portion 427*a*, a first compression portion 428*a*, a second expansion region 429, a second compression portion 428*b*, a third expansion portion 427*b*, and a second channel 426*b*.

In some embodiments, the fluid path of the microfluidic chip 422 includes a constricting first channel 426*a* that is closest to the opening 423*a* of the first port 421*a*. The first port 421*a* can have length, width, and/or diameter from between about 0.5 mm to about 4 mm in size. In some embodiments, the length, width, or diameter can be about 0.5 mm, about 1 mm, about 1.5 mm, about 2.0 mm, about 2.5 mm, about 3.0 mm, about 3.5 mm, about 4.0 mm, between about 0.5-1 mm, about 1-1.5 mm, about 1.5-2.0 mm, about 2.5-3.0 mm, about 3.0-3.5 mm, about 3.5-4.0 mm, and any value in between those ranges listed, including endpoints. The first channel 426*a* can expand and increase in width, height and/or diameter as the first channel 426*a* is fluidly connected with the first expansion portion 427*a*. In some embodiments, the shape of the first expansion portion 427*a* can be in the shape of a half tear-drop. The first expansion portion 427*a* can have a width, height, and/or diameter that is greater than the first channel 426*a*. The first expansion portion 427*a* can range from between about 0.5 mm to about 5 mm. In some embodiments, the length, width, or diameter can be about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.5-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. The first expansion portion 427*a* can be fluidly connected to a first compression portion 428*a*. The flow path can constrict in the first compression portion 428*a* wherein the first compression portion 428*a* has a smaller width, height, and/or diameter than the first expansion portion 427*a*. The first compression portion 428*a* can range from between about 0.3 mm to about 3 mm in width, height and/or diameter. In some embodiments, the length, width, or diameter can be about 0.3 mm, about 0.5 mm, about 1 mm, about 1.5 mm, about 2.0 mm, about 2.5 mm, about 3.0 mm, between about 0.3-1 mm, about 1-1.5 mm, about 1.5-2.0 mm, about 2.5-3.0 mm, and any value in between those ranges listed, including endpoints. The fluid path can expand and increase in width, height, and/or diameter as the first compression portion 428*a* is fluidly connected with the second expansion region 429. As illustrated in FIG. 8A, the second expansion region 429 is D-shaped that has a greater length, width, and/or diameter than the first compression portion 428*a*. The second expansion region 429 can range from between about 0.3 mm to about 5 mm. In some embodiments, the length, width, or diameter can be about 0.3 mm, about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.3-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. As shown in FIG. 8A, the D-shape of the second expansion region 429 has a square end on a first side and an angled second side to provide for more turbulent and vortexing flow. The second expansion region 429 can be fluidly connected with the second compression portion 428*b*. The fluid path can constrict at the second compression portion 428*b* such that the width, height, and/or diameter of the second compression portion 428*b* is less than the width, height, and/or diameter of the second compression portion 428*b*. The second compression portion 428*b* can range from about 0.3 mm to about 3 mm in length, width and/or diameter. In some embodiments, the length, width, or diameter can be about 0.3 mm, about 0.5 mm, about 1 mm, about 1.5 mm, about 2.0 mm, about 2.5 mm, about 3.0 mm, between about 0.3-1 mm, about 1-1.5 mm, about 1.5-2.0 mm, about 2.5-3.0 mm, and any value in between those ranges listed, including endpoints. The second compression portion 428*b* is fluidly connected to the third expansion portion 427*b* such that the fluid path expands at the third expansion portion 427*b*. The third expansion portion 427*b* can have a width, height, and/or diameter that is greater than the width, height, and/or diameter of the second compression portion 428*b*. The third expansion portion 427*b* range from between about 0.5 mm to about 5 mm. In some embodiments, the length, width, or diameter can be about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.5-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. The third expansion portion 427b can have a three-dimensional half tear-drop shape. The third expansion portion 427b can be fluidly connected to constrict at the second channel 426b. The second channel 426b can have a width, height, and/or diameter that is less than the width, height, and/or diameter of the third expansion portion 427b. The second channel 426b can have a size range from about 0.5 mm to about 4 mm in length, width, and/or diameter. In some embodiments, the length, width, or diameter can be about 0.5 mm, about 1 mm, about 1.5 mm, about 2.0 mm, about 2.5 mm, about 3.0 mm, about 3.5 mm, about 4.0 mm, between about 0.5-1 mm, about 1-1.5 mm, about 1.5-2.0 mm, about 2.5-3.0 mm, about 3.0-3.5 mm, about 3.5-4.0 mm, and any value in between those ranges listed, including endpoints. In some embodiments, the microfluidic chip 422 is a half-cut design of the microfluidic chip 222. In some examples, the microfluidic chip 422 is symmetrical. In other embodiments, the microfluidic chip 422 can be asymmetrical, or a combination of symmetrical and asymmetrical portions. In some embodiments, the ratio between the first channel 426a and the first expansion portion 427a can range between about 1:1 to about 1:10. In some examples, the ratio between the second channel 426b and the third expansion portion 427b can range between about 1:1 to about 1:10. In some embodiments, the ratio between the compression portion 428a or the compression portion 428b and the second expansion region 429 can range between about 1:1 to about 1:17.

Figure 9:
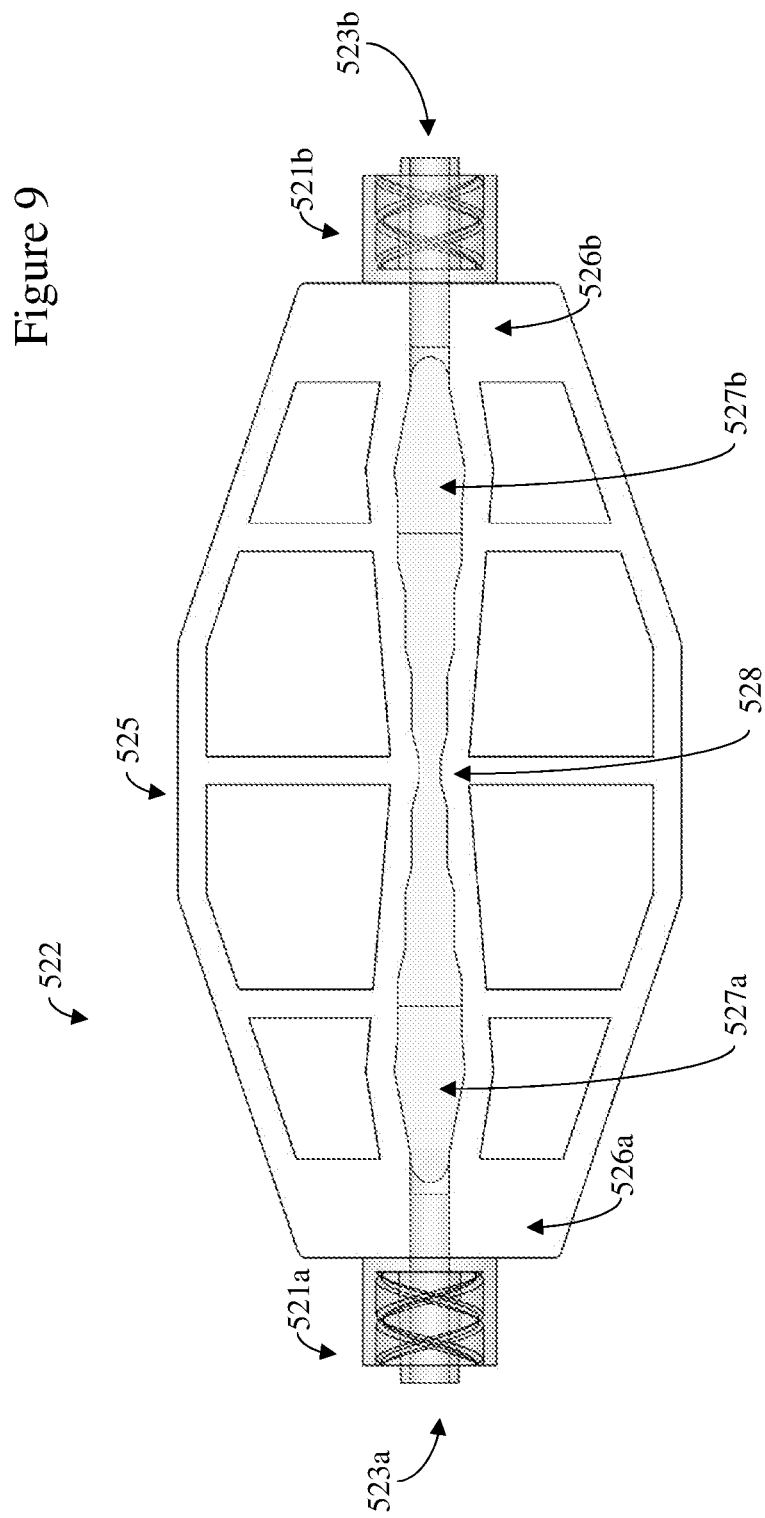
FIG. 9 illustrates another embodiment of a microfluidic chip configured to be secured in the chip assembly of FIGS. 4A-4B.

FIG. 9 illustrates another embodiment of the microfluidic chip 522. As illustrated in FIG. 9, the microfluidic chip 522 includes a fluid path that includes a microfluidic channel formed by a pair of tapered regions that join in a narrowed constriction in a center region of the fluid path. In several embodiments, the tapered regions comprise continuous tapered regions. In some examples, the tapered regions comprise stepped tapered regions. FIG. 9 illustrates a top view of the microfluidic chip 522. The microfluidic chip 522 serves a similar purpose as the microfluidic chip 222, the microfluidic chip 322, and the microfluidic chip 422 discussed above. The microfluidic chip 522 can include a body 525 with a first port 521a at a first end of the microfluidic chip 522 and a second port 521b at a second end of the body 525. The first port 521a can include an opening 523a that is fluidly connected to a first end of the fluid path of the microfluidic chip 522. The second port 521b can include an opening 523b that is fluidly connected to a second end of the fluid path of the microfluidic chip 522. The fluid path of the microfluidic chip 522 can extend from the opening 523a to the opening 523b. In some embodiments, the fluid path of the microfluidic chip 522 is symmetrical. In other embodiments, the fluid path of the microfluidic chip 522 can be asymmetrical, or a combination of symmetrical and asymmetrical portions. Although the present disclosure discusses the microfluidic chip 522 and the associated fluid path as extending between "first" and "second" ends, the orientation of the microfluidic chip 522 can be interchangeable as the flow within the chip assembly and the microfluidic chip 522 can be bidirectional.

As illustrated in FIG. 9, the fluid path of the microfluidic chip 522 can include a plurality of expansion and compression portions. As shown in FIG. 9, the fluid path of the microfluidic chip 522 can include a first channel 526a, a first expansion portion 527a, a compression portion 528, a second expansion portion 527b, and a second channel 526b. As shown in FIG. 9, the fluid path of the microfluidic chip 522 can have an hour-glass shape to provide for a smooth-increase in velocity of the sample. This can help to maintain laminar flow and to slowly increase the shear stress put onto the sample as it interacts with the walls of the device. In some embodiments, the first channel 526a (and the second channel 526b) provides an initial velocity of the fluid to allow for laminar flow. The diamond shape of the first expansion portion 527a (and the second expansion portion 527b) allows for a slowdown of the sample, creating turbulent flow and vortexing to mix the fluid. The compression portion 528 can increase the velocity of the fluid to provide an increase in shear force. The size of the first channel 526a and the second channel 526b can be from about 0.5 mm to about 4 mm in length, width, and/or diameter. In some embodiments, the length, width, or diameter can be about 0.5 mm, about 1 mm, about 1.5 mm, about 2.0 mm, about 2.5 mm, about 3.0 mm, about 3.5 mm, about 4.0 mm, between about 0.5-1 mm, about 1-1.5 mm, about 1.5-2.0 mm, about 2.5-3.0 mm, about 3.0-3.5 mm, about 3.5-4.0 mm, and any value in between those ranges listed, including endpoints. The size of the first expansion portion 527a and the second expansion portion 527b can be larger than the width, length, and/or diameter of the first channel 526a and the second channel 526b. The first expansion portion 527a and the second expansion portion 527b can range from between about 0.3 mm to about 5 mm. In some embodiments, the length, width, or diameter can be about 0.3 mm, about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.3-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. The size of the compression portion 528 can be from about 0.3 mm to about 3 mm. In some embodiments, the length, width, or diameter can be about 0.3 mm, about 0.5 mm, about 1 mm, about 1.5 mm, about 2.0 mm, about 2.5 mm, about 3.0 mm, between about 0.3-1 mm, about 1-1.5 mm, about 1.5-2.0 mm, about 2.5-3.0 mm, and any value in between those ranges listed, including endpoints. In some embodiments the first port 521a and the second port 521b are luer locks. In some embodiments, the first port 521a and the second port 521b can be other luer adapters such as a slip luer. In some embodiments, the ratio between the compression portion 528 and the first expansion portion 527a and/or the ratio between the compression portion 528 and the second expansion portion 527b can range between about 1:1 to about 1:17.

Figure 10:
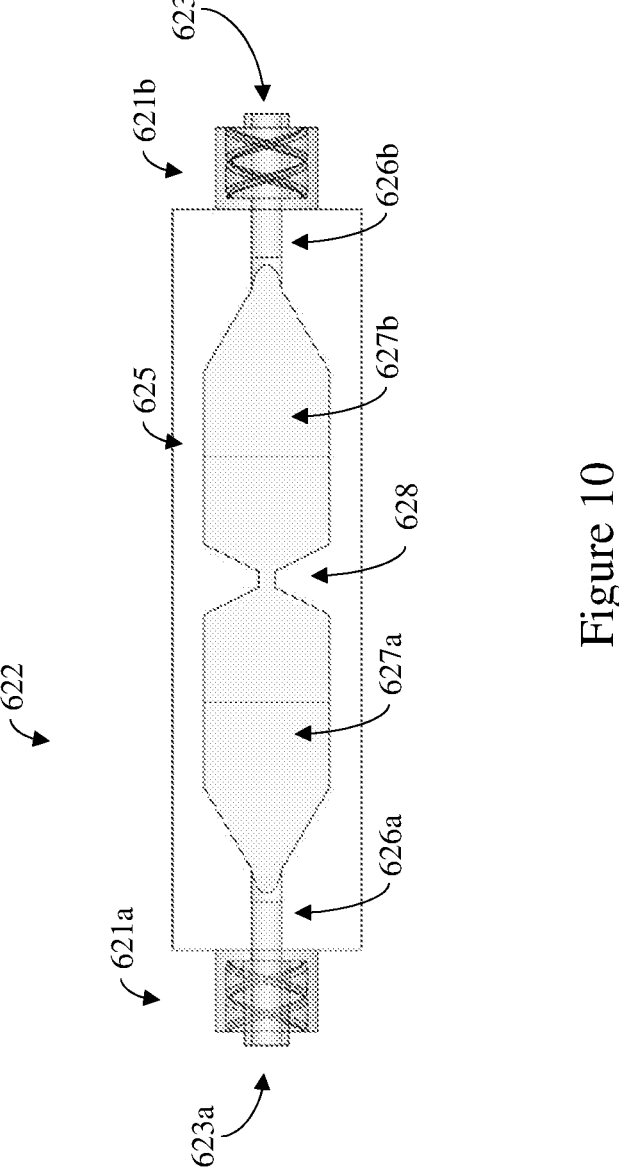
FIG. 10 illustrates another embodiment of a microfluidic chip configured to be secured in the chip assembly of FIGS. 4A-4B.

FIG. 10 illustrates another embodiment of the microfluidic chip 622 wherein the fluid path includes a plurality of expansion and compression portions. FIG. 10 illustrates a top view of the microfluidic chip 622. The microfluidic chip 622 serves a similar purpose as the microfluidic chip 222, microfluidic chip 322, microfluidic chip 422, and microfluidic chip 522 discussed above, except the shapes of the expansion and compression regions of the fluid path differ. The microfluidic chip 622 can include a body 625 with a first port 621a at a first end of the microfluidic chip 622 and a second port 621b at a second end of the body 625. The first port 621a can include an opening 623a that is fluidly connected to a first end of the fluid path of the microfluidic chip 622. The second port 621b can include an opening 623b that is fluidly connected to a second end of the fluid path of the microfluidic chip 622. The fluid path of the microfluidic chip 622 can extend from the opening 623a to the opening 623*b*. In some embodiments, the fluid path of the microfluidic chip 622 is symmetrical. In other embodiments, the fluid path of the microfluidic chip 622 can be asymmetrical, or a combination of symmetrical and asymmetrical portions. Although the present disclosure discusses the microfluidic chip 622 and the associated fluid path as extending between "first" and "second" ends, the orientation of the orientation of the microfluidic chip 622 can be interchangeable as the flow within the chip assembly and the microfluidic chip 622 can be bidirectional.

As illustrated in FIG. 10, the fluid path of the microfluidic chip 622 can include a plurality of expansion and compression portions. For example, as illustrated in FIG. 10, the fluid path of the microfluidic chip 622 can include a first channel 626*a*, a first expansion portion 627*a*, a compression portion 628, a second expansion portion 627*b*, and a second channel 626*b*. The first channel 626*a*, the first expansion portion 627*a*, the compression portion 628, the second expansion portion 627*b*, and the second channel 626*b* are fluidly connected.

In the microfluidic chip 622 illustrated in FIG. 10, the fluid path has a sharper hour-glass shape to provide for increase in turbulent vortexing flow. The first channel 626*a* and the second channel 626*b* can provide an initial velocity of the sample to allow for laminar flow. In some embodiments, the size of the first channel 626*a* and the second channel 626*b* can range from between about 0.5 mm to about 4 mm in length, width, and/or diameter. In some embodiments, the length, width, or diameter can be about 0.5 mm, about 1 mm, about 1.5 mm, about 2.0 mm, about 2.5 mm, about 3.0 mm, about 3.5 mm, about 4.0 mm, between about 0.5-1 mm, about 1-1.5 mm, about 1.5-2.0 mm, about 2.5-3.0 mm, about 3.0-3.5 mm, about 3.5-4.0 mm, and any value in between those ranges listed, including endpoints. The first expansion portion 627*a* and the second expansion portion 627*b* can have a diamond shape that provides a slowdown of the fluid. This can create turbulent flow and vortexing to mix the fluid sample. In some embodiments, the size of the first diamond expansion portion 627*a* and the second diamond expansion portion 627*b* is larger than the width, length and/or diameter of the first channel 626*a* and the second channel 626*b*. The first expansion portion 627*a* and the second expansion portion 627*b* can range from between about 0.3 mm to about 5 mm. In some embodiments, the length, width, or diameter can be about 0.3 mm, about 0.5 mm, about 1 mm, about 1.5 mm, about 2.0 mm, about 2.5 mm, about 3.0 mm, about 3.5 mm, about 4.0 mm, about 4.5 mm, about 5.0 mm, between about 0.3-1 mm, about 1-1.5 mm, about 1.5-2.0 mm, about 2.5-3.0 mm, about 3.0-3.5 mm, about 3.5-4.0 mm, about 4.0-4.5 mm, about 4.5-5.0 mm and any value in between those ranges listed, including endpoints. The compression portion 628 can increase the velocity of the sample to increase the shear force applied to the fluid sample. As well, the sharp angles on either side of the compression portion 628 can provide turbulent and vortexing flow. In some embodiments, the compression portion 628 can range from between about 0.3 mm to about 3 mm in width, length, and/or diameter. In some embodiments, the length, width, or diameter can be about 0.3 mm, about 0.5 mm, about 1 mm, about 1.5 mm, about 2.0 mm, about 2.5 mm, about 3.0 mm, between about 0.3-1 mm, about 1-1.5 mm, about 1.5-2.0 mm, about 2.5-3.0 mm, and any value in between those ranges listed, including endpoints. In some embodiments, the first port 621*a* and the second port 621*b* are luer locks. In some embodiments, the first port 621*a* and the second port 621*b* can be other luer adapters such as a slip luer. In some embodiments, the ratio between the compression portion 628 and the expansion portion 627*a* and/or the ratio between the compression portion 628 and the expansion portion 627*b* can range between about 1:1 to about 1:17.

FIGS. 11A-11B, 12A-12B, and 13A-13B illustrate a plurality of embodiments of microfluidic chips with a three-dimensional channel design. The three-dimensional channel design of FIGS. 11A-11B, 12A-12B, and 13A-13B have fluid paths that compresses/contracts and expands in a plurality of stages. This compression and expansion can allow for the creation of turbulent flow which assists in the processing of biological samples. For example, the devices can be used to break down adipose tissue mechanically in order to micronize the size of the adipose tissue down for applications such as orthopedic surgery, arthroscopic surgery, neurosurgery, gastrointestinal and affiliated organ surgery, urological surgery, general surgery, gynecological surgery, thoracic surgery, laparoscopic surgery, and plastic and reconstructive surgery, etc. The described microfluidic chips can be manufactured using any of 3D (three dimensional) printing, additive manufacturing, subtractive manufacturing, or injection molding. The materials used to print or manufacture the device can be biocompatible and sterilizable. The microfluidic chip can incorporate an inlet and outlet which can be a luer lock, a screw, or any form that allows for a fluidic seal. Once the seal is formed, a fluidic pathway is created. As the sample passes through the inlet, it interacts with a compression region which is smaller than the diameter of the inlet and thus creates mechanical stress. The diameter of this region can range from between about 0.5 mm to about 3.0 mm. In some embodiments, the length, width, or diameter can be about 0.5 mm, about 1 mm, about 1.5 mm, about 2.0 mm, about 2.5 mm, about 3.0 mm, between about 0.5-1 mm, about 1-1.5 mm, about 1.5-2.0 mm, about 2.5-3.0 mm, and any value in between those ranges listed, including endpoints. After passing through the compression region, the pathway expands into an expansion region. In some embodiments, the expansion region can create turbulent flow and vortexing. In some examples, the expansion region can provide controlled and precise laminar flow. The diameter of the expansion region can range between about 4 mm to about 25 mm. In some embodiments, the diameter of the expansion region can range between about 4 mm, about 6 mm, about 8 mm, about 10 mm, about 12 mm, about 14 mm, about 16 mm, about 18 mm, about 20 mm, about 22 mm, about 24 mm, about 25 mm, between about 4-6 mm, about 6-8 mm, about 8-10 mm, about 10-12 mm, about 12-14 mm, about 14-16 mm, about 16-18 mm, about 18-20 mm, about 20-22 mm, about 22-24 mm, about 24-25 mm, and any value in between those ranges listed, including endpoints. After passing through the expansion region, the subsequent contraction region provides significant shear stress on the samples being processed. As mentioned above, the diameter of the compression region can range from between about 0.5 mm to about 3.0 mm. In some embodiments, the length, width, or diameter can be about 0.5 mm, about 1 mm, about 1.5 mm, about 2.0 mm, about 2.5 mm, about 3.0 mm, between about 0.5-1 mm, about 1-1.5 mm, about 1.5-2.0 mm, about 2.5-3.0 mm, and any value in between those ranges listed, including endpoints. In some embodiments, the shape of the expansion and constriction regions along with the overall design may be circular, elliptical, square, and rectangular although other shapes can be used.

Figures 11A, 11B:
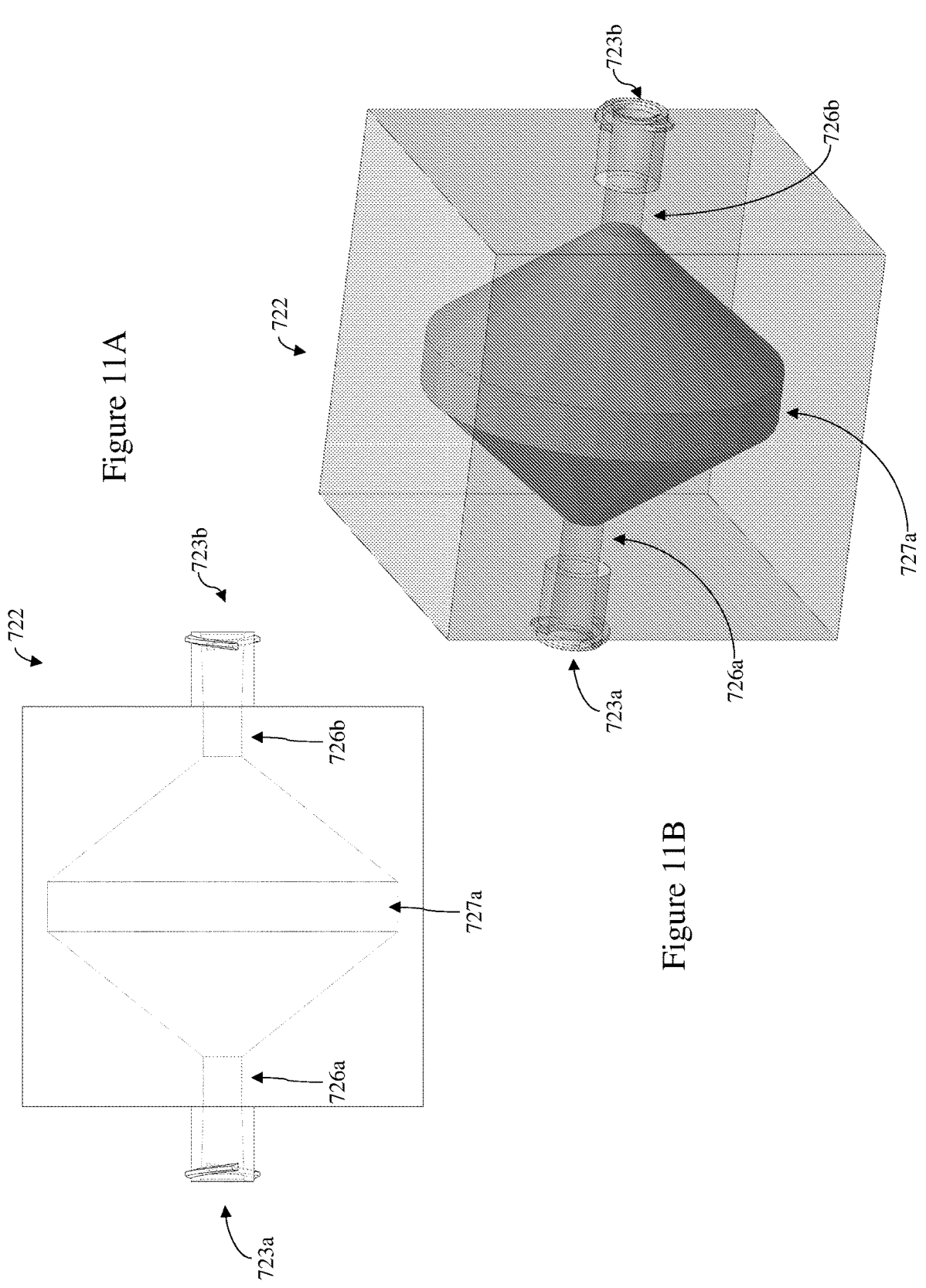
FIGS. 11A-11B, 12A-12B, and 13A-13B illustrate various embodiments of three-dimensional channels in a microfluidic chip with expanded and compressed regions.

FIGS. 11A-11B illustrates an embodiment of the microfluidic chip 722 with a single expansion region. FIG. 11A illustrates a side view of the microfluidic chip 722 and FIG.

11B illustrates a perspective view of the microfluidic chip 722. The flow of fluid through the fluidic path of the microfluidic chip 722 is described above in more detail. The microfluidic chip 722 includes a first port 721*a* at a first end of the microfluidic chip 722 and a second port 721*b* at a second end of the microfluidic chip 722. The first port 721*a* can include an opening 723*a* that is fluidly connected to a first end of the fluid path of the microfluidic chip 722. The second port 721*b* can include an opening 723*b* that is fluidly connected to a second end of the fluid path of the micro-fluidic chip 722. The fluid path of the microfluidic chip 722 can extend from the opening 723*a* to the opening 723*b*. In some embodiments, the fluid path of the microfluidic chip 722 is symmetrical. As illustrated in FIGS. 11A-11B, the fluid path of the microfluidic chip 722 can include a first channel 726*a*, an expansion portion 727*a*, and a second channel 726*b* that are fluidly connected. As discussed above, at the first channel 726*a* and the second channel 726*b*, the fluid sample can experience significant shear stress. At the expansion portion 727*a*, the fluid sample can experience turbulent flow and vortexing. In some embodiments, the ratio between the first channel 726*a* and the expansion portion 727*a* and/or the ratio between the second channel 726*b* and the expansion portion 727*a* ranges between about 1:1 to about 1:83.

Figures 12A, 12B:
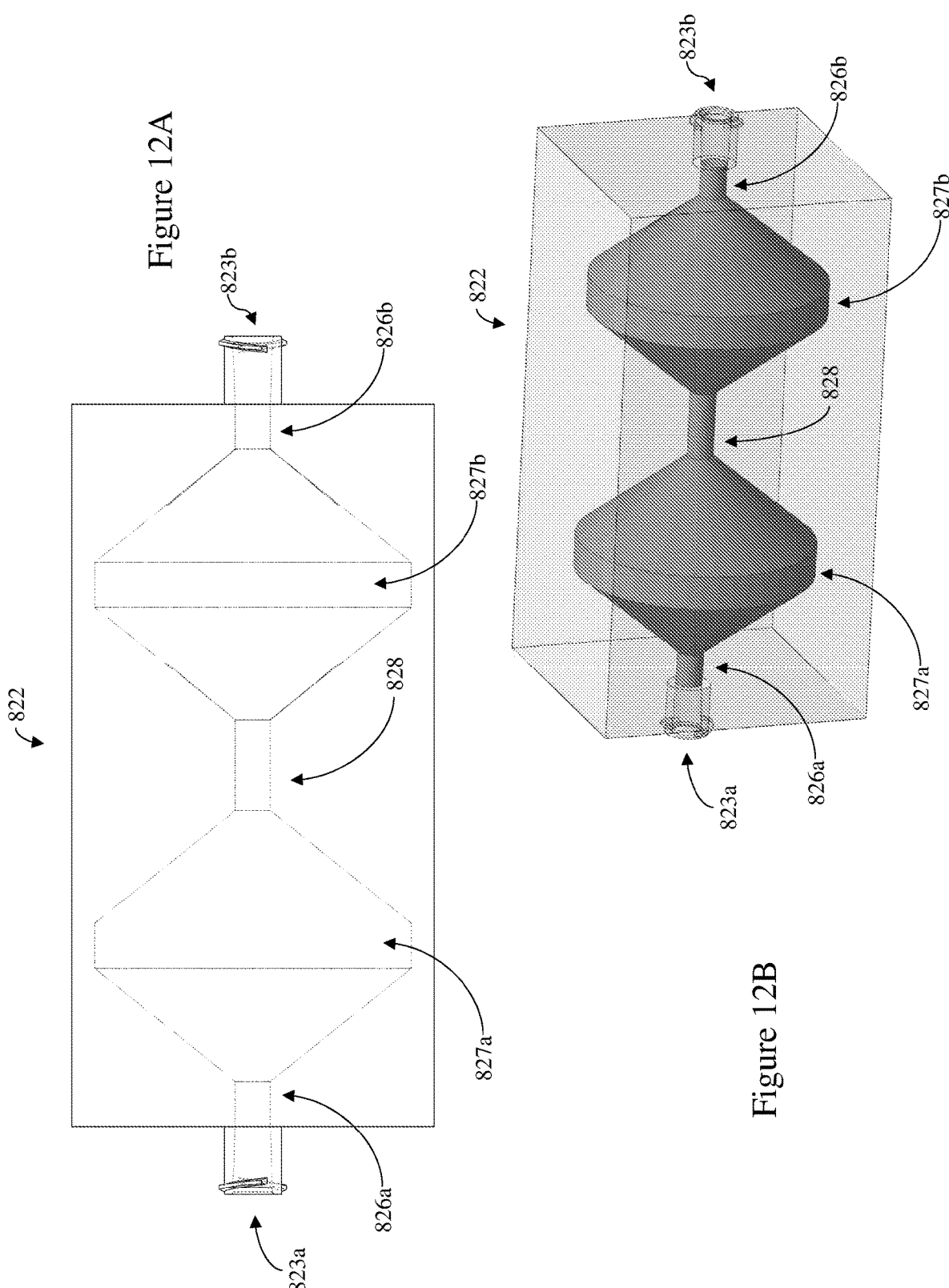

FIGS. 12A-12B illustrates an embodiment of the micro-fluidic chip 822 with two expansion regions and a compression region between the two expansion regions. FIG. 12A illustrates a side view of the microfluidic chip 822 and FIG. 12B illustrates a perspective view of the microfluidic chip 822. The flow of fluid through the fluidic path of the microfluidic chip 822 is described above in more detail. The microfluidic chip 822 can include a first port 821*a* at a first end of the microfluidic chip 822 and a second port 821*b* at a second end of the microfluidic chip 822. The first port 821*a* can include an opening 823*a* that is fluidly connected to a first end of the fluid path of the microfluidic chip 822. The second port 821*b* can include an opening 823*b* that is fluidly connected to a second end of the fluid path of the micro-fluidic chip 822. The fluid path of the microfluidic chip 822 can extend from the opening 823*a* to the opening 823*b*. In some embodiments, the fluid path of the microfluidic chip 822 is symmetrical. As illustrated in FIGS. 12A-12B, the fluid path of the microfluidic chip 822 can include a first channel 826*a*, a first expansion portion 827*a*, a compression portion 828, a second expansion portion 827*b*, and a second channel 826*b* that are fluidly connected. As discussed above, the fluid sample at the first channel 826*a*, the compression portion 828, and the second channel 826*b*, can experience significant shear stress. At the first expansion portion 827*a* and the expansion portion 827*b*, the fluid sample can experience turbulent flow and vortexing. In some embodiments, the ratio between the channels 826*a*, 826*b* and the expansion portions 827*a*, 827*b* can range between about 1:1 to about 1:83. In some examples, the ratio between the compression portion 828 and the expansion portions 827*a*, 827*b* can range between about 1:1 to about 1:83.

Figures 13A, 13B:
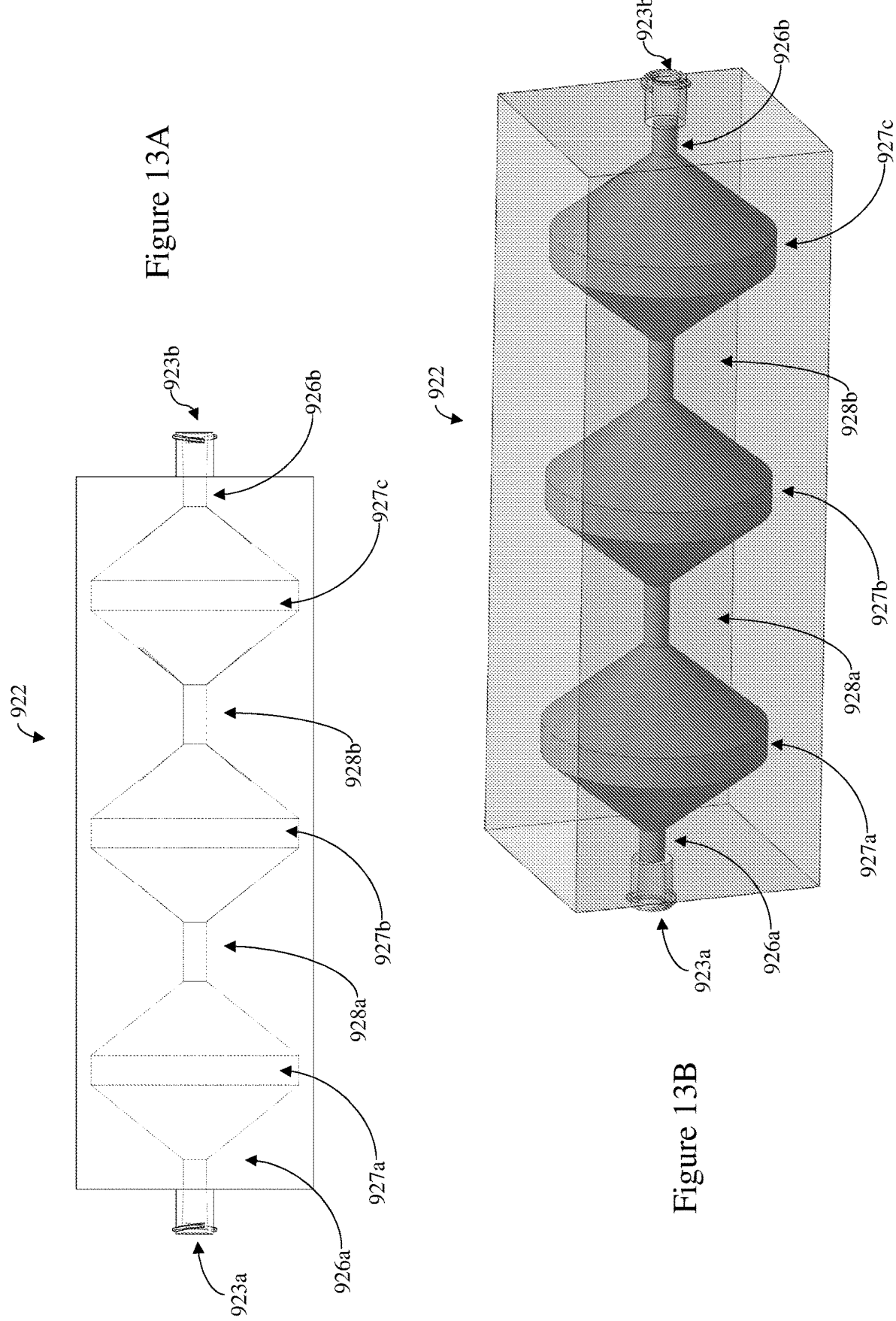

FIGS. 13A-13B illustrates an embodiment of the micro-fluidic chip 922 with three expansion regions and two compression regions between the three expansion regions. FIG. 13A illustrates a side view of the microfluidic chip 922 and FIG. 13B illustrates a perspective view of the micro-fluidic chip 922. The flow of fluid through the fluidic path of the microfluidic chip 922 is described above in more detail. The microfluidic chip 922 can include a first port 921*a* at a first end of the microfluidic chip 922 and a second port 921*b* at a second end of the microfluidic chip 922. The first port 921*a* can include an opening 923*a* that is fluidly connected to a first end of the fluid path of the microfluidic chip 922. The second port 921*b* can include an opening 923*b* that is fluidly connected to a second end of the fluid path of the microfluidic chip 922. The fluid path of the microfluidic chip 922 can extend from the opening 923*a* to the opening 923*b*. In some embodiments, the fluid path of the microfluidic chip 922 is symmetrical. As illustrated in FIGS. 13A-13B, the fluid path of the microfluidic chip 922 can include a first channel 926*a*, a first expansion portion 927*a*, a first compression portion 928*a*, a second expansion portion 927*b*, a second compression portion 928*b*, a third expansion portion 927*c*, and a expansion portion 927*c* that are fluidly connected. As discussed above, the fluid sample at the first channel 926*a*, the first compression portion 928*a*, the second compression portion 928*b*, and the second channel 926*b* can experience significant shear stress. At the first expansion portion 927*a*, the second expansion portion 927*b*, and the third expansion portion 927*c*, the fluid sample can experience turbulent flow and vortexing. In some embodiments, the ratio between the channels 926*a*. 926*b* and the expansion portions 927*a*, 927*b*, 927*c* can range between about 1:1 to about 1:83. In some examples, the ratio between the compression portions 928*a*. 928*b* and the expansion portions 927*a*, 927*b*, 927*c* can range between about 1:1 to about 1:83.

The examples of microfluidic chips illustrated in FIGS. 11A-11B, 12A-12B, and 13A-13B are intended to be exemplary and non-limiting. A microfluidic chip can include any number of expansion and/or compression regions to achieve the intended result.

Sample Chamber

Figure 14B:
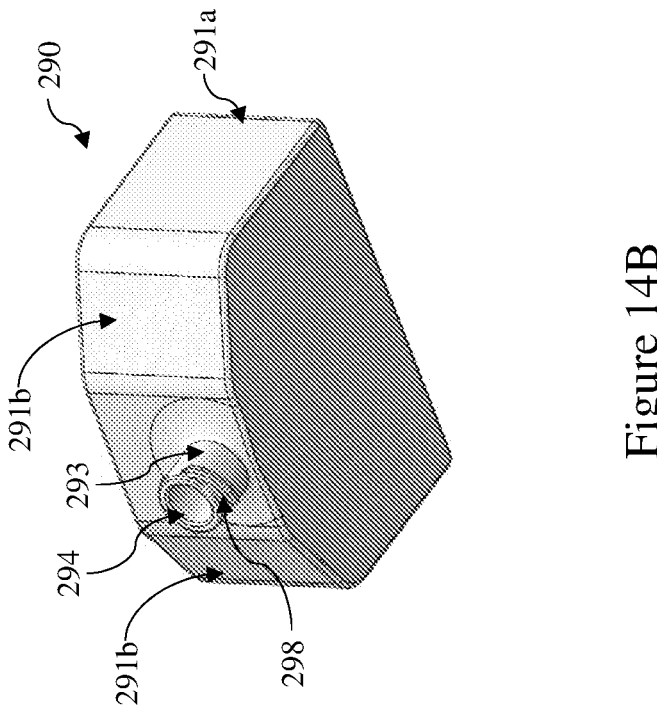
FIGS. 14A-14F illustrate an embodiment of a sample chamber configured to be secured to a microfluidic chip.
Figure 14A:
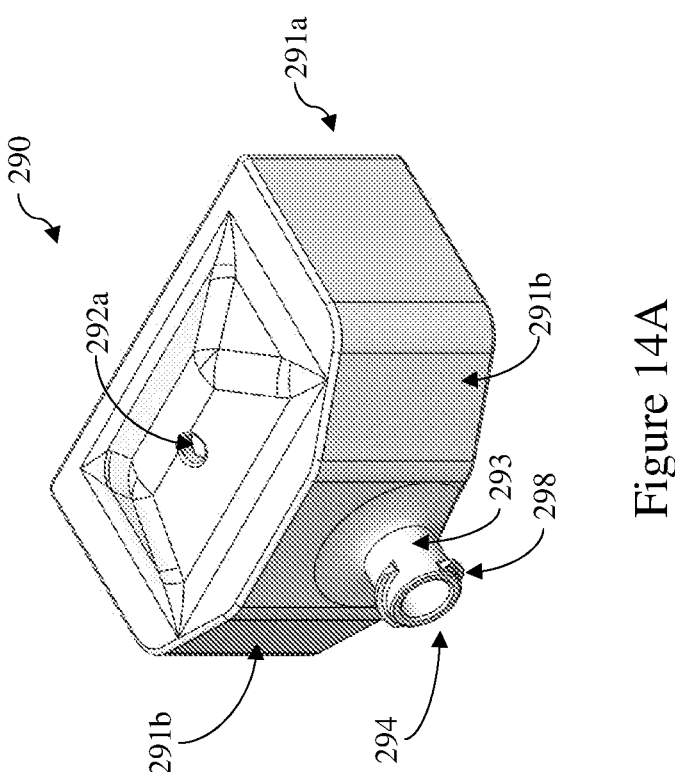

FIGS. 14A-14B illustrates a sample chamber 290 that can hold a sample during processing, or for storage before or after processing (e.g., during transport). The sample chamber 290 can include a body 291*a* with a port 293 positioned a first end of the body 291*a*. The port 293 of the sample chamber 290 can form a luer lock connector to connect to a syringe for injection and extraction of a sample. The port 293 can also fluidly connect with a microfluidic chip 222. As illustrated in FIGS. 4A-4B, the port 293 of the sample chamber 290 can include an engagement surface 298 that is configured to engage with either the first port 221*a* or the second port 221*b* of the microfluidic chip 222. The port 293 of the sample chamber 290 can include an opening 294 that allows for the sample to flow into or out of the sample chamber 290. The size of the opening 294 can range from between about 0.5 mm to about 3 mm in diameter. In some embodiments, the length, width, or diameter can be about 0.5 mm, about 1 mm, about 1.5 mm, about 2.0 mm, about 2.5 mm, about 3.0 mm, between about 0.5-1 mm, about 1-1.5 mm, about 1.5-2.0 mm, about 2.5-3.0 mm, and any value in between those ranges listed, including endpoints. The port 293 can also be a different type of luer connector like a slip luer. As shown in FIG. 14A, the port 293 of the sample chamber 290 can be positioned near a bottom of the sample chamber 290 to allow easy flow of fluid into the microfluidic chip 222. In some embodiments, the port 293 can be positioned higher on the sample chamber 290. As shown in FIG. 14A, the sample chamber 290 can include a vent hole 292*a* on a top of the sample chamber 290 to allow for smooth fluid flow when the chip and chamber are fully assembled, and to prevent a vacuum from forming inside the sample chamber 290 and the fluidly connected microfluidic chip 222. The body 291*a* of the sample chamber 290 can include a tapered surface 291*b* and a tapered surface 291*b* positioned on either side of the port 293. In some embodiments, the tapered surface 291*b* and the 29*b* can provide smoother flow and full evacuation of the fluid sample inside the sample chamber 290 during centrifugation and extraction. In some embodiments, the tapered surface 291b can have an angle greater than 25 degrees from the front face of the chamber.

Figures 14C, 14D, 14E, 14F:
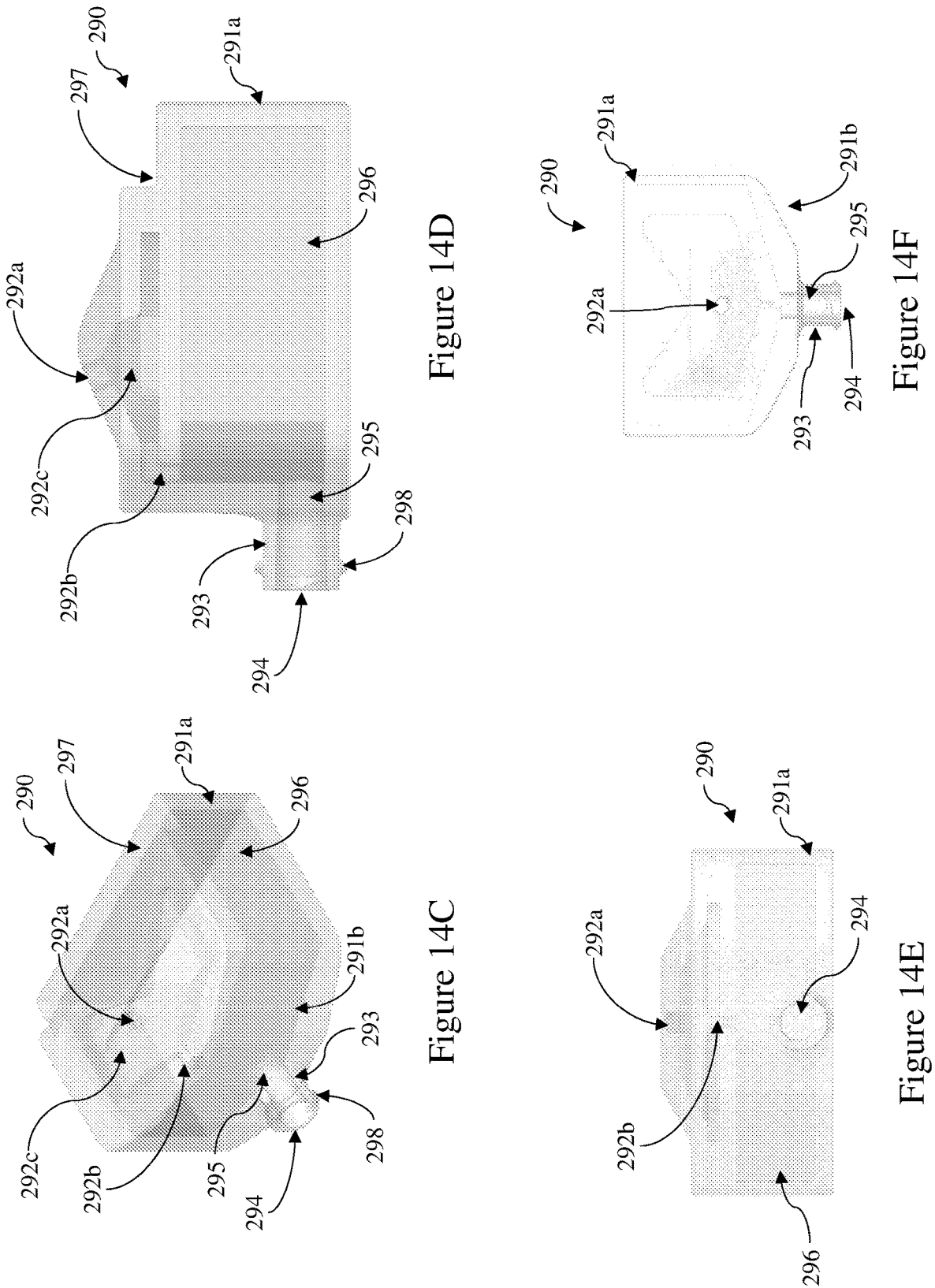

FIGS. 14C-14D illustrate an interview of the sample chamber 290. The sample chamber 290 includes a holding cavity 296 that is fluidly connected to a vent channel 292b, a vent chamber 292c, and the vent hole 292a. The internal holding cavity 296 can hold a sample during use. The volume of the holding cavity 296 can range from about 1 mL to about 300 mL. The sample chamber 290 can include an arrow-shaped vent chamber 292c at a top portion of the sample chamber 290. The vent chamber 292c can catch any sample that gets into the vent channel, and prevent it from coming out of the sample chamber 290. During use, the fluid sample in the vent chamber 292c experiences centrifugal force. The arrow shape of the vent chamber 292c causes the fluid sample, during use, to be pushed into the corners of the vent chamber 292c and away from the vent hole 292a on top. When the direction of the centrifugal force is reversed, the fluid sample can be pushed back into the holding cavity 296 through the vent channel 292b. The volume of the vent chamber 292c can range between about 0.5 mL to about 50 mL. In some embodiments, a luer adapter can be added to the back of the chamber as an alternative extraction and filling point. In some embodiments, the sample chamber 290 can include a carriage adapting ridge 297 that can be added to be secured to and engage a portion of the carriage.

Filter

Figures 15A, 15B:
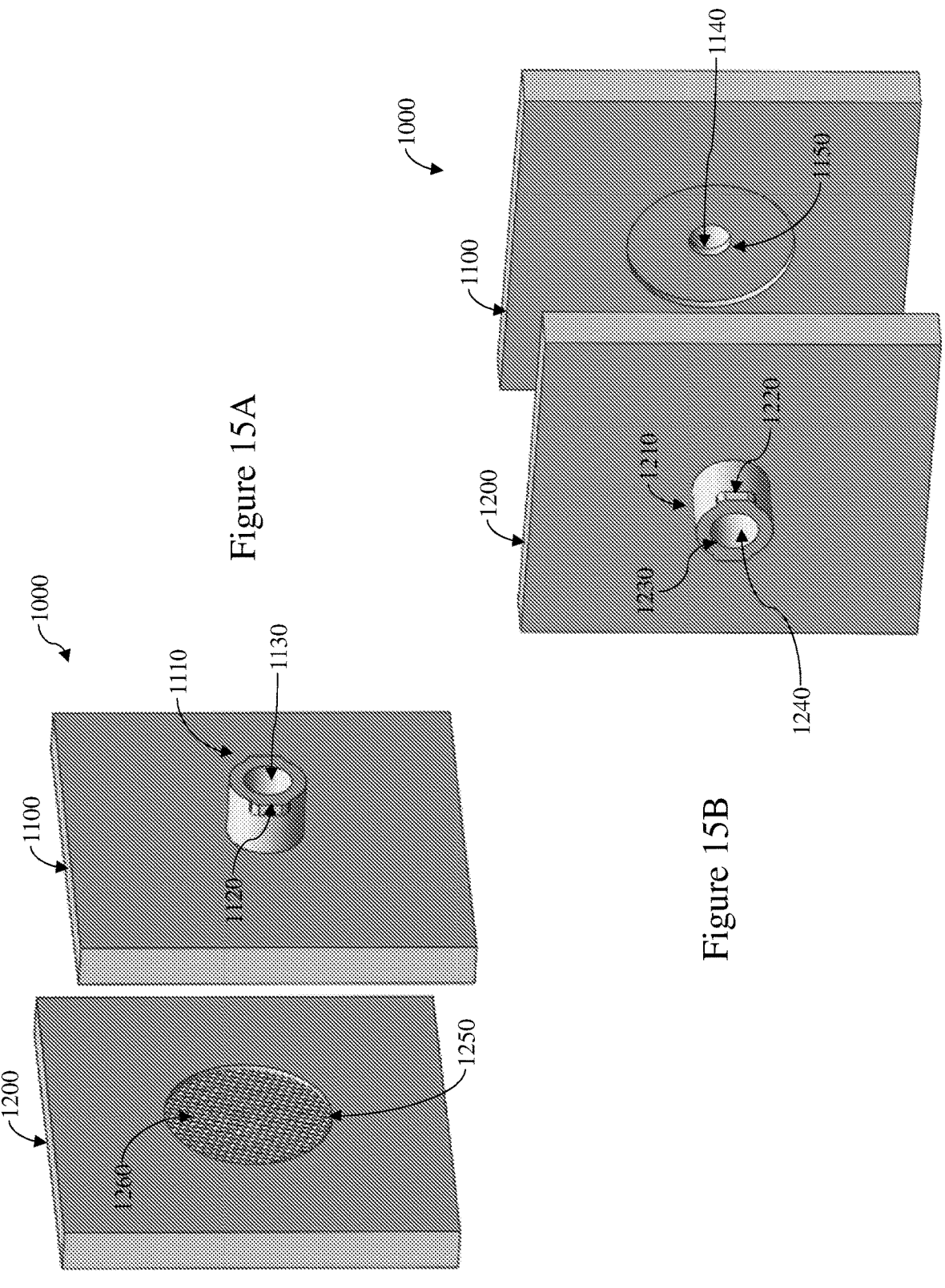
FIGS. 15A-15B illustrate an embodiment of a filter.
Figures 16A, 16B:
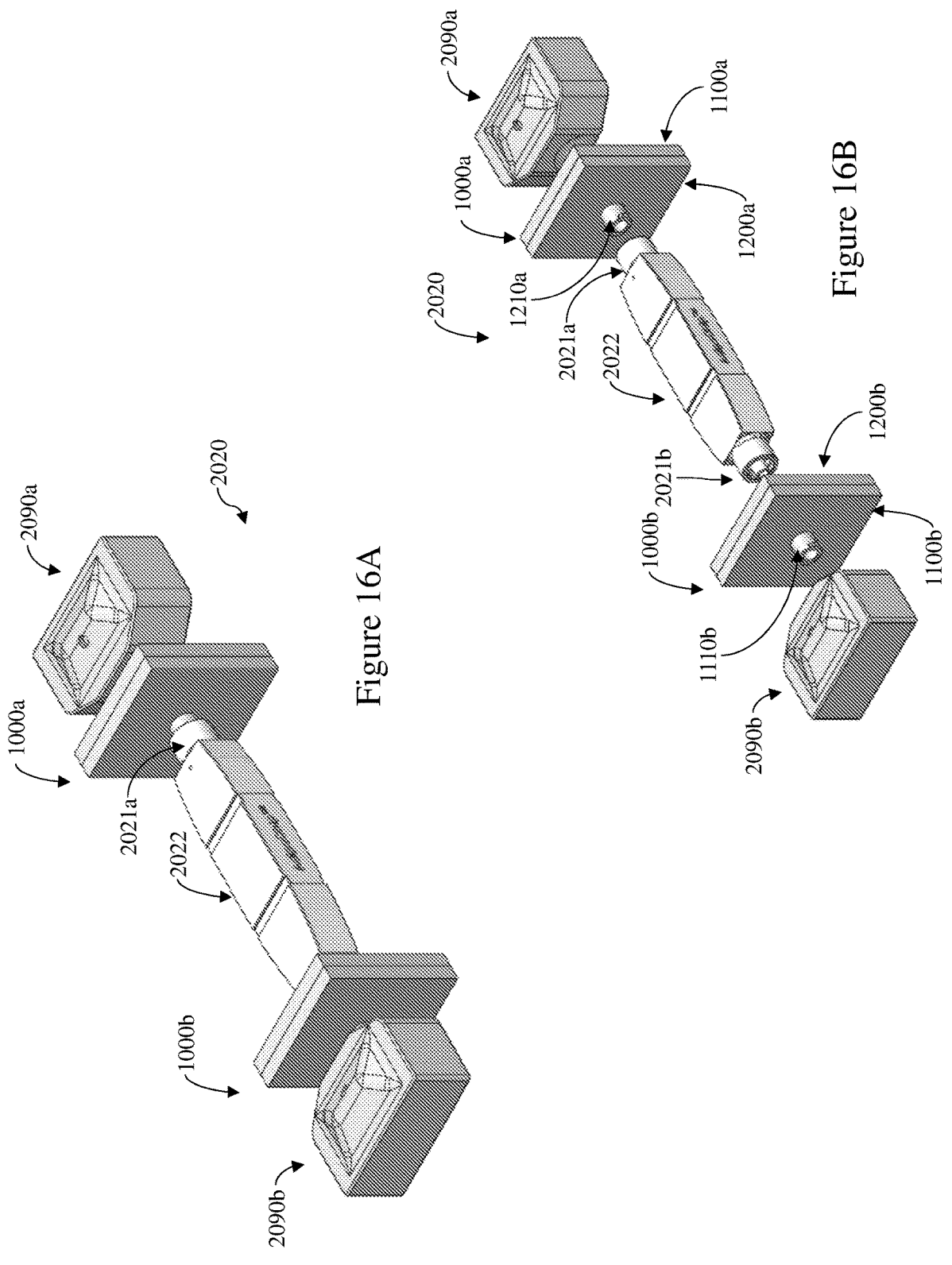
FIGS. 16A-16B illustrate the filter of FIGS. 15A-15B configured to be secured in a chip assembly.

FIGS. 15A-15B illustrates an embodiment of a filter that can be positioned between a sample chamber and a microfluidic chip in a chip assembly. As illustrated in FIGS. 16A-16B, the filter can be located upstream of or before the microfluidic chip to filter the sample to prevent clogging of the microfluidic chip. As will be discussed in more detail below, the filter can include a mesh that is configured to cut or Micronizing tissue or tissue fragments to allow the sample to pass through the microfluidic chip without clogging is performed in several embodiments. The cutting or micronization of the sample can produce macroscopic aggregates for the purpose of microfluidic shearing in the microfluidic chips. As illustrated in FIGS. 16A-16B, the filter can be located downstream of or after the microfluidic chip to only allow a certain sized sample to pass out of the device for collection.

FIGS. 15A-15B illustrates an embodiment of the filter 1000. The filter 1000 can include a first body portion 1100 and a second body portion 1200. The first body portion 1100 can include a first side with a port 1110. The port 1110 can include an engagement surface 1120 that is configured to engage with either the first or second port of any of the disclosed microfluidic chips. The engagement surface 1120 of the port 1110 can be configured to engage the port (i.e., port 293) of the sample chamber 290. The port 1110 can include a channel 1140 that extends from the first opening 1130 on the first side of the first body portion 1100 to a second opening 1150 on a second side of the first body portion 1100.

The second body portion 1200 can include a first side with a port 1210. The port 1210 can include an engagement surface 1220 that is configured to engage with either the first or second port of any of the disclosed microfluidic chips. The engagement surface 1120 of the port 1110 can be configured to engage the port (i.e., port 293) of the sample chamber 290. The port 1210 can include a channel 1240 that extends from the first opening 1230 on the first side of the second body portion 1200 to a second opening 1250 on a second side of the second body portion 1200. As shown in FIG. 15A, the second side of the second body portion 1200 can include a mesh filter 1260. As discussed above, the mesh filter 1260 can filter the sample to prevent clogging of the microfluidic chip and/or to ensure that only a certain sized sample is passed out of the microfluidic chip for collection. In some embodiments, the filters 1260 can have a mesh size ranging from about 1 μm to about 2000 μm, between about 1 μm to about 100 μm, about 100 μm to about 200 μm, about 200 μm to about 300 μm, about 300 μm to about 400 μm, about 400 μm to about 500 μm, about 500 μm to about 600 μm, about 600 μm to about 700 μm, about 700 μm to about 800 μm, about 800 μm to about 900 μm, about 900 μm to about 1000 μm, about 1000 μm to about 1100 μm, about 1100 μm to about 1200 μm, about 1200 μm to about 1300 μm, about 1300 μm to about 1400 μm, about 1400 μm to about 1500 μm, about 1500 μm to about 1600 μm, about 1600 μm to about 1700 μm, about 1700 μm to about 1800 μm, about 1800 μm to about 1900 μm, about 1900 to about 2000 μm, and any value in between those ranges listed, including endpoints.

FIGS. 16A-16B illustrates a view of the chip assembly 2020 with a first filter 1000a and a second filter 1000b on either end of the microfluidic chip 2022. FIG. 16B illustrates an exploded view of the chip assembly 2020. As shown in FIG. 16B, in some embodiments, the filter 1000a can be positioned such that the port 1110a of the first body portion 1100a is fluidly connected to the sample chamber 2090a and the port 1210a of the second body portion 1200a is fluidly connected with a first port 2021a of the microfluidic chip 2022. As shown in FIG. 16B, the filter 1000b can be positioned such that the port 1110b of the first body portion 1100b is fluidly connected to the sample chamber 2090b and the port 1210b of the second body portion 1200b is fluidly connected with a second port 2021b of the microfluidic chip 2022. However, FIGS. 16A-16B illustrates only one orientation of the filters 1000a, 1000b on the chip assembly 2020. In some embodiments, the filter 1000 can be oriented such that the port 1110 of the first body portion 1100 is connected to the port of the sample chamber and the port 1210 of the second body portion 1200 is connected to the port of the microfluidic chip on one or both of the filters 1000. In some embodiments the filter 1000 can be oriented such that the port 1210 of the second body portion 1200 is connected to the port of the sample chamber and the port 1110 of the first body portion 1100 is connected to the port of the microfluidic chip on one or both of the filters 1000. In some embodiments, the chip assembly 2020 can include a filter 1000 at only one or on both ends of the microfluidic chip 2022.

The filter 1000 can be manufactured using a variety of methods such as through: additive manufacturing, subtractive manufacturing, 3D printing, injection molding, resin molding, or urethane casting. The filter 1000 can be made from a variety of materials such as plastic (e.g., polycarbonate, acrylic, etc.), polyurethane, or metal (e.g., aluminum, steel, stainless steel, surgical steel, brass, copper, etc).

Carriage

As discussed above, the carriage 230 can include a base platform 250, a spring platform 240, and a clamp 210. The assembly of the carriage 230 is discussed in more detail above with regard to FIGS. 3A-3B.

Figures 17A, 17B:
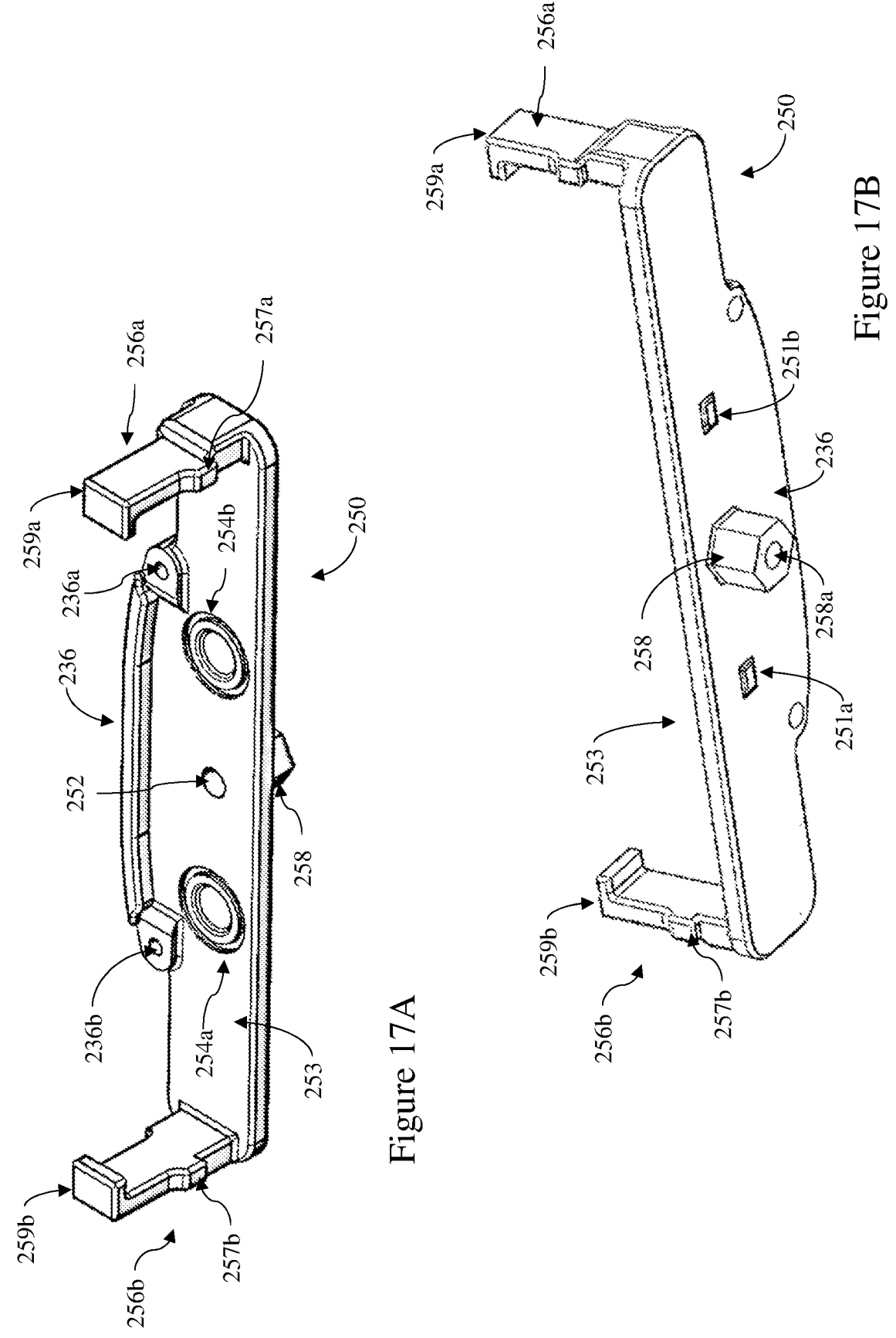
FIGS. 17A-17B illustrate an embodiment of a base platform of the carriage assembly of FIGS. 3A-3B.

FIGS. 17A-17B illustrate an embodiment of the base platform 250. The base platform 250 can include a raised wall at one or both ends of the base. As shown in FIGS. 17A-17B, the base platform 250 can include a first arm 256a and a second arm 256b that are configured to engage with mating portions on the spring platform 240. In some embodiments, the first arm 256a and the second arm 256b can slide into a corresponding gap in the body 253 of the base platform 250. Each of the first arm 256a and the second arm 256b can include a mating slot 257a and mating slot 257b on a side portion of the first arm 256a and second arm 256b respectively. Each of the first arm 256a and the second arm 256b can also include a retention lip 259a and a retention lip 259b respectively on a top portion to secure a chip assembly 220 on the carriage. On a top surface of a body 253 of the base platform 250, the body 253 includes a distal spring holder 254a and a distal spring holder 254b to retain a base portion of a spring. The body 253 also includes a shoulder 236 that is configured to engage the clamp 210. The body 253 includes a first opening 236a and a second opening 236b that is configured to receive a screw to secure the clamp 210 to the base platform 250. A bottom surface of the body 253 of the base platform 250 can include a post 258 with a through hole that extends between a distal opening 258a and an opening 252. The bottom surface of the body 253 also includes a plurality of pedestals (i.e., pedestal 251a and pedestal 251b. The post 258 and the pedestals (i.e., pedestal 251a and the pedestal 251b) are configured to reversibly interact and retain the carriage 230 to one of the lateral arms 263 of the base 260. The base platform 250 can be manufactured using a variety of methods such as through: additive manufacturing, subtractive manufacturing, injection molding, resin molding, or urethane casting. The base platform 250 can be made from a variety of materials such as plastic (e.g., polycarbonate, acrylic, etc.), polyurethane, or metal (e.g., aluminum, steel, stainless steel, surgical steel, brass, copper, etc.).

As shown in FIG. 2B, the bottom surface of the base platform 250 can include a plurality of capture elements that serve to hold the carriage 230 in a desired position until such time as there is a signal (or force, or lackthereof) that allows the capture elements to disengage or otherwise cease interaction with the release element, which subsequently allows rotation of the carriage 230, to be followed be a reengagement of the capture element in order to stop the motion of the carriage 230. In some embodiments, this can allow rotation of the carriage 230 through an arc of 180 degrees at a desired time in a tissue processing protocol. In some examples, the capture elements comprise magnets of a first polarity and the release element comprises a magnet of an opposite polarity.

In the embodiment illustrated in FIG. 2B, the capture elements are a plurality of pedestals. This can include the pedestal 251a and the pedestal 251b. Each of the pedestal 251a and the pedestal 251b are configured to engage with the pedestal mating openings 266 on the lateral arms 263 to allow for intermittent rotation of each of the carriage 230 about the opening 264 of the lateral arms 263. The pedestal 251a and the pedestal 251b can serve to hold the carriage 230 in a desired position until such a time as a signal or a force is applied that disengages the pedestal 251a and the pedestal 251b from the plurality of pedestal mating openings 266. This can allow rotation of the carriage 230 about the opening 264 and subsequent reengagement of the pedestal 251a and the pedestal 251b with the plurality of pedestal mating openings 266.

Each of the plurality of carriages 230 is retained in the opening of each of the plurality of arms with at least one pin (i.e., the post 258) that is configured to allow out-of-plane rotation for each of the carriage 230. The out of-plane rotation of each of the plurality of carriages 230 can move each of the plurality of carriage 230 between a plurality of orientations. For example, each of the plurality of carriage 230 moves between 180 degrees of rotation (whether in-plane or out of plane). In several embodiments, each of the carriage 230 can move between orientations where each of the plurality of chambers lies along a plane of each of the plurality of arms. Each of the plurality of carriages 230 can move between 180 degrees of rotation (e.g., 0 to 45 degrees, 45-90 degrees, 90 to 135 degrees, 135 degrees to 180 degrees, etc.).

Figures 18A, 18B:
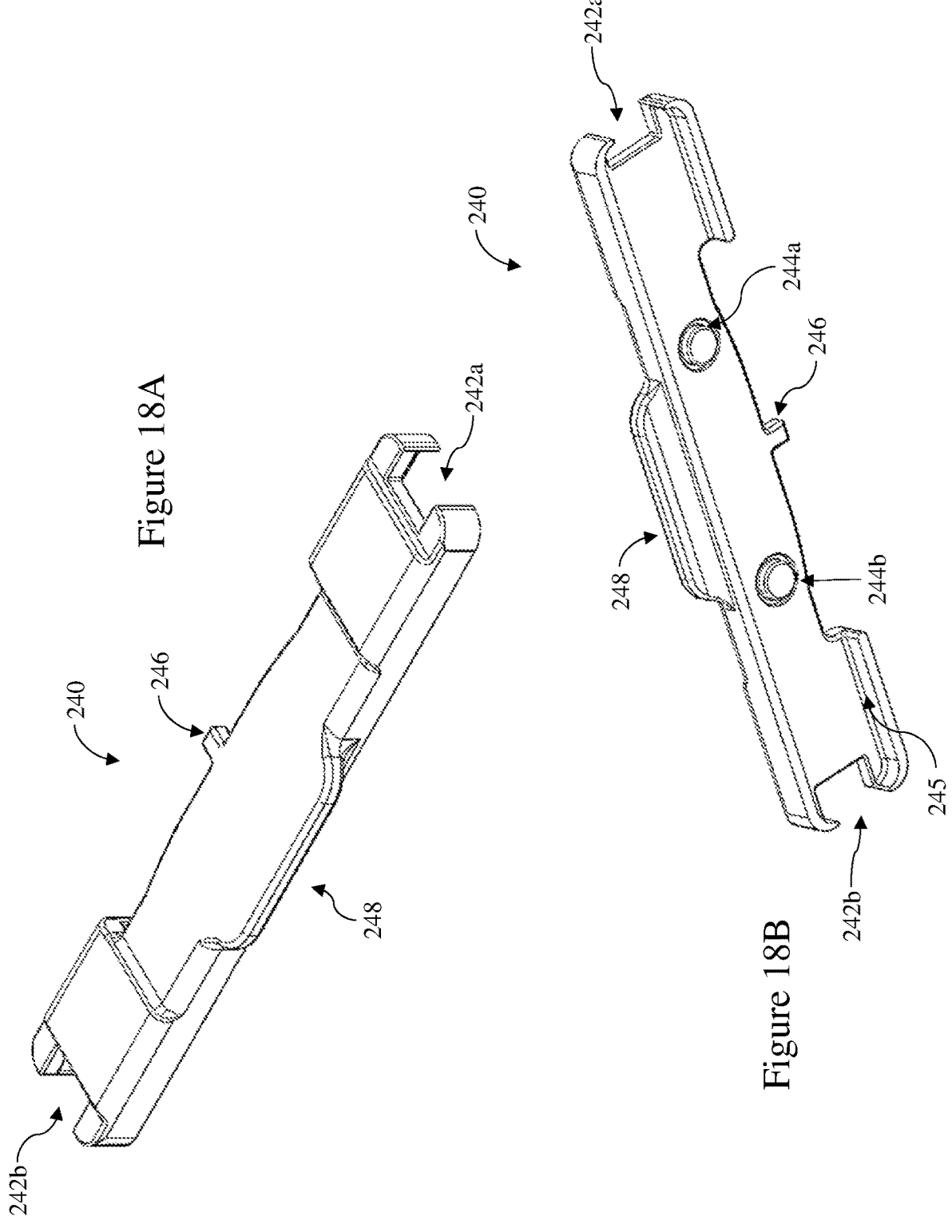
FIGS. 18A-18B illustrate an embodiment of a spring platform of the carriage assembly of FIGS. 3A-3B.
Figures 19A, 19B:
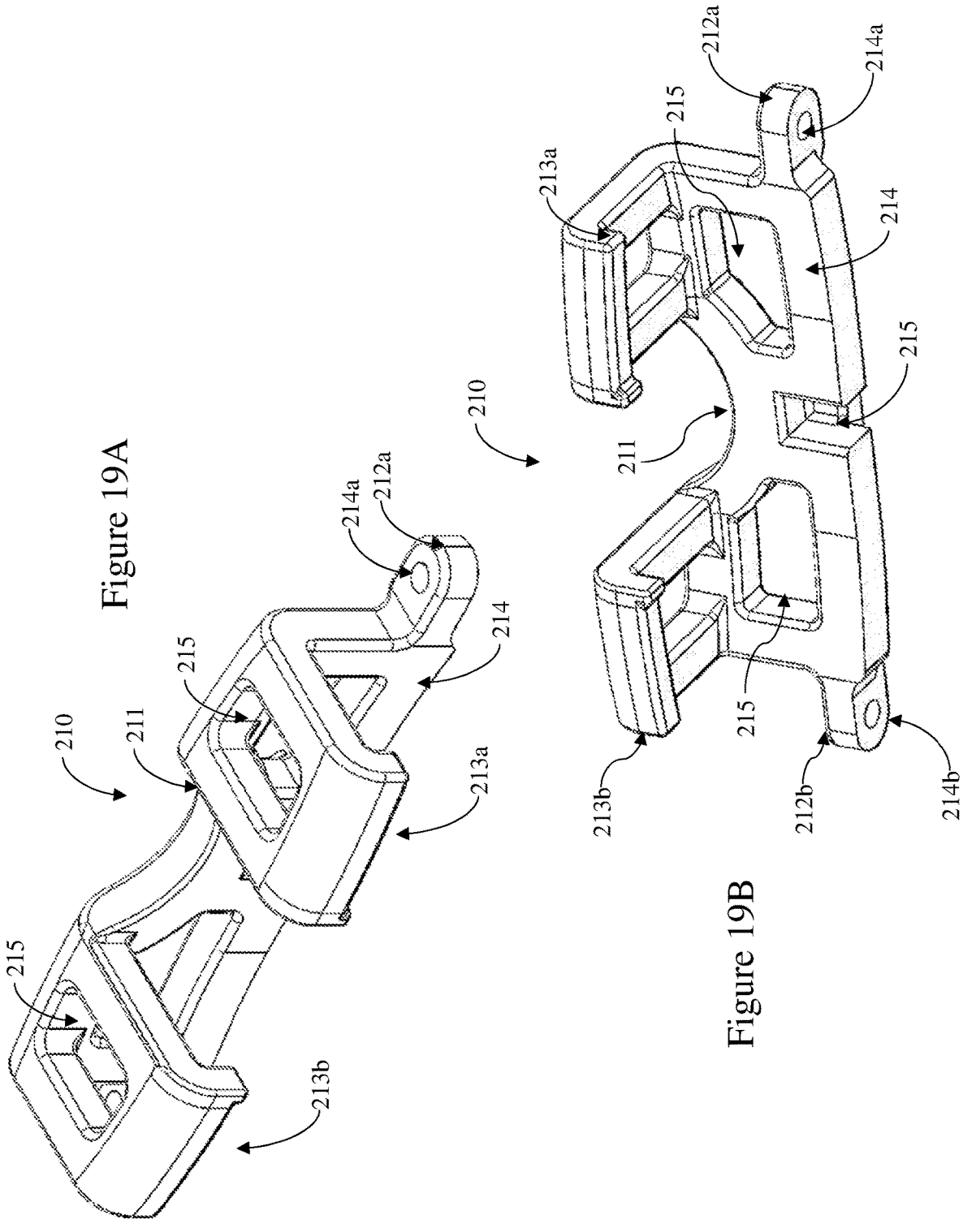
FIGS. 19A-19B illustrate an embodiment of a securement mechanism of the carriage assembly of FIGS. 3A-3B.

FIGS. 18A-18B illustrate an embodiment of the spring platform 240. As discussed above, the spring platform 240 can include a first mating area 242a on a first end of the spring platform 240 and a second mating area 242b on a second end of the spring platform 240. The spring platform 240 can include a top surface that includes a guide platform 248 positioned on side of the spring platform 240 and a chip mating tab 246 located on a side of the spring platform 240 opposite the guide platform 248. The spring platform 240 can include a bottom surface with a proximal spring holder 244a and a proximal spring holder 244b that are configured to each engage with a top portion of a springs 234. As illustrated in FIGS. 3A-3B, the first mating area 242a and the second mating area 242b are configured to secure the first arm 256a and the second arm 256b of the base platform 250 respectively. The chip mating tab 246 of the spring platform 240 can pair with an opening of the clamp 210. The spring platform 240 can include a guide platform 248 that can be used to guide the microfluidic chip 222 onto the spring platform 240 and assist in compressing the spring platform 240 as the microfluidic chip 222 is inserted into the carriage 230. The spring platform 240 can also include a splash guard 245 that overhangs over the spring platform 240 to prevent fluids from being introduced into the springs 234 under the spring platform 240. The proximal spring holder 244a and the proximal spring holder 244b can help to hold and secure the springs 234 in place during installation of the carriage 230 and during use. The spring platform 240 can vary in size and shape to fit a microfluidic chip 222 of any shape or size. The spring platform 240 can be manufactured using a variety of methods such as through: additive manufacturing, subtractive manufacturing, 3D printing, injection molding, resin molding, or urethane casting. The spring platform 240 can be made from a variety of materials such as plastic (e.g., polycarbonate, acrylic, etc.), polyurethane, or metal (e.g., aluminum, steel, stainless steel, surgical steel, brass, copper, etc).

The 19A-19B illustrate an embodiment of the clamp 210. The clamp 210 can help to hold the microfluidic chip 222 in place during use. The clamp 210 can include a finger groove 211 on the top of the clamp 210. This can allow a user to easily access the microfluidic chip 222 to remove it from the carriage 230 when necessary. As shown in FIGS. 3A-3B, the clamp 210 can include a base platform mounting area that includes a first mounting flange 212a with a first opening 214a and a second mounting flange 212b with a second mounting flange 212b. The base platform mounting area 214 can mate with the shoulder 236 of the base platform 250 by a plurality of screws (e.g., first screw 238a and second screw 238b). The clamp 210 can include a channel 215 that forms a groove to mate with the chip mating tab 246 to help retain and position the spring platform 240. The height of the channel 215 allows movement of the chip mating tab 246 in a vertical direction within the channel 215 and to guide the movement of the spring platform 240 in a single direction. The clamp 210 can include a guide rail 213a and a guide rail 213b that uses groves on the clamp 210 to help guide and position the microfluidic chip 222 into the carriage 230. The clamp 210 can also include a plurality of openings 215. The channel 215 can help to save weight of the device. As well, the channel 215 can allow the user to see the microfluidic chip 222 and/or adjust or remove the microfluidic chip 222 on the carriage 230. The clamp 210 can be manufactured using a variety of methods such as through: additive manufacturing, subtractive manufacturing, injection molding, 3D printing, resin molding, or urethane casting. The clamp 210 can be made from a variety of materials such as plastic (e.g., polycarbonate, acrylic, etc.), polyurethane, or metal (e.g., aluminum, steel, stainless steel, surgical steel, brass, copper, etc).

Other Components

Figure 20B:
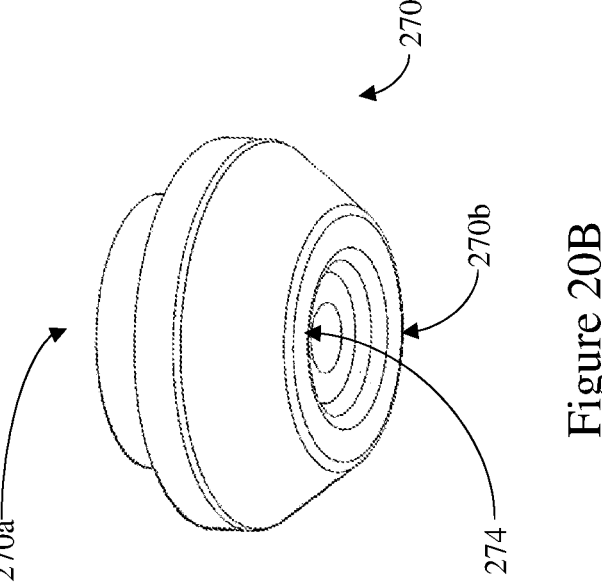
FIGS. 20A-20B illustrate an embodiment of a screw cap.
Figure 20A:
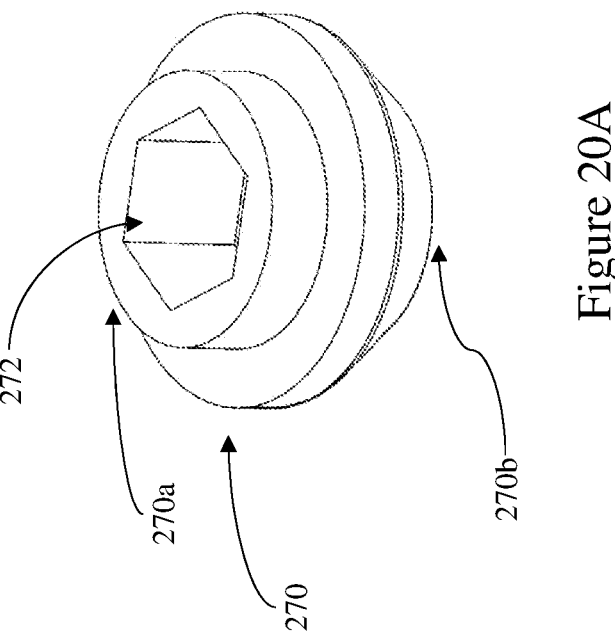

FIGS. 20A-20B illustrates a screw cap 270 that is configured to hold the base platform 250 of the carriage 230 in place. The screw cap 270 can include a proximal end 270*a* and a distal end 270*b*. The proximal end 270*a* includes a proximal opening 272 and the distal end 270*b* includes a distal end 270*b*. The proximal end 270*a* of the screw cap 270 has a shape that mates with the post 258 on the bottom surface of the base platform 250. Although the screw cap 270 illustrated in FIGS. 20A-20B illustrates a screw cap 270 with a hexagonal proximal opening 272, the proximal opening 272 can be any shape that can receive the post 258 of the base platform 250. The screw cap 270 also has a through hole that extends between the proximal end 270*a* and the distal end 270*b*. The through hole allows for the screw 232 to secure the screw cap 270 and the base platform 250 together. The screw cap 270 can include a circular proximal end 270*a*. As discussed above, the proximal end 270*a* of the screw cap 270 can be configured to extend through the opening 264 of the base 260. The screw cap 270 can allow for rotation of the carriage 230 while it is attached to the base platform 250 because of the circular shape of the screw cap 270. The screw cap 270 can be manufactured using a variety of methods such as through: additive manufacturing, subtractive manufacturing, 3D printing, injection molding, resin molding, or urethane casting. The screw cap 270 can be made from a variety of materials such as plastic (e.g., polycarbonate, acrylic, etc.), polyurethane, or metal (e.g., aluminum, steel, stainless steel, surgical steel, brass, copper, etc).

Figures 21A, 21B:
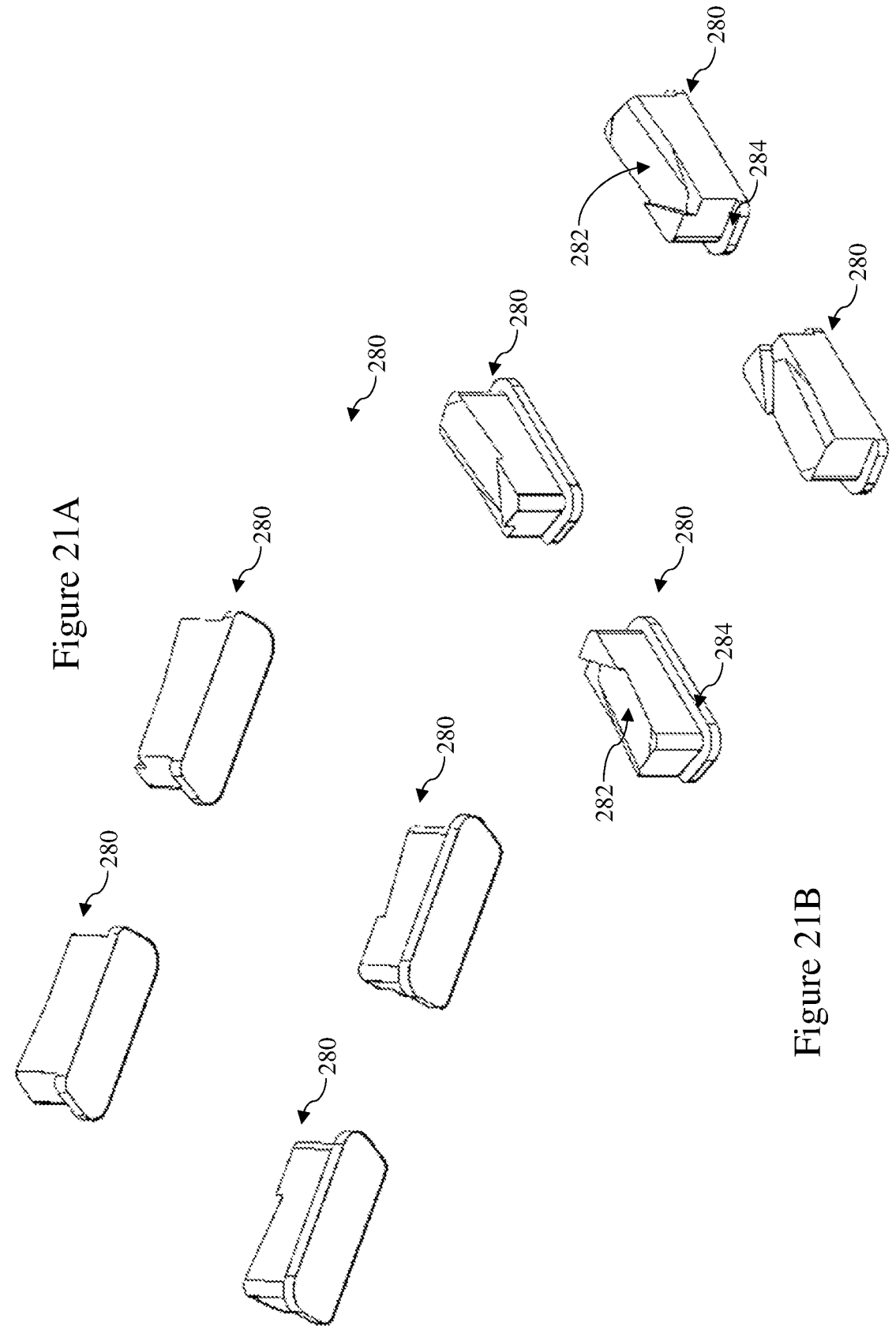
FIGS. 21A-21B illustrate an embodiment of rotor feet inserts.

FIGS. 21A-21B illustrates a plurality of rotor feet inserts 280. The rotor feet inserts 280 can include a ramp 282 on a proximal end of the rotor feet inserts 280 and a lip 284 at a base of the rotor feet inserts 280. The rotor feet inserts 280 can assist in the smooth rotation of the carriage 230. Each of the ramps 282 on each of the rotor feet inserts 280 allows the pedestals (i.e., pedestal 251*a* and pedestal 251*b*) on a bottom surface of the base platform 250 to smoothly move onto the rotor base surface when the carriage 230 is being rotated. Each of the rotor feet inserts 280 can also include a lip 284 that mates with the each of the cutouts 268 of one of the lateral arms 263 of the base 260 to help secure each of the rotor feet inserts 280 in place when in use. The rotor feet inserts 280 can be manufactured using a variety of methods such as through: additive manufacturing, subtractive manufacturing, 3D printing, injection molding, resin molding, or urethane casting. The rotor feet inserts 280 can be made from a variety of materials such as plastic (e.g., polycarbonate, acrylic, etc.), polyurethane, or metal (e.g., aluminum, steel, stainless steel, surgical steel, brass, copper, etc).

Figure 22:
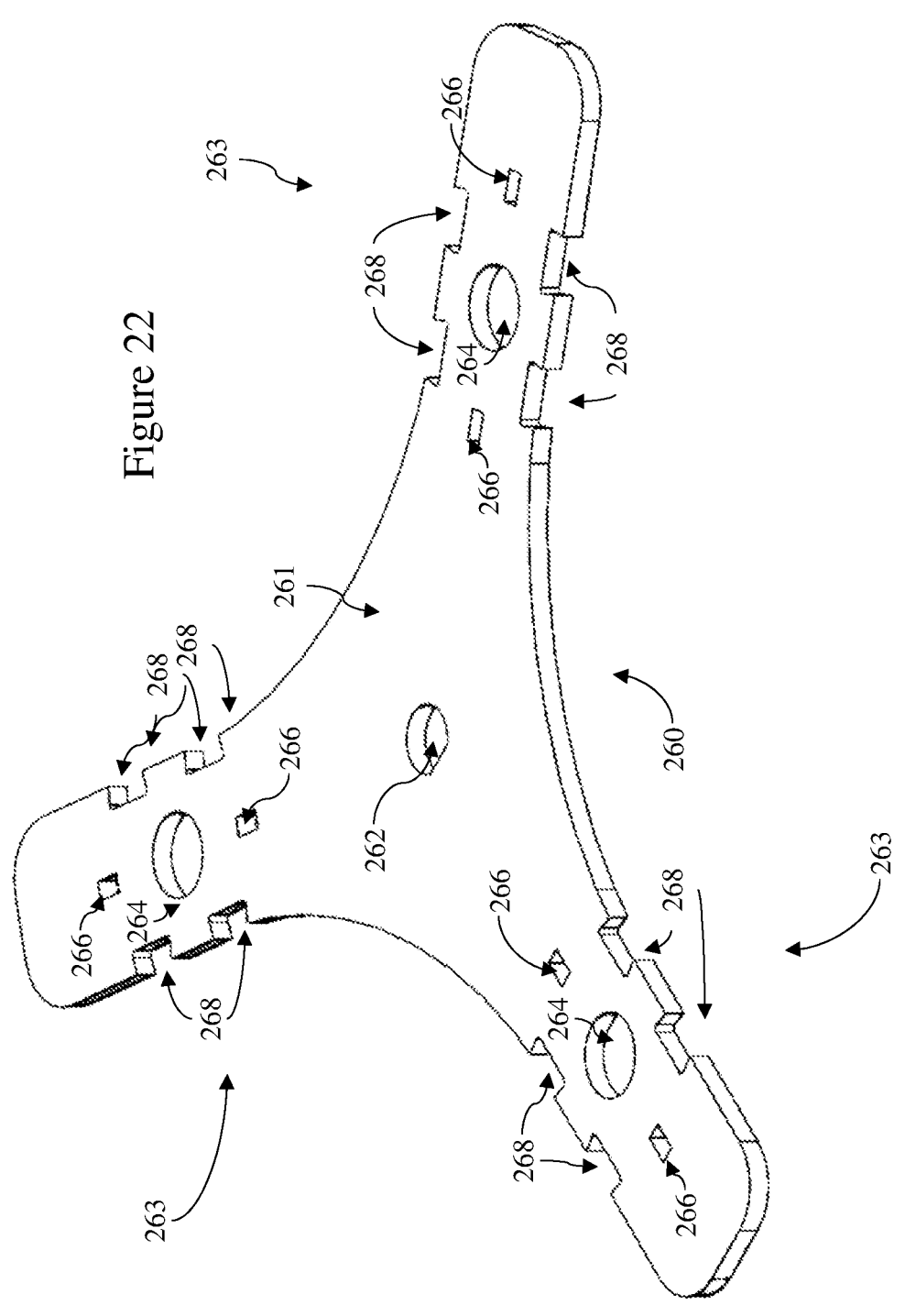
FIG. 22 illustrates an embodiment of a base of the system for processing biological system.

FIG. 22 illustrates an embodiment of the base 260. As discussed above, the base 260 can include a central portion 261 and a plurality of lateral arms 263 that extends radially away from the central portion 261 of the base 260. The base 260 of FIG. 22 illustrates a base 260 with three lateral arms 263, however the base 260 can include any number of lateral arms 263 that are configured to reversibly engage a carriage. In some embodiments, each of the lateral arms 263 are configured to lie in a plane parallel to a plane of the central portion 261. As discussed above, each of the lateral arms 263 can include an opening 264, at least one pedestal mating opening 266, and a plurality of cutouts 268. As shown in FIG. 2B, the opening 264 can be configured to receive a base of the post 258 and the plurality of cutouts 268 are configured to engage with a pedestal 251*a* and a pedestal 251*b* on a bottom surface of the base platform 250. Each of the cutouts 268 are configured to receive one of the rotor feet inserts 280. The base 260 can be designed to engage with a variety of microfluidic chips. The base 260 can include a mounting opening 262 that is configured to be attached to a centrifuge device. In some embodiments, the mounting opening 262 is a D-shaped chuck mounting opening 262 that mates with a chuck attached to a centrifuge device. The mounting opening 262 has a "D" shape to help prevent slipping during centrifugation. The base 260 also has a plurality of cutouts 268 that are a shape to help mount the rotor feet inserts. The base 260 also has a carriage mounting hole that a top portion of the screw cap 270 fits into and holds the carriage 230 in place. The base 260 also has a plurality of pedestal mating openings 266 that mate with the pedestals on a bottom surface of the base platform 250 to keep the carriage aligned during use. The base 260 can be manufactured using a variety of methods such as through: additive manufacturing, subtractive manufacturing, 3D printing, injection molding, resin molding, or urethane casting. The base 260 can be made from a variety of materials such as plastic (e.g., polycarbonate, acrylic, etc.), polyurethane, or metal (e.g., aluminum, steel, stainless steel, surgical steel, brass, copper, etc).

OTHER EMBODIMENTS

Figure 23A:
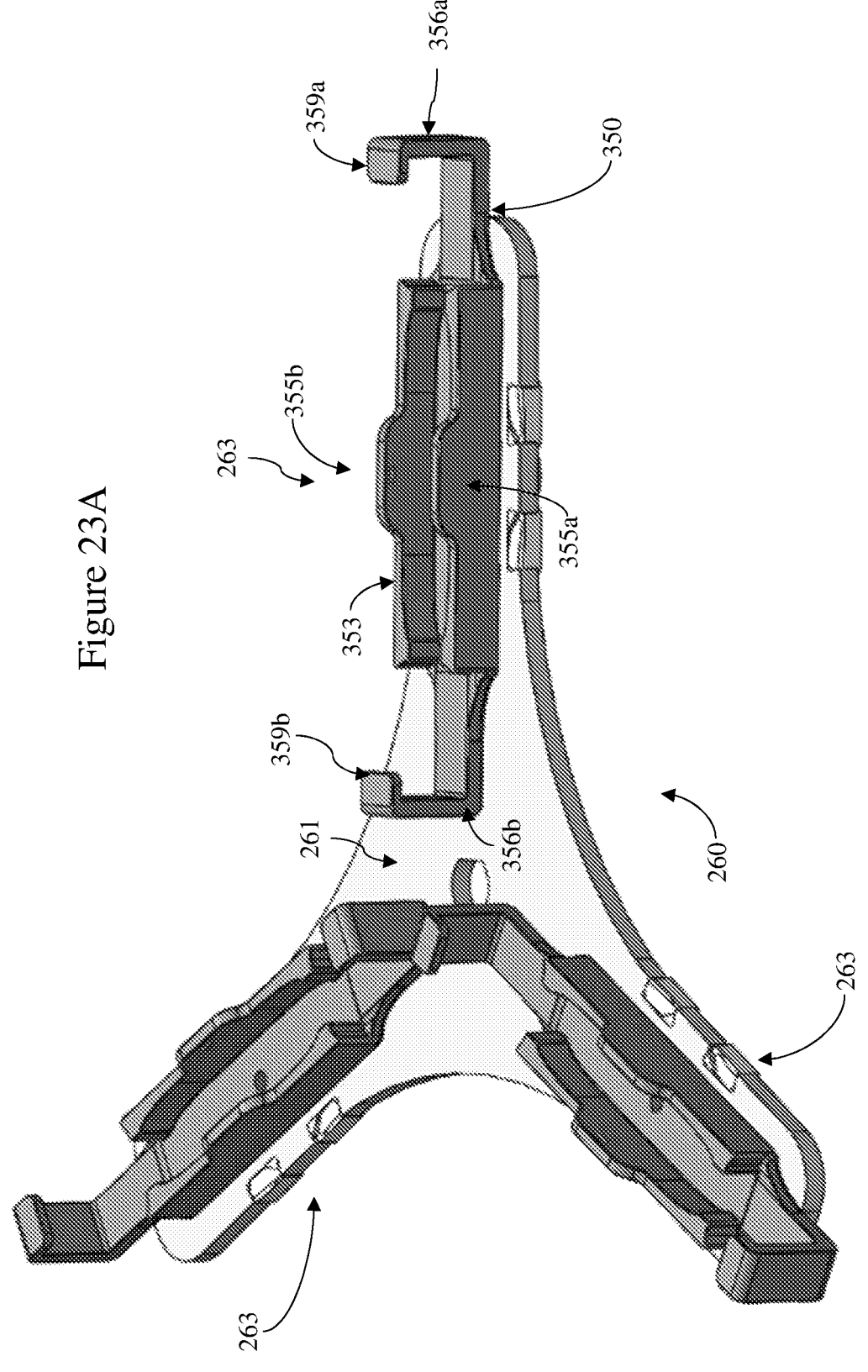
FIGS. 23A-23B illustrate another embodiment of a system for processing biological systems.
Figure 23B:
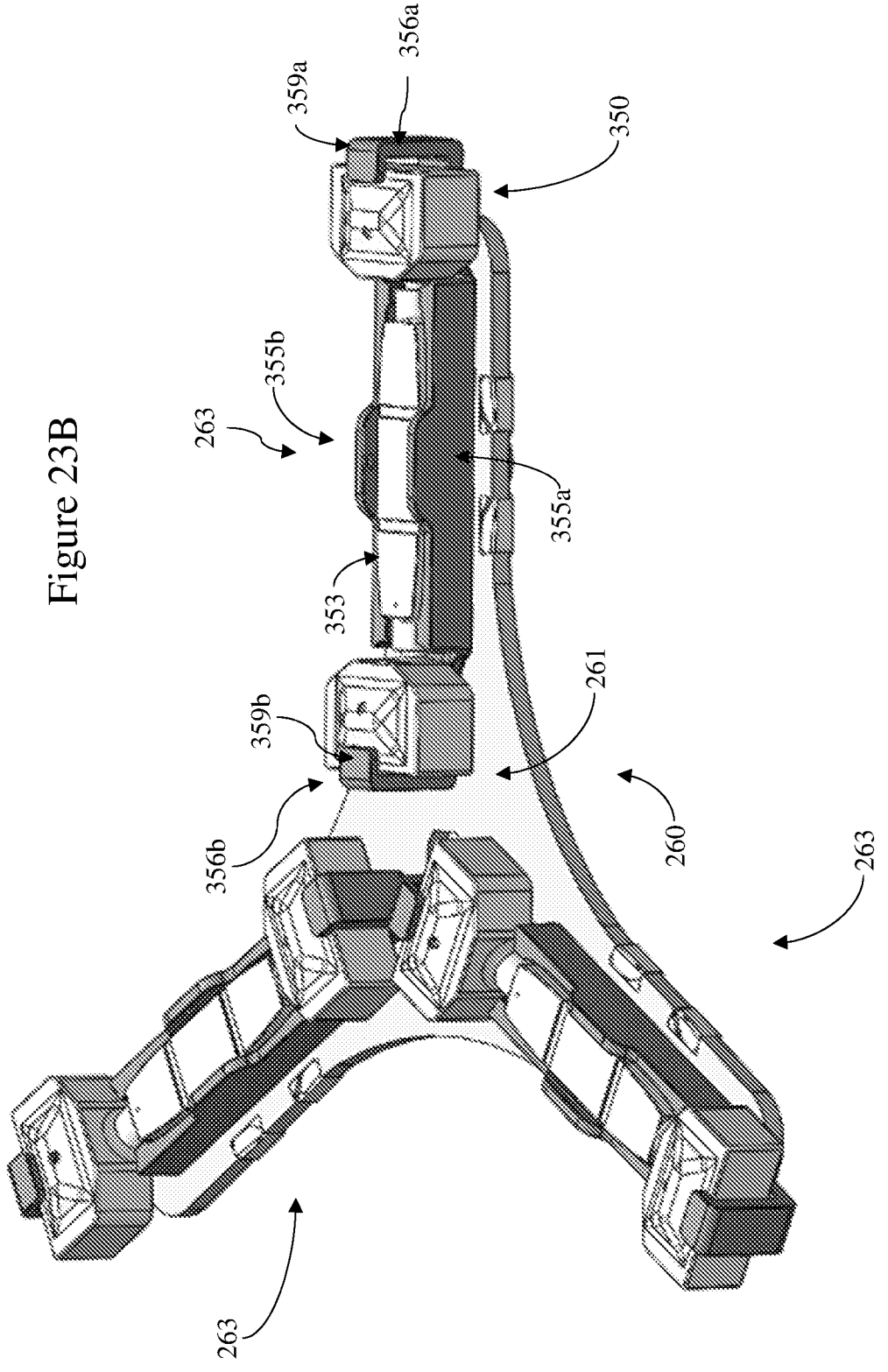

FIGS. 23A-23B illustrates an embodiment of the centrifugal device wherein each of the carriage 330 includes a clamping and locking mechanism for holding the chip assembly 220 in place during processing. As illustrated in FIG. 23A, the carriage 330 includes a base platform 350 with a first side 355*a* and a second side 355*b* to form a opening 353. The opening 353 can secure and retain the microfluidic chip 222 of the chip assembly 220. The base platform 350 can include a first arm 356*a* at a first end of the base platform 350 and a second arm 356*a* at a second end of the base platform 350. The first arm 356*a* and the second arm 356*a* can form clamps on either end of the carriage 330 to secure the chip assembly 220. The clamp formed by the first arm 356*a* and the second arm 356*a* can be separated and pulled apart with one hand to allow the chip assembly 220 to be removed from the base platform 350. In some embodiments, the carriage 330 can be positioned on each of the lateral arms 263 of the base 260 such that it can be rotated 360 degrees for reprocessing. The carriage 330 can include pedestals on opposite ends of the carriage 330 to help secure the carriage 330 in an orientation parallel to the wing (as disclosed above). The carriage 330 is otherwise like the carriages discussed elsewhere in this application.

Figure 24:
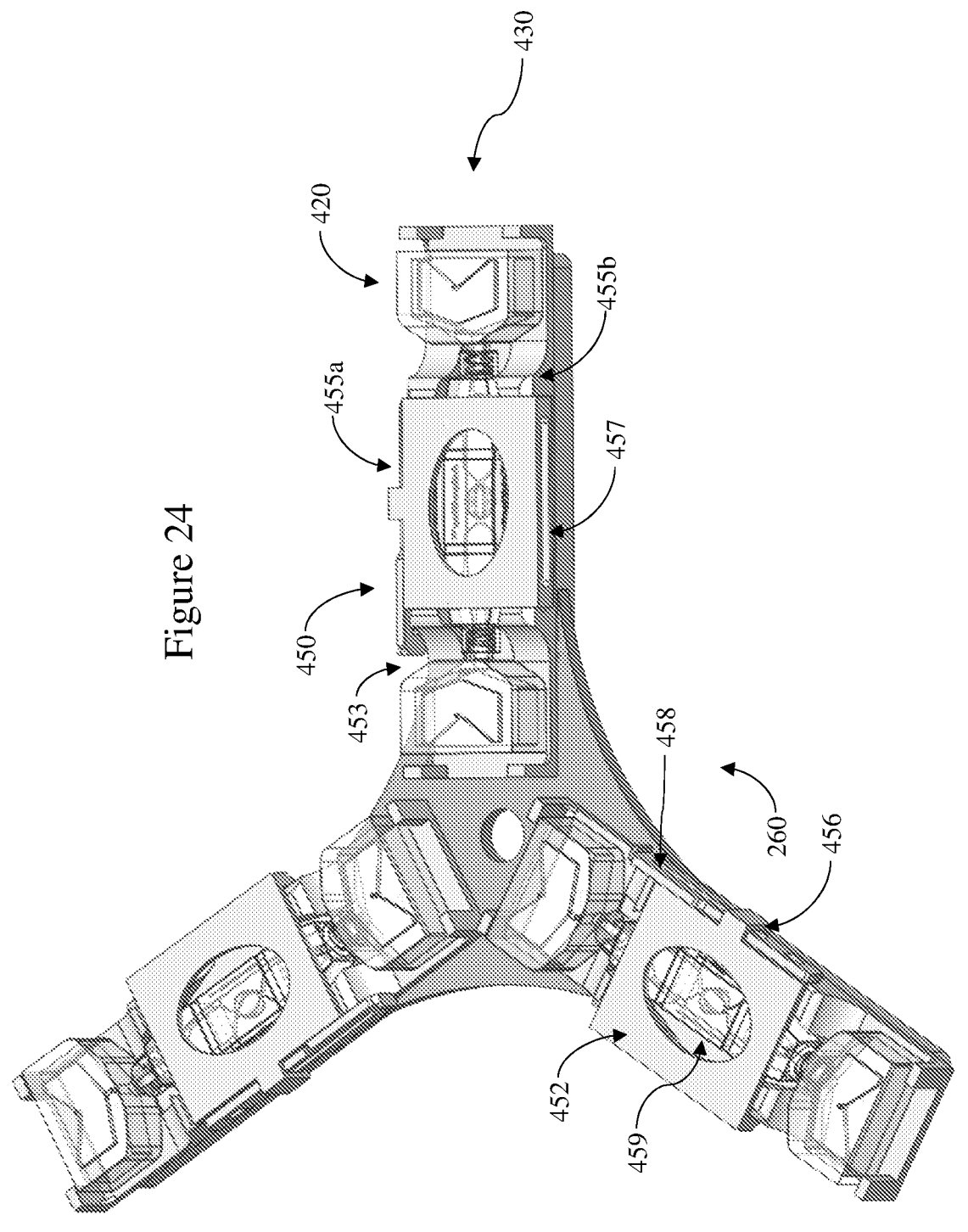
FIG. 24 illustrates another embodiment of a system for processing biological systems.

FIG. 24 illustrates a centrifugal device with an alternative securing portion to the clamp 210 disclosed above. As illustrated in FIG. 24, the carriage 430 utilizes a clamping and locking mechanism for holding the chip assembly 420 in place during processing. As illustrated, the base platform 450 of the carriage 430 can include a first side 455*a* and a second side 455*b*. A hinge 457 can be positioned on the second side 455*b* of the base platform 450 and an engagement portion 456 can be positioned on the first side 455*a* of the base platform 450. The hinge 457 can moveably connect the lid 452 to the base platform 450. The lid 452 can include a window 459 to allow the microfluidic chip of the chip assembly 420 to be viewed during processing. The engagement portion 456 can include a slide lock that goes through a latching hole on the side of the lid and then couples with a locking stop to hold the chip assembly 420 to the carriage 430. In some embodiments, the latch can be undone using one hand and unlatches by pulling the slide lock away from carriage to unlatch the slide lock. Then the slide lock slides back through the latching hole on the lid to unlock the device. The lid 452 can swing open using the hinge 457 on the second side 455*b*. The carriage 430 of FIG. 24 can be rotated 360 degrees for reprocessing. The carriage 430 can include pedestals on opposite ends of the carriage 430 to help secure the carriage 430 in an orientation parallel to the wing (as disclosed above). The carriage 430 is otherwise like the carriages discussed elsewhere in this application.

Figure 25A:
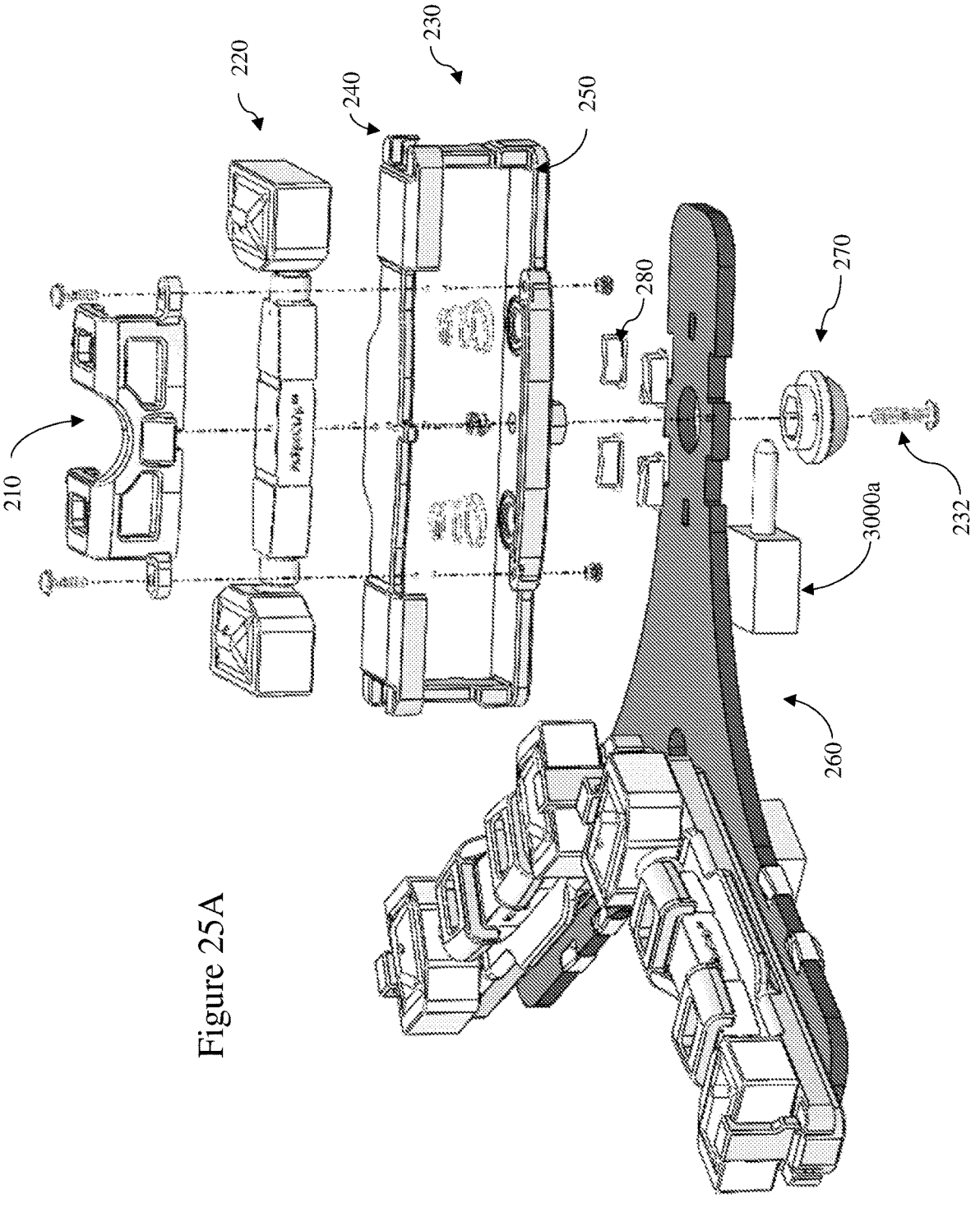
FIGS. 25A-25B illustrate an embodiment of the system for processing biological system that includes an embodiment of a motor.
Figure 25B:
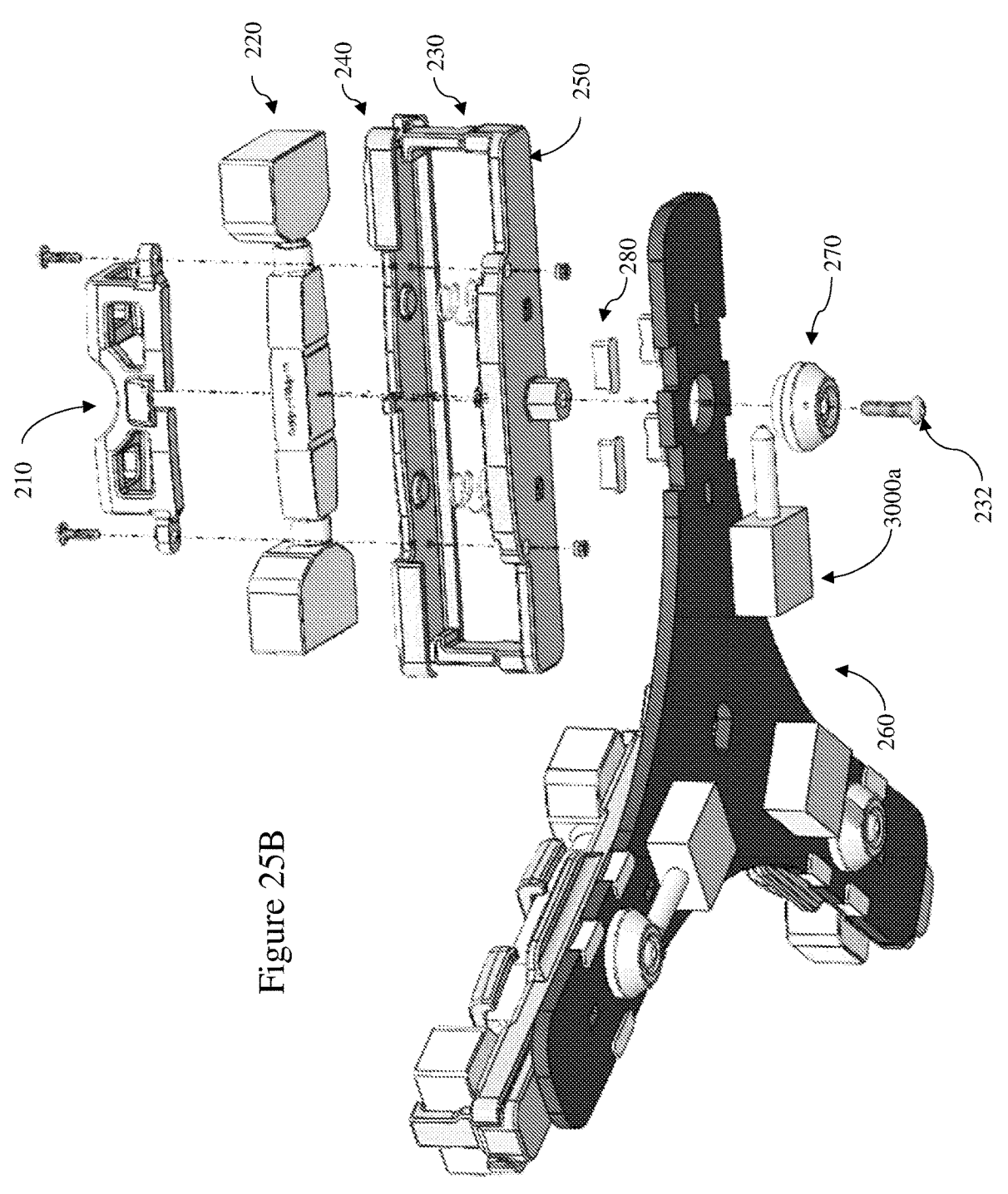

FIGS. 25A-25B illustrate an embodiment of a centrifugal device that further includes a motor 3000*a* that is attached to the bottom of the rotor base that connects to the screw cap 270. The motor 3000*a* can allow for the automated and controlled rotation of the carriage 230. The motor 3000*a* can be battery powered or connected to an electricity source through the base 260.

Figure 26A:
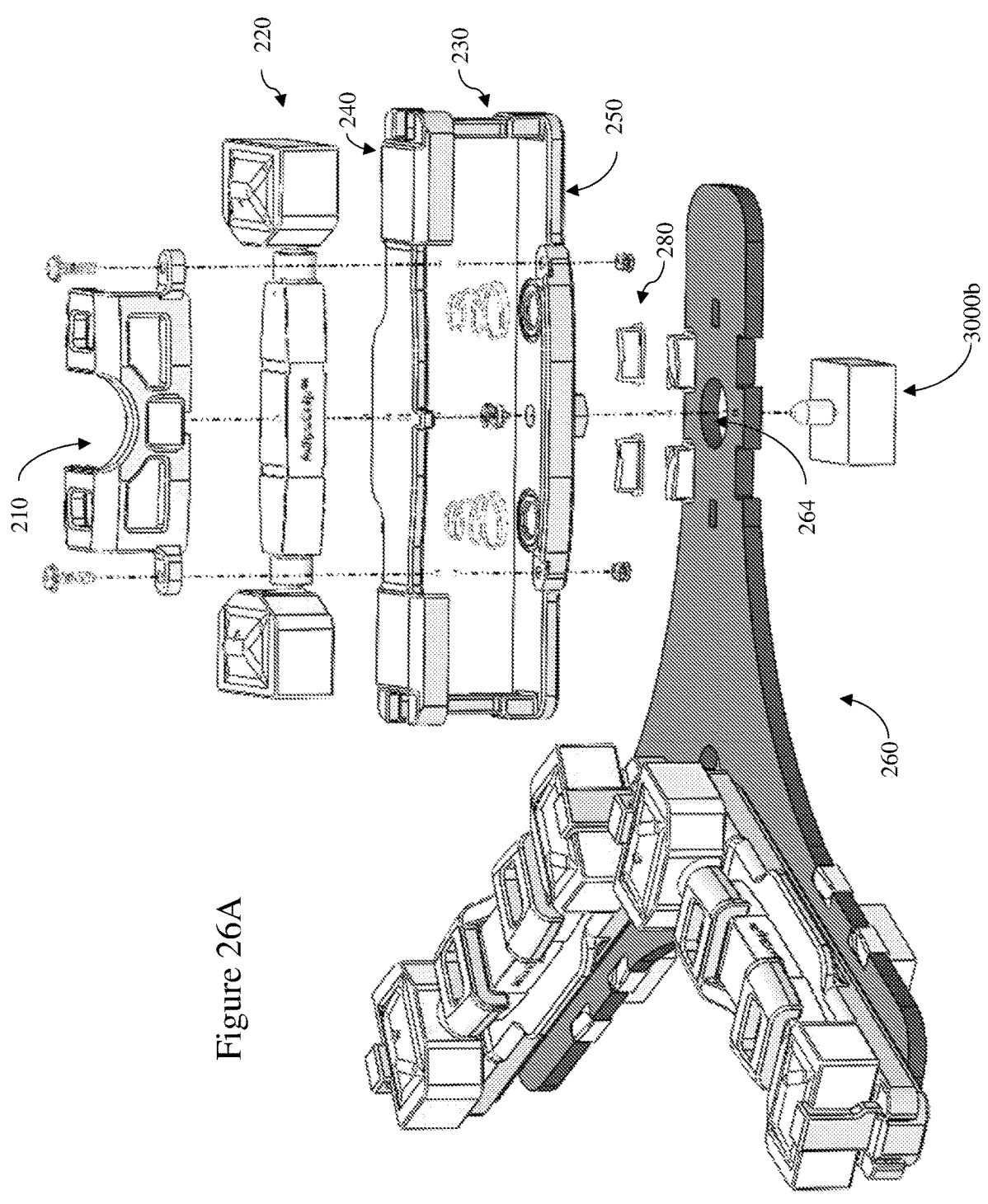
FIGS. 26A-26B illustrate another embodiment of the system for processing biological system that includes another embodiment of a motor.
Figure 26B:
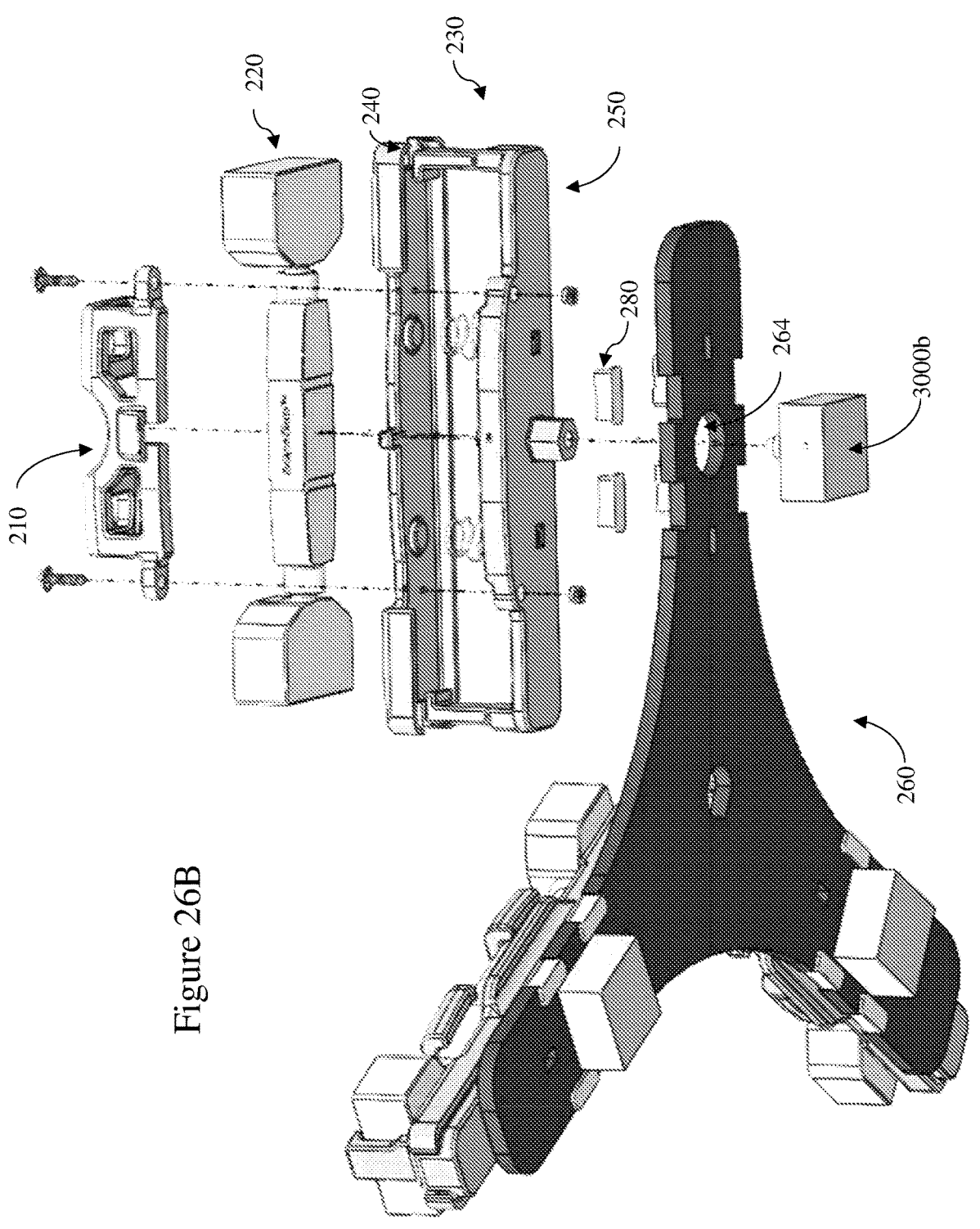

FIGS. 26A-26B illustrate an embodiment of a centrifugal device that includes a motor 3000*b* that is attached to the bottom of the base 260 that connects to the post 258 on the bottom surface of the base platform 250. The motor 3000*b* can allow for automated rotation of the carriage 230. The motor 3000*b* can be battery powered or connected to an electricity source through the base 260.

Figure 27A:
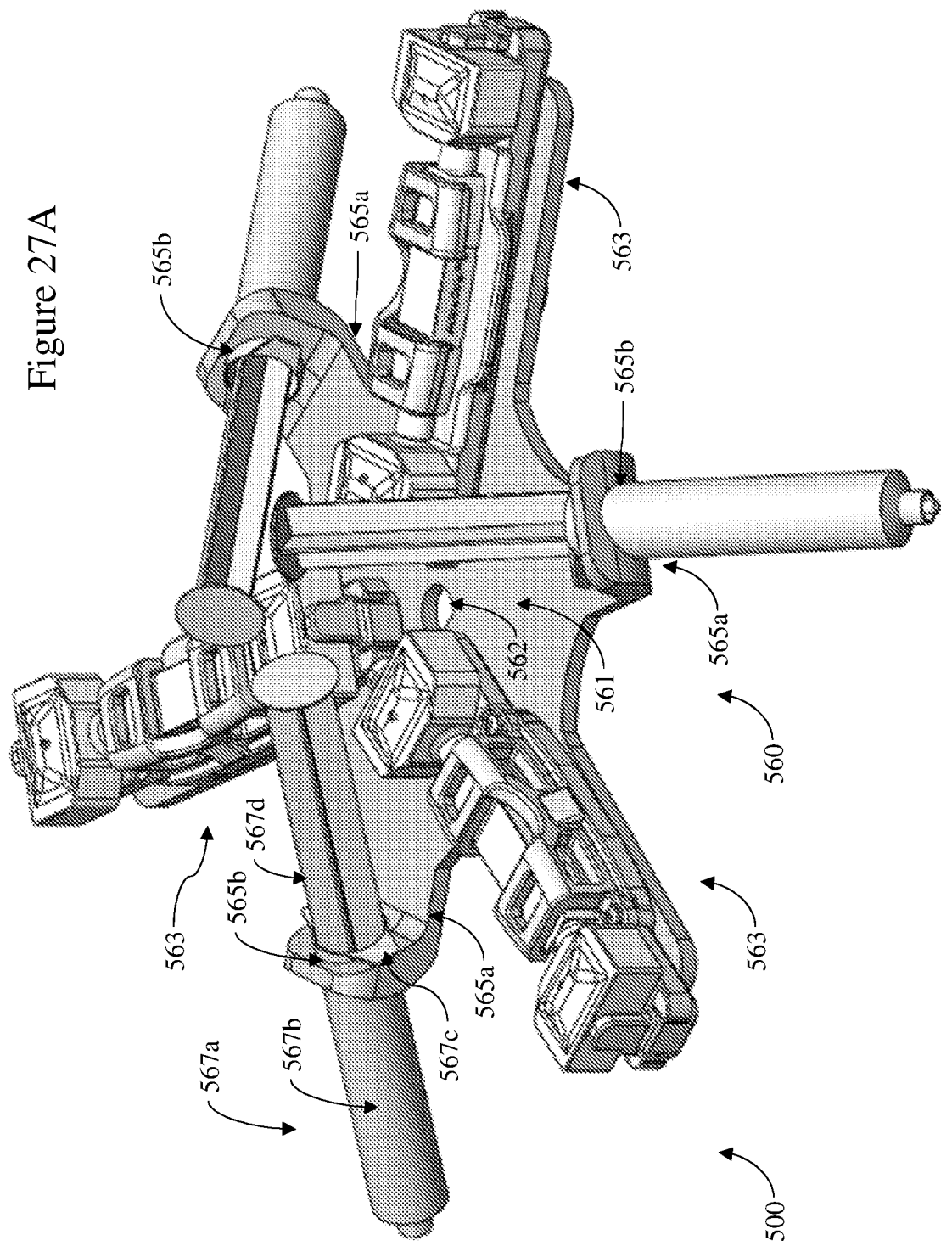
FIGS. 27A-27D illustrate an embodiment of a system for processing biological systems with structures to retain a plurality of syringes.
Figure 27B:
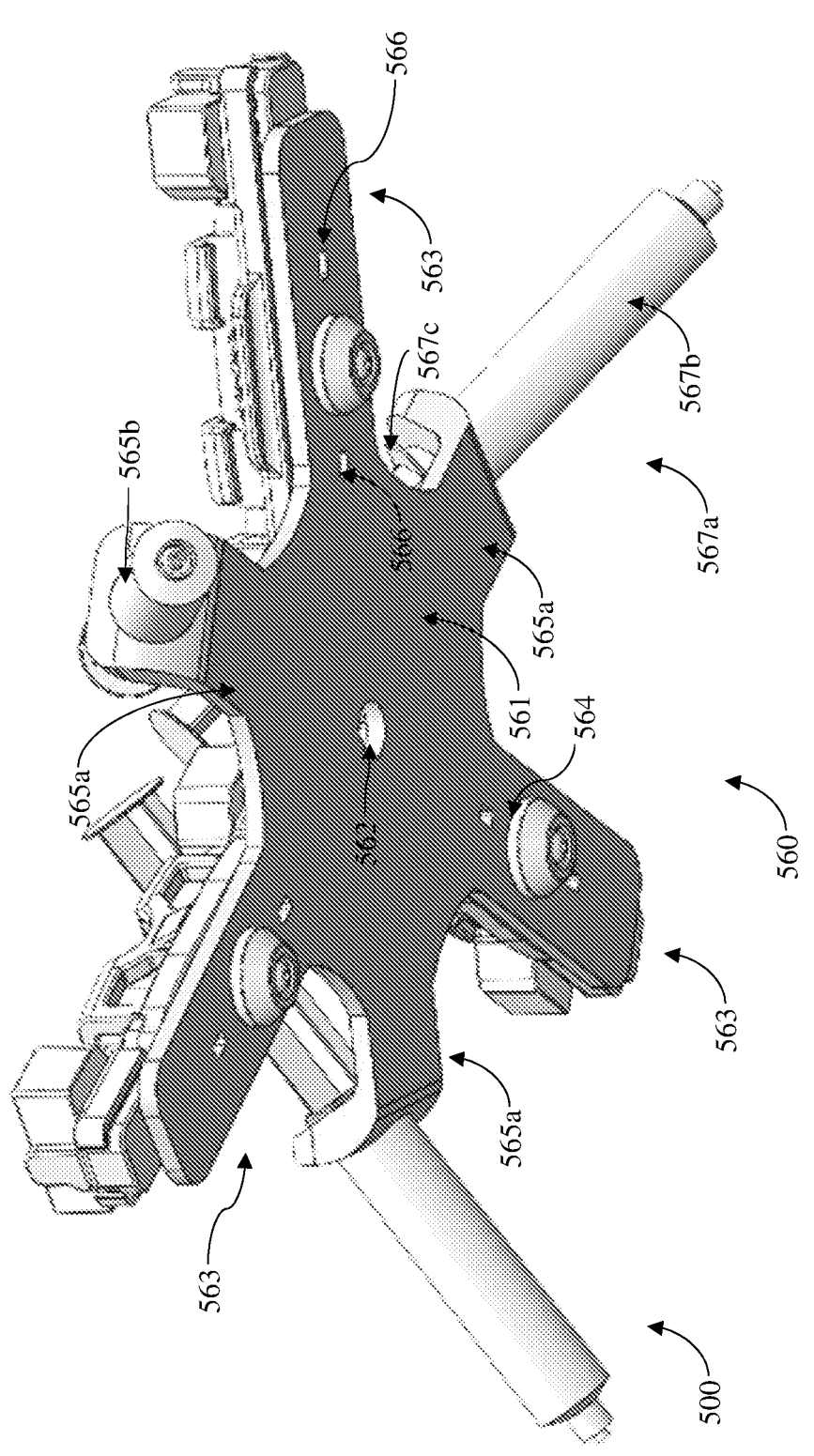
Figure 27C:
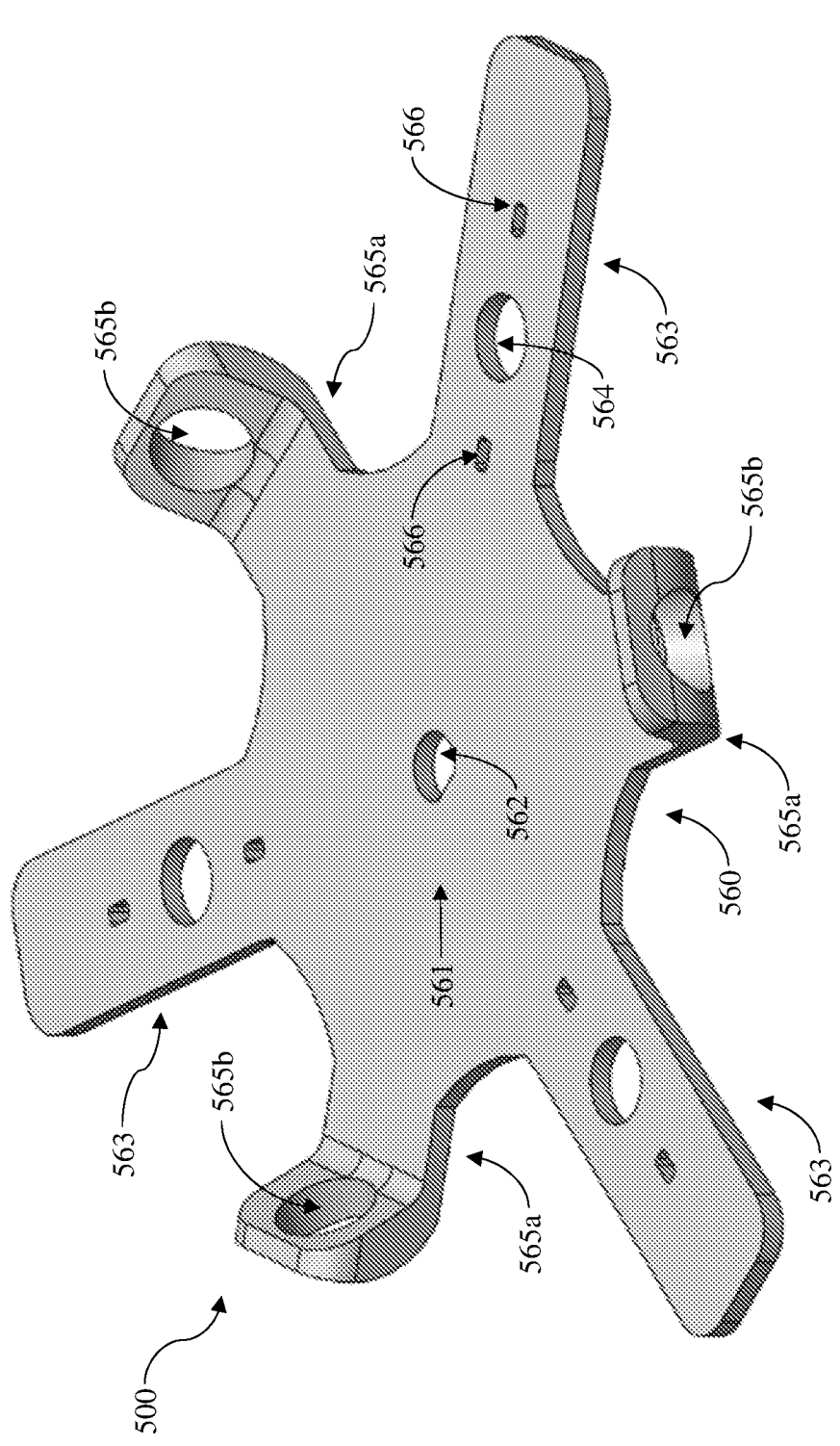

FIGS. 27A-27D illustrate another embodiment of the centrifugal device 500 for processing biological samples. The centrifugal device 500 illustrated in FIG. 28 show a centrifugal device 500 that can provide a multi-use centrifugal device 500 that can be employed in different states of a processing protocol. The base 560 of the centrifugal device 500 can retain a plurality of syringes. As illustrated in FIG. 27C, the centrifugal device 500 can include a base 560 that includes a central portion 561 with a mounting opening 562 and plurality of lateral arms 563. Each of the lateral arms 563 is similar to the lateral arms 263 of the base 260 discussed above. Like the lateral arms 263 of the base 260, the lateral arms 563 of the base 560 includes an opening 564 for receiving a post 258 of the base platform 250 of the carriage 230 to allow the carriage 230 to rotate about the opening 564. The lateral arms 563 also includes a plurality of pedestal mating openings 566 that retain the pedestals (e.g., pedestal 251*a* and the pedestal 251*b*) of the carriage 230 in a desired position until such time as there is a force, or lack thereof, to allow the pedestals to disengage. The base 560 further includes a plurality of syringe holding arms 565*a* that are positioned between adjacent lateral arms 563. The syringe holding arm 565*a* can include a flared distal end 568 with an opening 565*b*. The distal end 568 can be angled or chamfered such that the opening 565*b* is not perpendicular to the syringe holding arm 565*a*. The flared distal end 568 can angle the opening 565*b* at an angle with respect to the plane of the syringe holding arm 565*a*. In some examples, the opening 565*b* is angled between about 100 to 130 degrees at the distal end 568. In some embodiments, the distal end 568 can include an opening 565*b* at a 90 degree angle. The configuration illustrated in FIGS. 27A-27D allows a plurality of samples to be processed to activate cells while the syringes are used to subject additional samples to gradient separation. This can be important as it can allow a particular subpopulation of cells from a sample to be isolated and then subjected to activation by processing through a microfluidic chip that is placed on the carriage of one of the lateral arms 263 of the base 260).

Figure 27D:
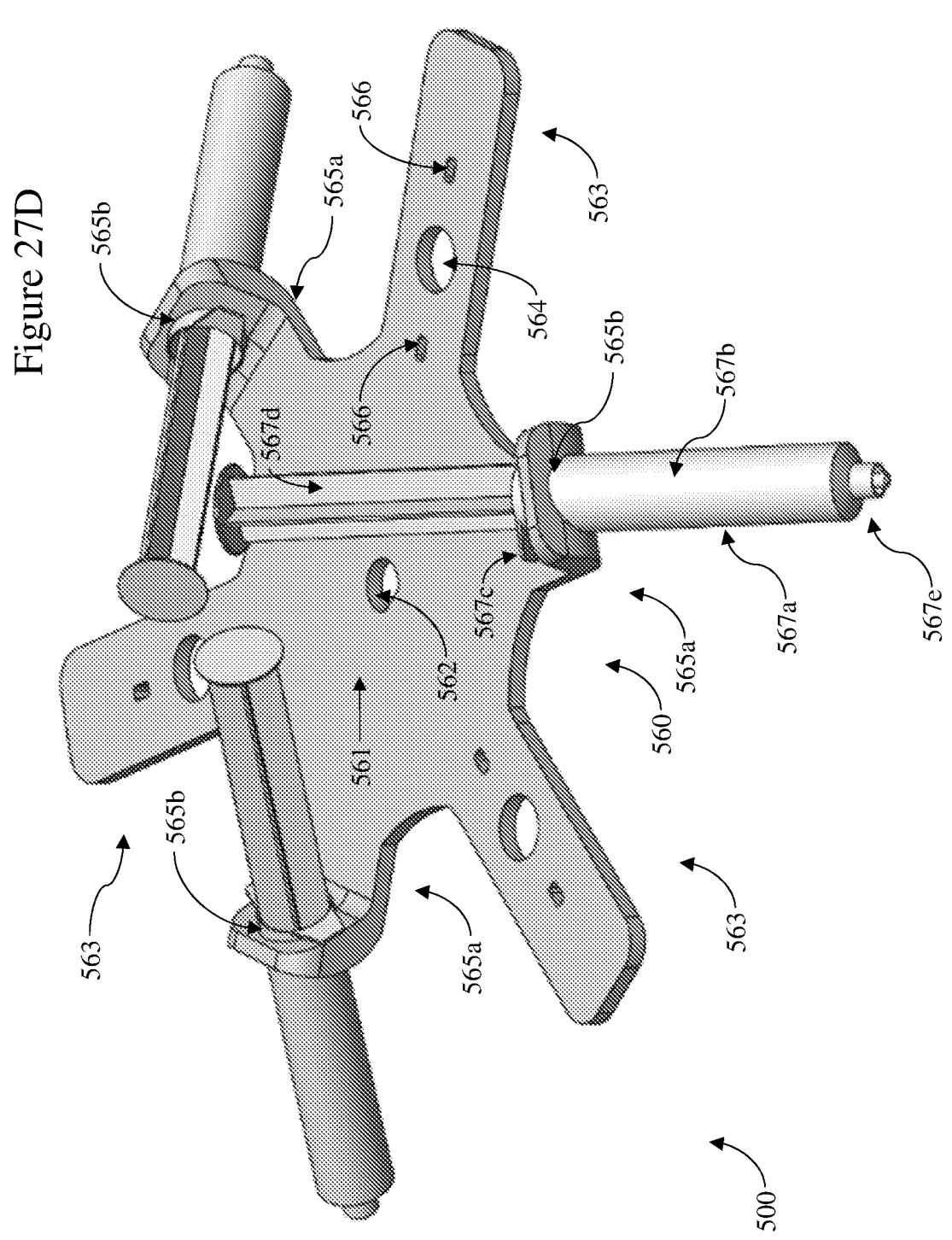
Figures 27E, 27F:
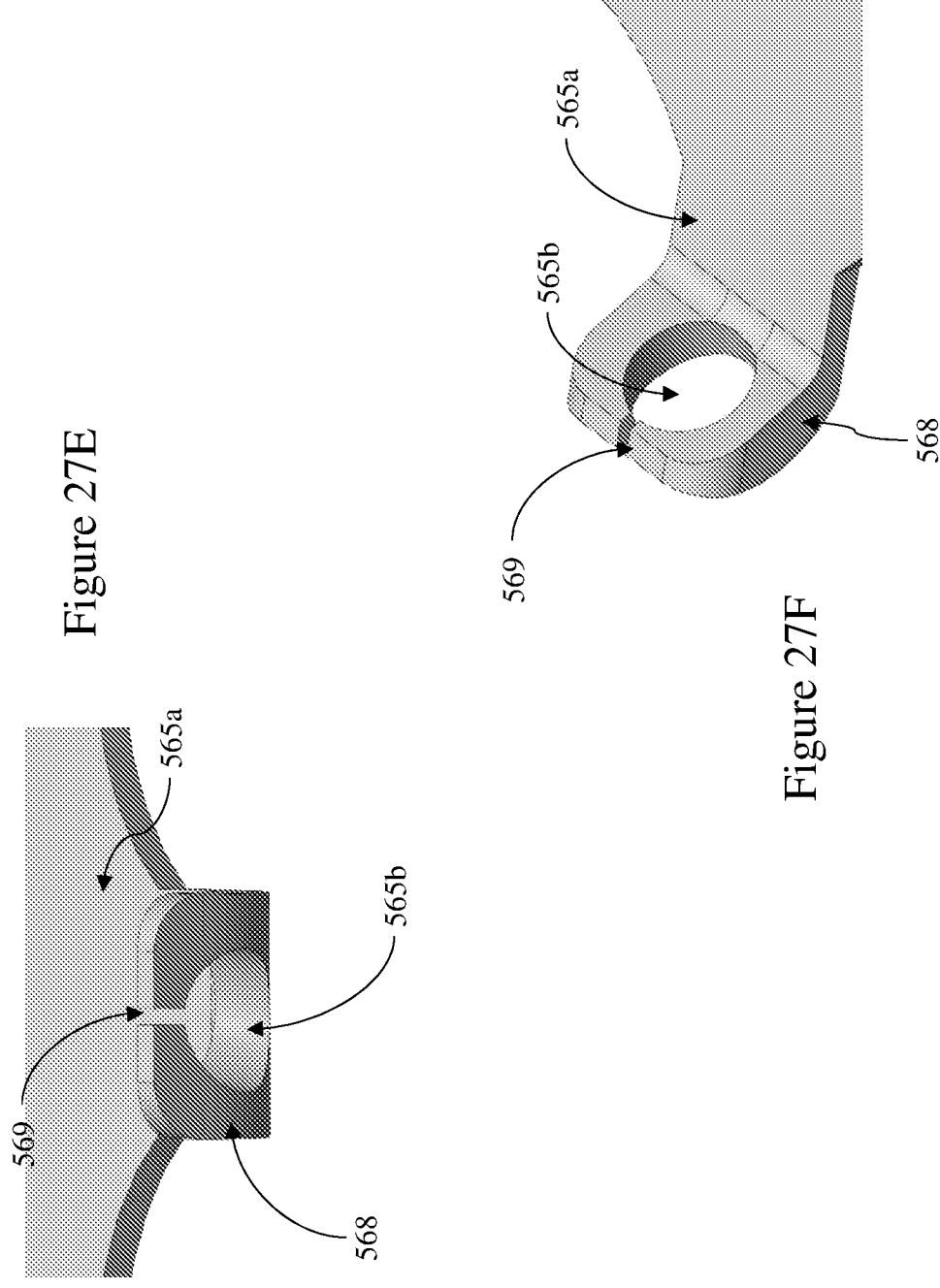
FIGS. 27E-27F illustrates a distal end of the structure to retain the plurality of syringes in the embodiment of the system for processing biological systems of FIGS. 27A-27D.

As illustrated in FIG. 27D, the plurality of the openings 565*b* can allow for the placement of a plurality of syringes 567*a* through the opening 565*b*. Each of the openings 565*b* is positioned with the needle hub 567*e* in a distal position relative to the plunger 567*d*. In some embodiments, the syringe 567*a* includes a flange 567*c* that rests against the flared distal end 568 to retain the syringe 567*a* during the application of centrifugal force. In some embodiments, the opening 565*b* of the distal end 568 can hold the syringe 567*a* at an angle between 0 and 80 degrees from a horizontal position. In some examples, the opening 565*b* of the distal end 568 can hold the syringe 567*a* at an angle between 0 and 45 degrees from a vertical position. The distal end 568 of the syringe holding arms 565*a* are configured to fit a plurality (e.g., three) of syringes 567*a* at the same time and to provide for maximum centrifugation on the syringes. As shown in FIGS. 27E-27F, the distal end 568 of the syringe holding arm 565*a* can allow each of the syringes 567*a* to slide into place. The opening 565*b* of the distal end 568 can include a gap 569 that allows the distal end 568 of the syringe holding arm 565*a* to expand to receive a variety of syringes. For example, the opening 565*b* of the distal end 568 of the syringe holding arm 565*a* can be used with syringes holding volumes ranging from 1 mL to 100 mL.

In some embodiments, the distal end 568 of the syringe holding arm 565*a* can be machined or grooved to approximate the shape of a particular barrel 567*b* of the syringe 567*a*. In some embodiments, the distal end 568 of the syringe holding arm 565*a* can receive and retain an insert wherein the insert is dimensioned to hold any number of additional syringes. The insert can be configured such that the number of additional syringes is inversely proportional to the diameter of each of the openings for retaining the syringe.

Use of Centrifugal Device for Processing Biological Samples

The disclosed centrifugal devices herein process biological samples to allow reinjection or reapplication of the tissue into the patient to provide repair and/or regeneration. In some embodiments, the biological sample can be an adipose tissue, although other types of tissue can be processed using the systems and methods disclosed herein. In some embodiments, adipose tissue, tumor tissue, cellular preparations, lipoaspirates, cultured cells, and other similar biological samples can be processed. In some examples, the biological sample comprises particles (e.g., nanoparticles, magnetic particles, particles coated with a reagent or antibody, etc.). In some embodiments, the sample includes a cell containing fluid.

Figure 28A:
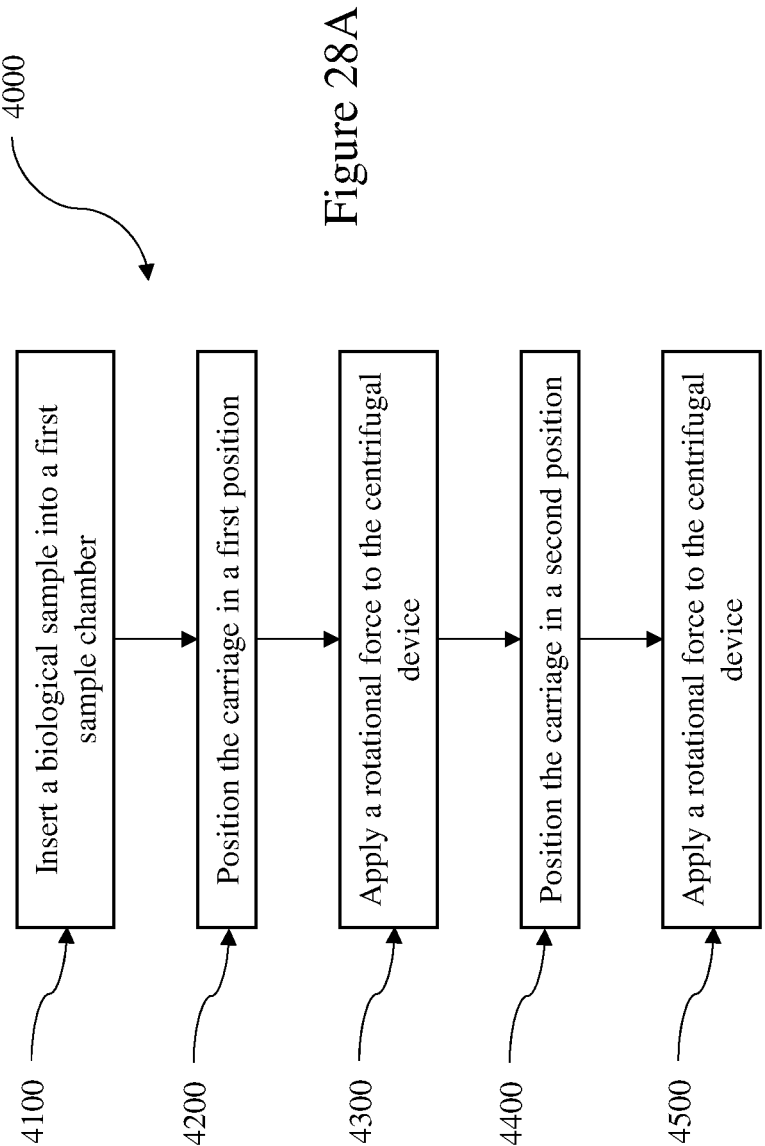
FIG. 28A illustrates a flowchart of a method for processing biological materials.

FIG. 28A illustrates an embodiment of a method for processing biological samples 4000. In the method for processing biological samples 4000, at step 4100, a biological sample is inserted into a first sample chamber. Turning to the centrifugal device 200 illustrated in FIGS. 2A-2B as a non-limiting example, in some embodiments, a biological sample can be loaded into one of the sample holding chamber 290*a* or sample holding chamber 290*b* that are fluidically coupled to the microfluidic chip 222 at either end of the microfluidic chip 222. As discussed above, the fluid path of the microfluidic chip 222 is configured to allow passage of the biological sample bidirectionally between the sample holding chamber 290*a*, the microfluidic chip 222, and the sample holding chamber 290*b*.

In the method for processing biological samples 4000, at step 4200, the carriage of the centrifugal device is positioned in a first position. The carriage 230 of the centrifugal device 200 can be secured to the lateral arms 263 of the base 260 to be rotatable about an axis perpendicular to or substantially perpendicular to the plane of the central portion 261 of the base 260. During the operation of the centrifugal device 200, the carriage 230 starts in a first position wherein a first end (i.e., the sample holding chamber 290*a*) of the carriage 230 is positioned furthest from the central portion 261. The carriage 230 can be rotated to a second position wherein a second end (i.e. the sample holding chamber 290*b*) of the carriage 230 is positioned furthest from the central portion 261.

The method for processing biological samples 4000 can include step 4300 wherein a rotational force is applied to the centrifugal device. A rotational force can be applied to the centrifugal device 200 to allow the sample in the sample holding chamber 290*a* to pass from the sample holding chamber 290*a* into the microfluidic chip 222 through the first port 221*a*. The sample can then pass through the fluid path of the microfluidic chip 222 from a first end of the microfluidic chip 222 to the second end of the microfluidic chip 222. The sample can then pass out of the microfluidic chip 222 through the second port 221*b* and into the sample holding chamber 290*b*.

The method for processing biological samples 4000 can include step 4400 where the carriage is moved from the first position into the second position. The carriage 230 can then be rotated (i.e., 180 degrees) such that the carriage 230 is moved from a first position to a second position. In several embodiments, the rotation is automated.

The method for processing biological samples 4000 can include step 4500 where a rotational force is again applied to the centrifugal device. In this second position, rotational force can be applied to the centrifugal device 200 to allow the sample in the sample holding chamber 290*b* to pass from the sample holding chamber 290*b* in the 22 through the second port 221*b* and into the fluid path of the microfluidic chip 222. The sample can then pass through the fluid path of the microfluidic chip 222 from the first end to the second end of the microfluidic chip 222. The sample can then move out of the first port 221*a* and into the sample holding chamber 290*a*. The steps of the method for processing biological samples 4000 can be repeated until the sample is processed to a desired degree.

The method for processing biological samples 4000 can be used on the centrifugal device 500 illustrated in FIGS. 27A-27D. In the centrifugal device 500, each of the syringes 567*a* retained in the syringe holding arm 565*a* also includes a biological sample in the barrel 567*b*. When rotational force is applied to the base 560, centrifugal force is also applied to the biological sample in the syringe 567*a* to form a gradient separation of the biological sample. This can be important as it can allow a particular subpopulation of cells from a sample to be isolated first before being subjected to activation by processing through a microfluidic chip. Because each of the syringe 567*a* can be easily removed from the base 560, the biological material from the syringe 567*a* (or from any of the sample chambers attached to the microfluidic chip) can be removed and reattached to the chip assembly and the carriage before continuing further processing of the biological material. The method of processing biological samples 4000 can therefore be tailored to a variety of applications and uses.

In some embodiments, after processing the biological sample according to the method of processing biological samples 4000, the processed biological sample can be injected into a patient.

Methods of Treating

Overview

Figure 29:
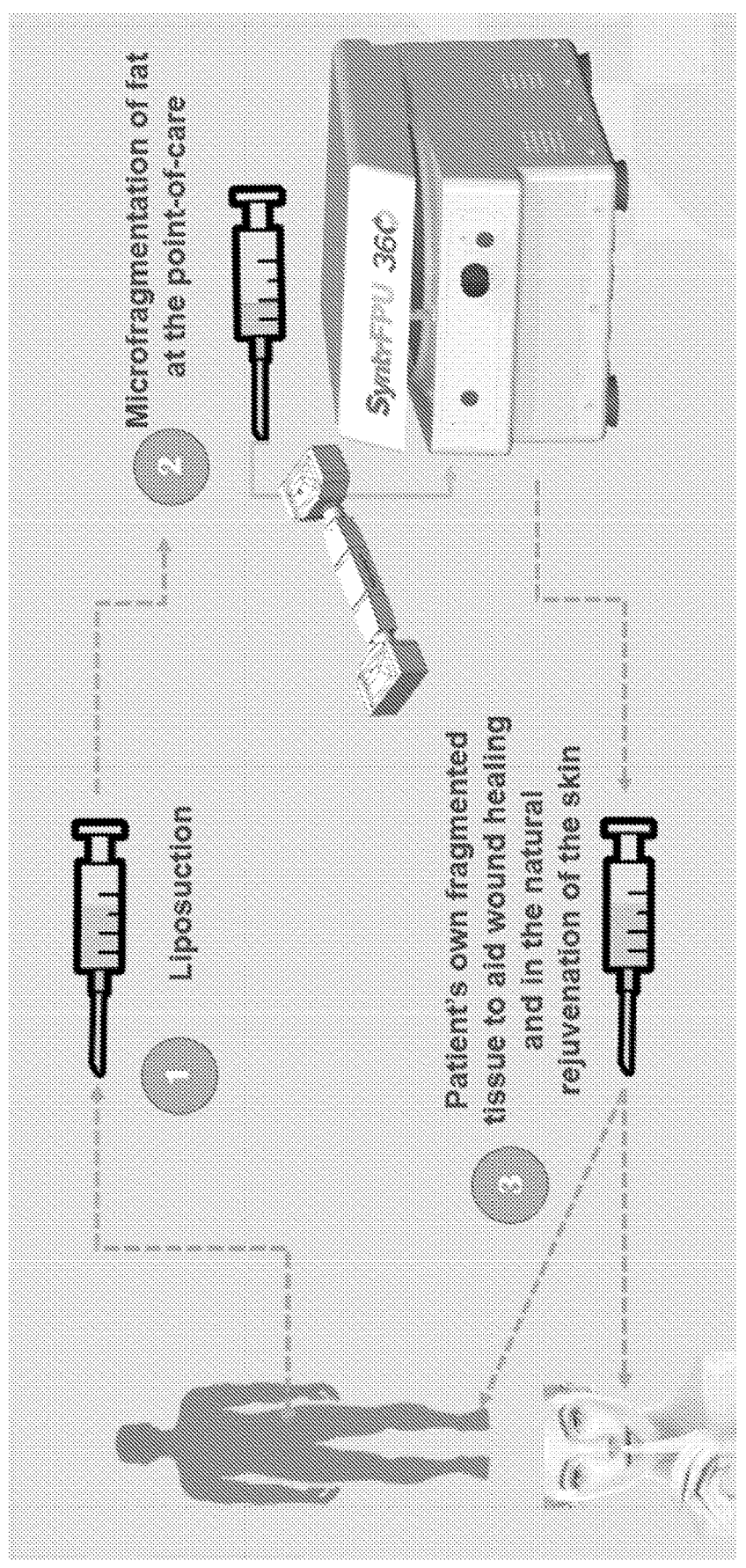
FIG. 29 depicts a schematic of one non-limiting embodiment of a treatment paradigm.

FIG. 29 provides a schematic of a non-limiting embodiment of a treatment paradigm. In this example, a subject in need of tissue repair or regeneration (e.g., having a wound) undergoes a lipoaspiration procedure (e.g., liposuction). The acquired adipose tissue is then processed according to embodiments disclosed herein and then reinjected into the site and/or periphery of the tissue that requires repair and/or regeneration.

Administration and Dosing

Further provided herein are methods of treating a subject having a wound (e.g., DFU), comprising administering to the subject a composition comprising ADSCs that have been mechanically processed as disclosed herein. For example, some embodiments of the compositions and methods described herein relate to use of mechanically processed ADSCs for treating a diabetic patient with a DFU. Uses of such processed ADSCs for treating DFUs are also provided. In certain embodiments, treatment of a subject with mechanically processed ADSCs described herein achieves one, two, three, four, or more of the following effects, including, for example: (i) reduction or amelioration the severity of disease or symptom associated therewith; (ii) reduction in the duration of a symptom associated with a disease; (iii) protection against the progression of a disease or symptom associated therewith; (iv) regression of a disease or symptom associated therewith; (v) protection against the development or onset of a symptom associated with a disease; (vi) protection against the recurrence of a symptom associated with a disease; (vii) reduction in the hospitalization of a subject; (viii) reduction in the hospitalization length; (ix) an increase in the survival of a subject with a disease; (x) a reduction in the number of symptoms associated with a disease; (xi) an enhancement, improvement, supplementation, complementation, or augmentation of the prophylactic or therapeutic effect(s) of another therapy. Each of these comparisons are versus, for example, a different therapy for a disease, which includes performing invasive procedures to treat deep and complex wound, such as a DFU.

Administration can be by a variety of routes, including, without limitation, intravenous, intra-arterial, subcutaneous, intramuscular, intrahepatic, intraperitoneal and/or local delivery to an affected tissue. Doses of mechanically processed ADSCs can be readily determined for a given subject based on their body mass, disease type and state, and desired aggressiveness of treatment, but range, depending on the embodiments, from about $10^5$ cells per g to about $10^{12}$ cells per g (e.g., $10^5$-$10^7$, $10^7$-$10^{10}$, $10^{10}$-$10^{12}$ and overlapping ranges therein). In one embodiment, a dose escalation regimen is used. In several embodiments, a range of ADSCs is administered, for example between about $1\times10^6$ cells/g to about $1\times10^8$ cells/g. Depending on the embodiment, various types of wounds can be treated. In several embodiments, a DFU is treated. Additional embodiments provided for herein include treatment or prevention of the following non-limiting examples of wounds including, but not limited to, venous stasis ulcers, arterial ulcers, and pressure ulcers (i.e., bed sores).

Doses of mechanically processed ADSCs can be readily determined for a given subject based on their body mass, disease type and state, and desired aggressiveness of treatment, but range, depending on the embodiments, from about $10^5$ cells per g to about $10^{12}$ cells per g (e.g., $10^5$-$10^7$, $10^7$-$10^{10}$, $10^{10}$-$10^{12}$ and overlapping ranges therein). In one embodiment, a dose escalation regimen is used. In several embodiments, a range of mechanically processed ADSCs is administered, for example between about $1\times10^6$ cells/g to about $1\times10^8$ cells/g. Depending on the embodiment, various types of wounds can be treated.

EXAMPLES

Example 1—Determination of the Optimal CD-LOC Processing Parameters

The main objective of this portion of the contemplated study is to determine the optimal fully automated lab-on-a-chip (CD-LOC) processing parameters that generate the largest portion of CD34-DPP4+/CD55+ and multilineage differentiating stress-enduring (Muse) cells with acceptable level of overall cell viability. This will be accomplished through a block-randomized experiment in which five adipose tissue samples (10 ml each) are collected from each of 15 diabetic patients. The Body Mass Index and anatomical location of fat harvest will be noted at the time of surgery. Adult, diabetic patients will be defined as those with a hemoglobin-A1c (HbA1c) greater than 6.5. Additionally, patients on any form of immunosuppressive therapy or with active systemic infection will be excluded from the study.

Based on the current design of the CD-LOC platform, the shear force will be modulated by adjusting the RPM of the processing device. The adipose tissue samples will be collected and stored at room temperature and processed within 24 hours. Each sample will be washed thoroughly with sterile PBS. The tissue samples per patient will be randomized and processed at five shear forces: 0 (baseline), 25, 50, 75, and 100 kilodynes/cm$^2$. A portion of each sample will be snap frozen in liquid nitrogen and stored at −80° C. for subsequent immunohistochemistry.

All tissue samples will be digested using 0.1% collagenase at 37° C. for 30 minutes to isolate the stem cells from fat. This process will only be used for single cell isolation and subsequent analysis, but is not a component of device processing for clinical applications. Each resulting pellet will be strained via 100 µm strainer and subjected to RBC lysis buffed before final single-cell analysis. Automated cell count and viability will be determined using a dual-fluorescence cell counter (Luna-STEM, Logos Biosystems Inc., Annandale, VA). A phenotypic marker analysis will also be conducted by staining the tissue samples for CD45, CD34, and CD31 and analyzed via flow cytometry. Therefore, five processing parameters will be included to enable a delineation of the linear versus logarithmic nature of the induction relationship.

In order to test the cellular activity/efficacy, the cells will be plated in triplicate in 96-well plate in standard control media and water-soluble tetrazolium salt activity will be assessed per the manufacturer's protocol (Dojindo Molecular Technologies Inc, Rockville, MD). In order to tests the population doubling, cells will also be plated in triplicate at a density of $2\times10^4$/cm$^2$ in 6-well plates with control media and placed in standard culture conditions. Once the first set of cells approach 70-80% confluency, cells will be counted and assessed via the following equation:

$$\frac{duration * log2}{\log \text{ final concentration} - \log \text{ initial concentration}}.$$

A phenotypic marker analysis will be conducted by staining the cells with the following combination markers: MSCs: CD13-APCVio770/CD45-VioBlue/CD34-PerCP-Vio700/CD31-FITC/CD73-PE/CD146-APC; Muse cells: CD13-APC-Vio770/CD45-VioBlue/CD34-PerCP-Vio700/CD31-FITC/SSEA-3-PE; DPP4+/CD55+: CD45-VioBlue/CD34-PerCP-Vio700/CD31-FITC/CD55-APC, DPP4-APC; Apoptosis detection (Annexin-V-FITC kit). All samples will undergo a transcriptional analysis and will be processed with TRIzol reagent (Thermo Fisher Scientific) for RNA extraction, reverse transcribed followed by qRT-PCR analysis (Applied Biosystems Real-Time PCR 7300 system, TaqMan gene expression assays: angiogenesis, cell proliferation, wound healing, senescene, tumorigenesis, cell survival). The primary targets include: DPP4, CD55, HIF-1α, IL-6, TNF-α, PPARγ, HGF, VEGF, CXCL2, SCUBE3, DLL1, NR4A2, ADAMTS9, AK5, SOX2, RPA1, SGK1, HGF, IGF-1, SDF-I, PDGF-B, NGF-b, SCF, bFGF, POU5F1, REX1.

The samples will also undergo a secretome analysis. Each sample will be plated ($2\times10^6$ cells) in T75 culture flasks in serum-free media (StemPRO MSC media, ThermoFisher Scientifc) and place in standard culture conditions until confluency is reached. The cultured media (CM) will be collected, centrifuged and stored for subsequent assays. Conditioned media will be thawed and filtered using a 0.22 µm filter. Enzyme-linked immunosorbent assay (ELISA) kits will be purchased (R&D Systems, Minneapolis, MN or Signosis, Inc., Santa Clara, CA) and the media will be assayed for the following cytokines per the manufacturer's protocol 1 (VEGF, HGF, IGF-1, SDF-1, PDGF-BB, NGF-β. SCF, bFGF. TNF-α). The absorbance will be spectrophotometrically measured at 450 nm using an infinite microplate reader.

The paracrine activity of the cells will be tested through the use of a cell migration assay and a scratch assay. For the cell migration assay, Boyden chambers (Neuroprobe Inc., Gaithersburg, MD) will be used. The Boyden chambers will be equipped with 8-µm pore diameter polycarbonate filters (Nucleopore, Whatman Incorporated, Clifton, NJ) coated with 5 µg/mL of gelatin solution will be loaded with keratinocytes, fibroblasts of ADSCs at a concentration of $1\times10^5$ cells in migration media. The lower compartment of the chamber will be loaded with ADSC conditioned media and the plates will be placed in standard culture conditions. After 16 hours, filters will be removed from the chamber, fixed in 4% paraformaldehyde/PBS, stained with 0.5% crystal violate and counted under microscopy for migration.

For the scratch essay, keratinocyte and fibroblast monolayers will be plated in 6-well plates with control media and placed in standard culture conditions. Once confluent, the center of each well will be scratched with a P-200 tip to create a uniform cell-free zone. Cellular debris will be removed with a PBS wash step and the wells will be treated with CM from the control and experimental groups, as well as serum starved media to serve as a negative control. The cultures will be photographed at sequential time points to assess migration.

Preliminary data were obtained using the methods and experiments detailed above, with additional data forthcoming. The preliminary data demonstrates that 'microfat' processing (75 kilodynes/cm$^2$) leads to a 4-fold decrease in nucleated cell count per mg/tissue when compared to unprocessed tissue. Moreover, no significant decrease in the viability of those cells were observed. Additionally, the preliminary data demonstrates that automated processing of 'microfat' at increasing shear-stress leads to a correlative stem cell phenotype in a logarithmic fashion and a linear relationship when manually processed. Lastly, based on pilot data, the cell viability is optimally 90% at a shear force of 75 kilodynes/cm$^2$ and decreased to 50% at the shear force of 100 kilodynes/cm$^2$. These results show that the shear force involved in microfat processing leads to a significant upregulation in regeneration phenotypes. Further processing under various parameters can also render the fat tissue into nanofat.

Statistical Method

A linear mixed effects regression will be performed in which the unit of analysis is a tissue sample from a patient. The outcome variable is the proportion of CD34+ cells. The fixed effect includes shear force. The random effects are the tissue samples from the same patient. Based on this mixed effects model, the mean proportions of CD34+ cells at each processing rate will be computed while accounting for intra-patient and inter-patient heterogeneity.

Sample Size and Power Analysis

Based on pilot data, the cell viability is optimally 90% at a shear force of 75 kilodynes/cm2 and decreased to 50% at the shear force of 100 kilodynes/cm2. Thus, it is hypothesized that as the shear force increases, the mean proportion of CD34+ cells will increase linearly and reach maximal level at a shear force of 75 kilodynes/cm2 with the cell viability greater than 75%. With 15 diabetic patients and five tissue samples per patient a 82% power will be achieved to test this hypothesis based on a two-sided paired t-test at 5% significance level. Secondarily, it is anticipated that subpopulations of MSCs, Muse and Diabetic wound healing cells will mirror the activity of CD34. Additionally, it is expected that a non-tumorigenic transcriptional pattern similar to that observed with a previous adipose derived Muse cell populations will be observed.

Example 2—Characterization of Microfragmented Adipose Tissue

Experiments for characterizing the resultant adipose tissue that results from processing according to methods and using systems disclosed herein were undertaken. Adipose tissue was processed according to the non-limiting approach disclosed in Example 1. Adipose tissue was collected from both healthy and diabetic donors, in order to determine if diabetic adipose tissue behaved similarly to that of healthy subjects, since, in several embodiments, the ultimate treatment paradigm is an autologous approach (see, e.g., FIG. 29).

Figures 30A, 30B:
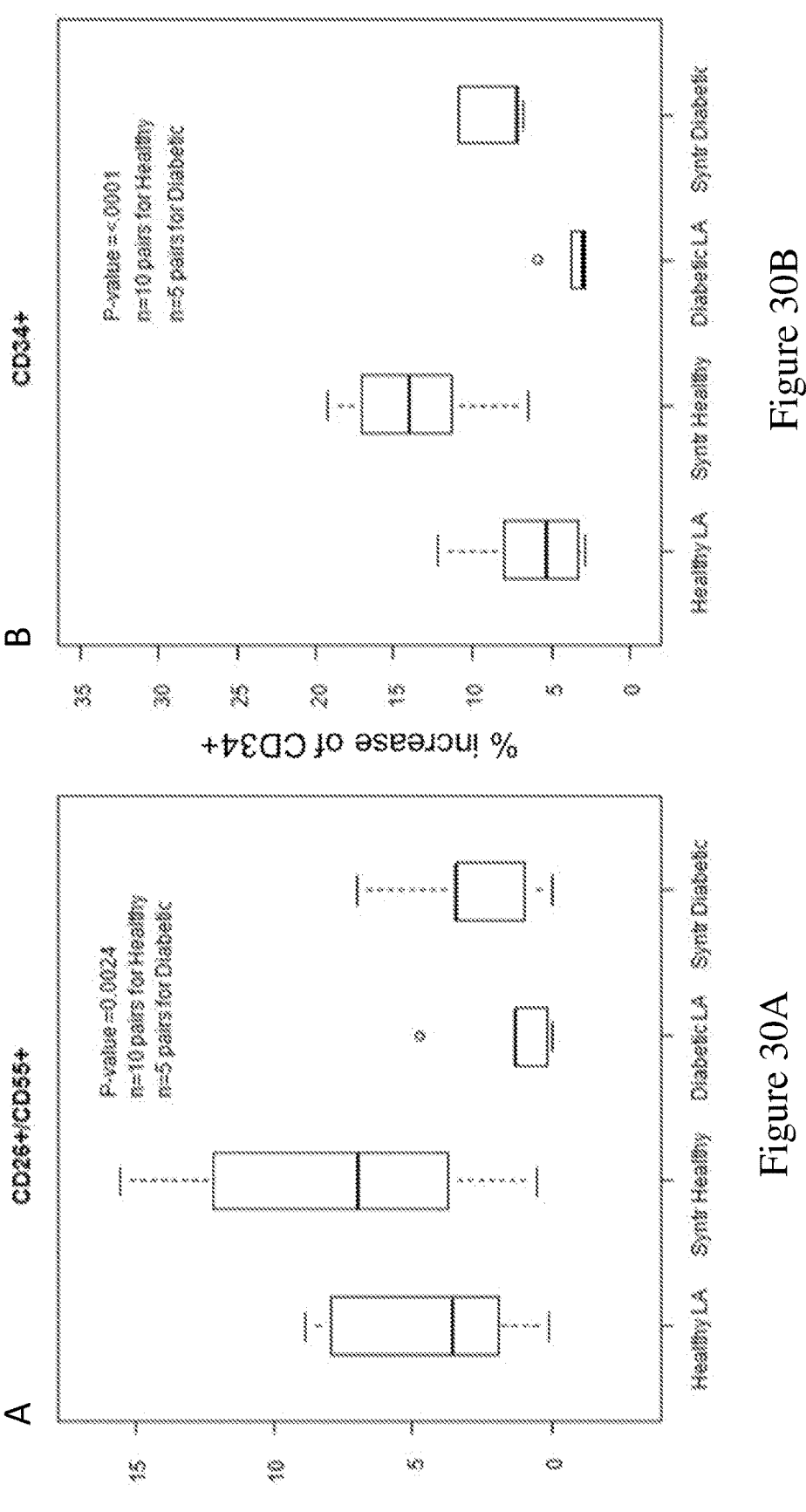
FIGS. 30A-30B relate to phenotypic data of cells derived from adipose tissue using the systems and methods disclosed herein.

The cellular profile of the resultant microfragmented adipose tissue was assessed by determining the change in the CD26+/CD55+ cell component of the processed tissue. A CD26+/CD55 positive phenotype is indicative of an adipose-derived stem cell subtype, which is thought to enhance the ability of the resultant cells to contribute to tissue repair and/or regeneration. FIG. 30A shows that the processing of adipose tissue using the systems and methods disclosed herein result in an increase in the percentage of CD26+ CD55+ cells in the processed adipose tissue ("Syntr" labels) as compared to unprocessed tissue. Moreover, this holds true whether the tissue being processed is from a healthy or a diabetic subject. Thus, regardless of whether the donor adipose tissue is from a healthy, or a diabetic subject, processing the adipose tissue according to methods disclosed herein and using the systems disclosed herein, a higher percentage of the resultant population within the adipose tissue bears a regenerative phenotype. Also shown, in FIG. 30B, is a similar phenomenon for detection of CD34+ cells (e.g., stem cells).

Figures 31A, 31B:
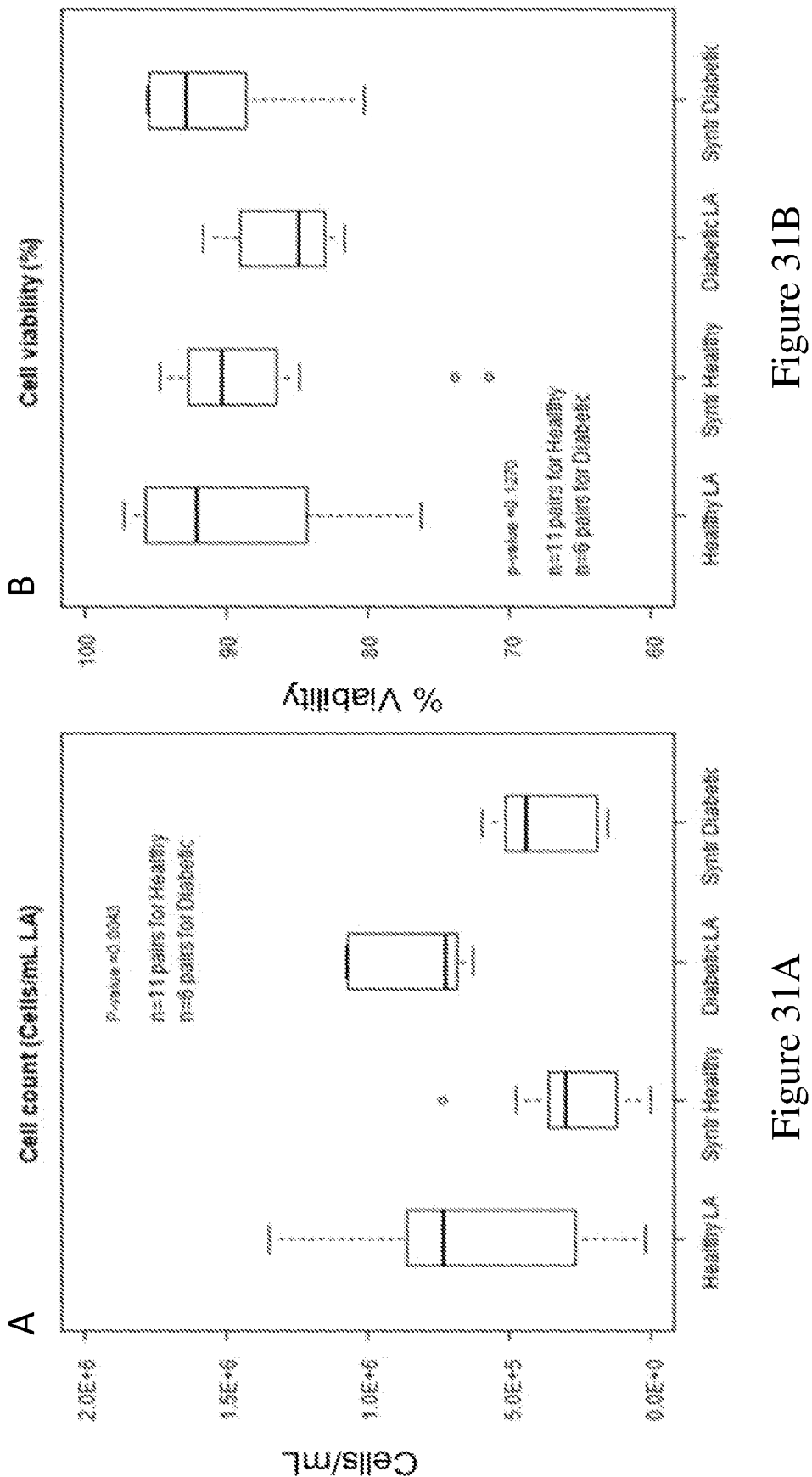
FIGS. 31A-31B relate to cell count and viability data regarding cells derived from adipose samples using the systems and methods disclosed herein.

An assessment of the cell density and the viability of cells within processed adipose tissue was also conducted. These data are shown in FIGS. 31A and 31B. As can be seen in FIG. 31 a, the processing of adipose tissue does result in a significant reduction in the number of cells per milliliter of adipose tissue (whether considering either healthy or diabetic adipose samples). FIG. 31B demonstrates that the viability of cells within the adipose tissue post-processing (e.g., those cells that survived the processing procedure) is maintained at a level that is not statistically significantly different from unprocessed tissue. Taken in conjunction with the data from FIG. 30, processing adipose tissue as disclosed herein does reduce the cell density within the post processed tissue, however the remaining cells are not only equally as viable as those in unprocessed tissue, the resultant cell population is enriched for those cells having a phenotype associated with stem cells, suggesting an enhanced ability of the post-processed adipose tissue to induce, hasten, or otherwise facilitate tissue repair and or regeneration.

Figures 32A, 32B:
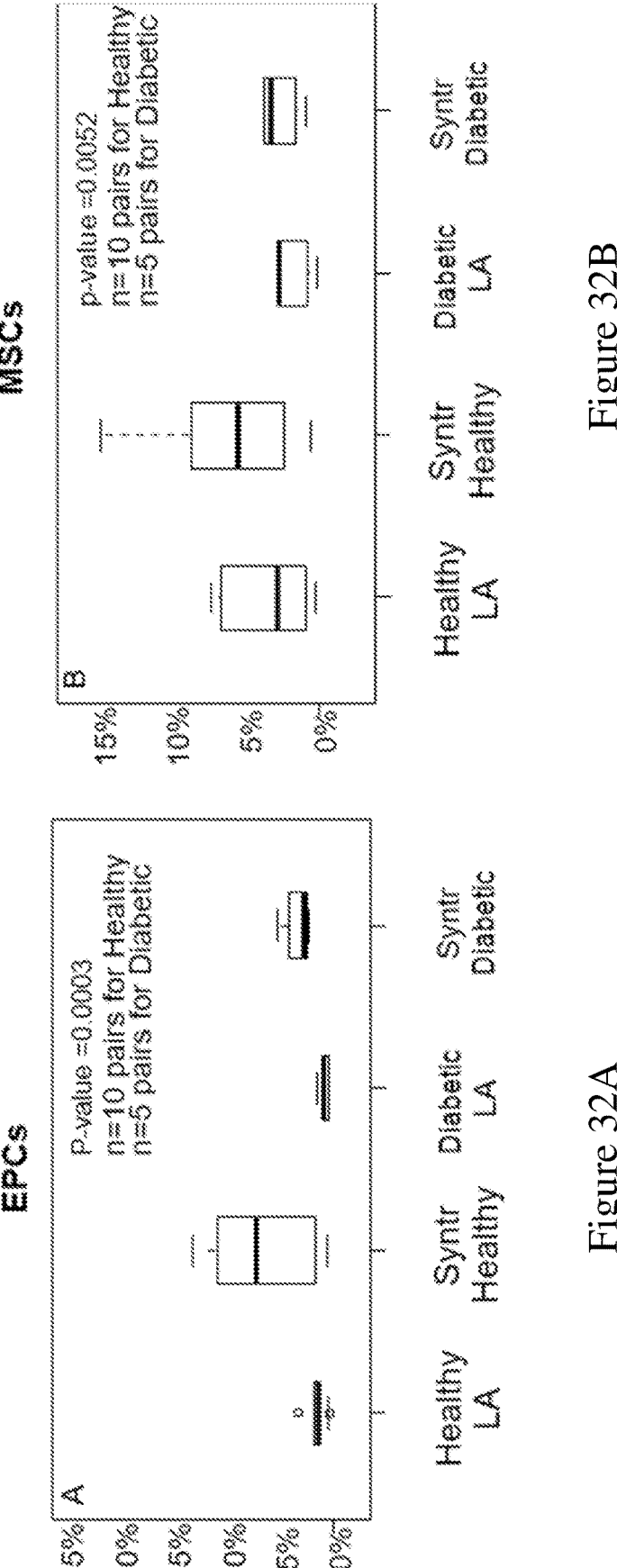
FIGS. 32A-32C relate to the type of cells present after processing adipose samples using the systems and methods disclosed herein.
Figure 32C:
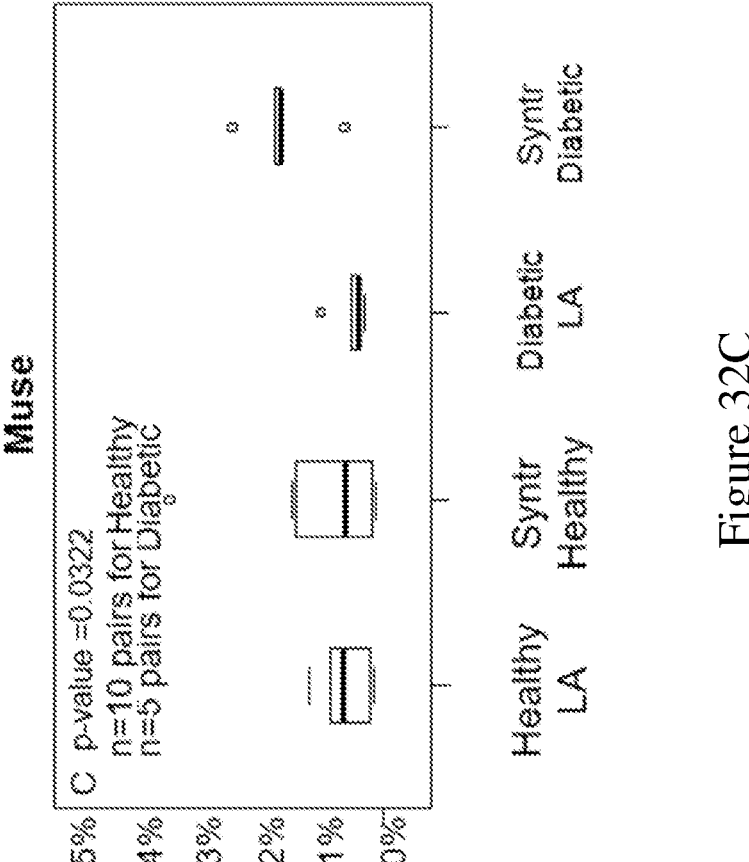

Furthering this concept of an enriched cell population for facilitating tissue repair and or regeneration, when looking at the type of cells present in tissue post processing those that are categorized as various types of stem cells are increased in the relative proportion of the population after processing. For example, FIG. 32A shows a significant increase, whether using healthy or diabetic adipose tissue, in the percentage of endothelial progenitor cells (EPC) in the processed tissue. Likewise, a significant increase in the relative proportion of mesenchymal stem cells (MSC) after processing is shown in FIG. 32B. Finally, FIG. 32C shows an increase in the percentage of pro-regenerative Muse cells after adipose tissue processing.

Figure 33A:
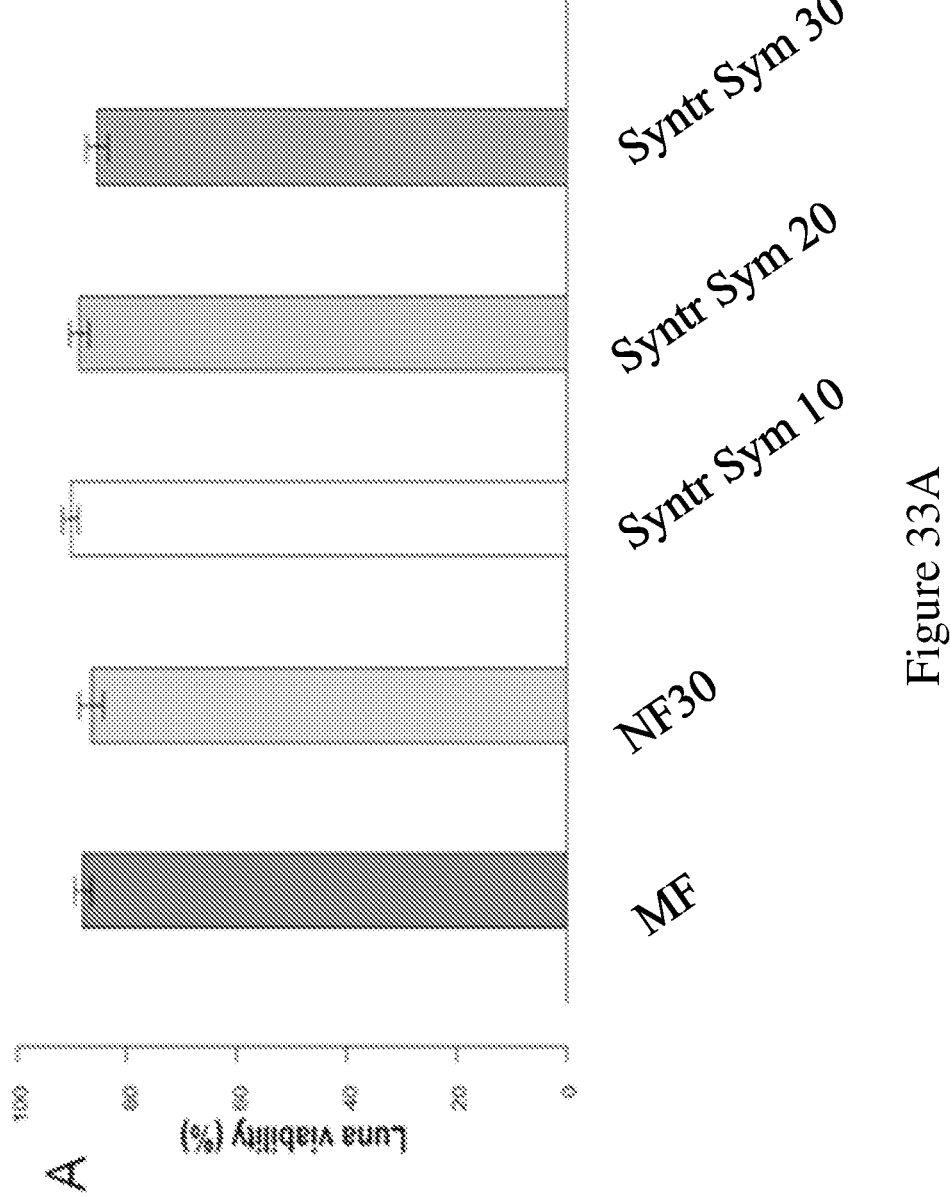
FIGS. 33A-33C relate to characteristics of cells and cell types after processing adipose samples using the systems and methods disclosed herein.
Figure 33B:
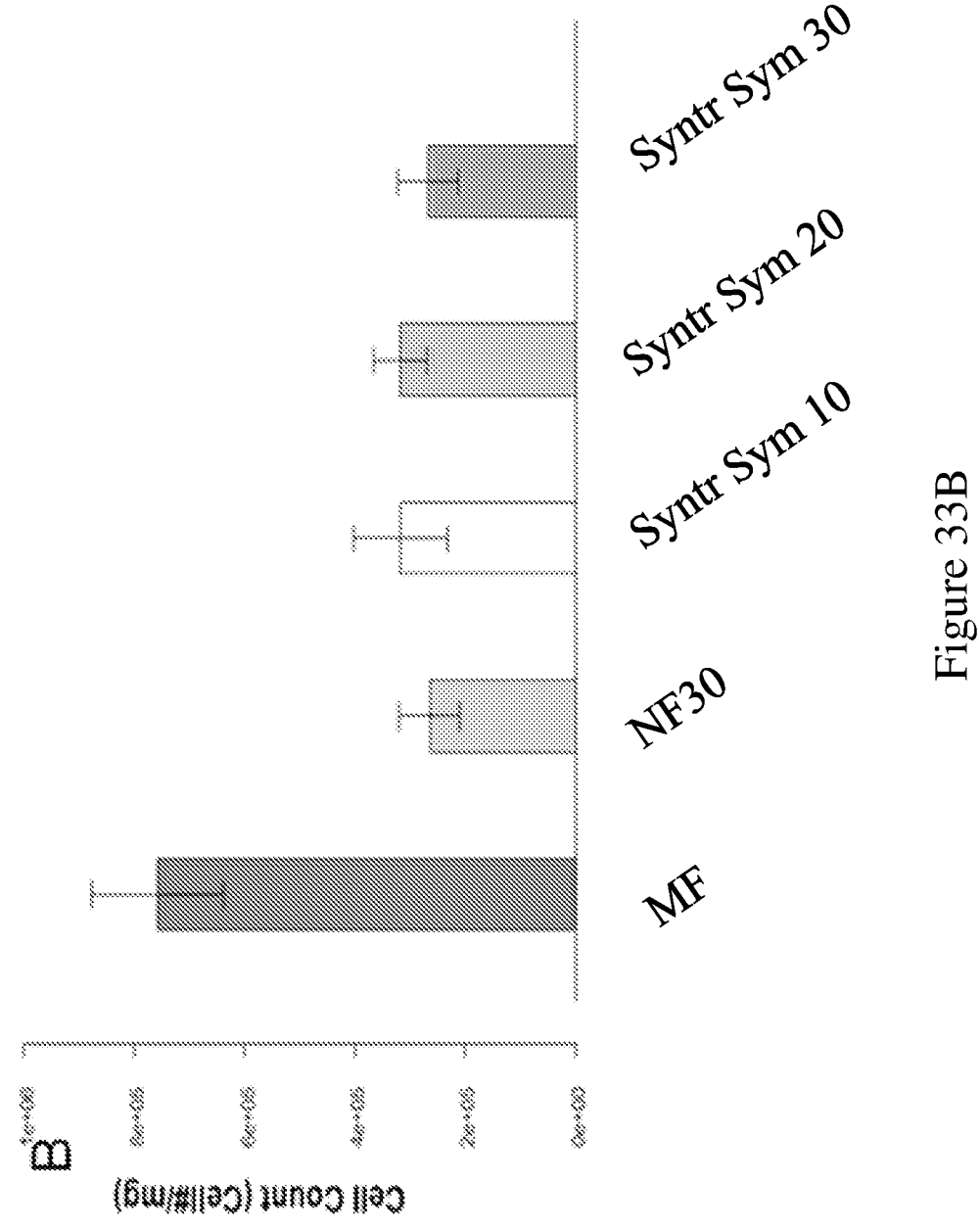
Figure 33C:
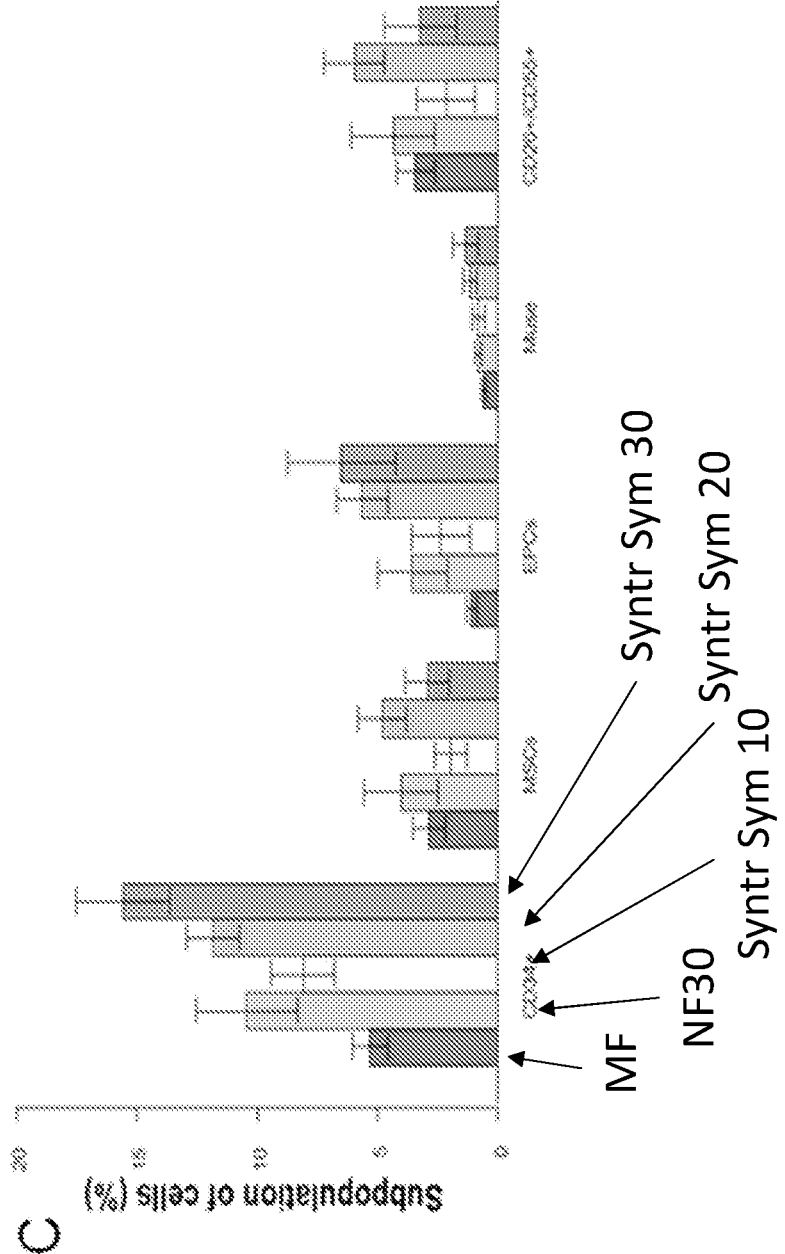

Similar data reflecting this overall trend of reduction in cell number coupled with relative enrichment of regenerative cell phenotypes is shown in FIGS. 33A through 33C. Additionally, these Figures compare different adipose processing approaches. Macro fat (MF) is indicative of unprocessed adipose tissue. Nano fat (NF30) is manually processed adipose tissue that is passed between two syringes 30 times. Each of the remaining data points are adipose tissue that is processed using the systems disclosed herein for either 10, 20, or 30 repetitions. As can be seen in FIG. 33A, processing of fat tissue does not inherently alter the overall viability of the resultant cell types that survive the processing procedure. FIG. 33B shows that mechanical processing of adipose tissue does result in an overall lower cell count. Notably, whether 10, 20, or 30 repetitions of the adipose tissue processing methods disclosed herein are used, the resultant cell count remains stable. FIG. 33C presents additional data that relates to the particular subtype of population of cells within adipose tissue for each of the histograms. The groups are presented in the same order, moving from left to right MF, NF 30, Syntr 10 repetitions, Syntr 20 repetitions, and Syntr 30 repetitions. The leftmost histogram in FIG. 33C shows the relative percentage of CD34+ cells within the tissue sample. As can be seen, any of the processing approaches undertaken result in a relative increase in the percentage of CD34+ cells within the post-processed tissue. Notably, with an increase in the number of processing runs, adipose processing performed according to embodiments disclosed herein and using the systems disclosed herein advantageously result in a processing run-dependent increase in the percentage of CD34+ stem cells within the processed tissue. Generally similar results can be seen not only with the percentage of EPCs but also muse cells, the 3rd and 4th histogram presented respectively. Mesenchymal stem cells, shown in the second histogram presented do not show this processing run dependent increase. However, it is notable that enrichment occurs to at least the same degree, if not more than the NF30 syringe based processing. Similar results are also seen for the CD26+/CD55+ positive cell subtype. Taken together, these data show that adipose tissue processing enriches the processed tissue with cells that show a pro-regenerative phenotype and show no reduction in viability, suggesting that adipose tissue that is processed in the manners disclosed herein, and using the systems disclosed herein, will induce or enhance tissue repair and/or regeneration. In several embodiments, the tissue repair is enhanced as compared to adipose tissue processed in other ways.

Example 3—Processed Adipose Tissue Role in Promoting Wound Healing

The present non-limiting Example was performed to compare the effects of standard non-processed diabetic stromal vascular fraction (SVF) and microfragmented diabetic adipose tissue (SA) which has a higher level of cell activity in promoting wound healing in diabetic mice. Two adipose tissue samples (10 ml each) were collected from each of 20 diabetic patients. Collection methods, parameters, and criteria were those used in non-limiting Example 1 above. Forty 6-week old male db/db mice were acquired (The Jackson Laboratory., Sacramento, CA) and kept under controlled environmental conditions (constant laminar flow, temperature of 20-23° C., humidity of 40-60%, 12-hour light/12-hour dark cycle) in an animal resources facility. A block-randomized, pair-controlled, blinded experiment with two treatment groups was be conducted.

The mice were anesthetized intraperitoneally with 12 mg/kg xylazine (Vedco Inc., St. Joseph, MO) and 80 mg/kg ketamine (Ketathesia, Butler Scein Animal Health Supply, North Dublin, OH) and 6 mm full-thickness wounds were made through the panniculus *carnosus* layer on the dorsum of each mouse and splinted with silicone. The mice were observed for 48-72 hours prior to treatment. Bilateral wounds in each mouse were randomized to be injected with microfragmented activated diabetic fat tissue as resulting from the use of the systems and methods disclosed herein (see e.g., Example 1) or standard diabetic SVF on one side, and placebo saline in the other wound (paired control). For the experimental group, a total of $1 \times 10^5$ cells in 125 µl of saline was injected sub-dermally in four sites around the wound edge, with the control group receiving saline injections only. The wounds were covered with an occlusive dressing and digital photographs taken on days 0, 5, 9, 13, 17, 21 and 24 and the wound area was measured using digital photography. At the time point of the earliest wound closure, the wounds were excised, fixed and cryosectioned. Slides were stained with hematoxylin & eosin (H&E), Trichrome, Vimentin, and using an anti-CD31 antibody for basic tissue and vessel density analysis and imaged using fluorescence microscopy (Evos FL, Thermo Fisher Scientific). The study staff who conducted the experiment/measurements were blinded from the treatment randomization scheme.

Figure 34A:
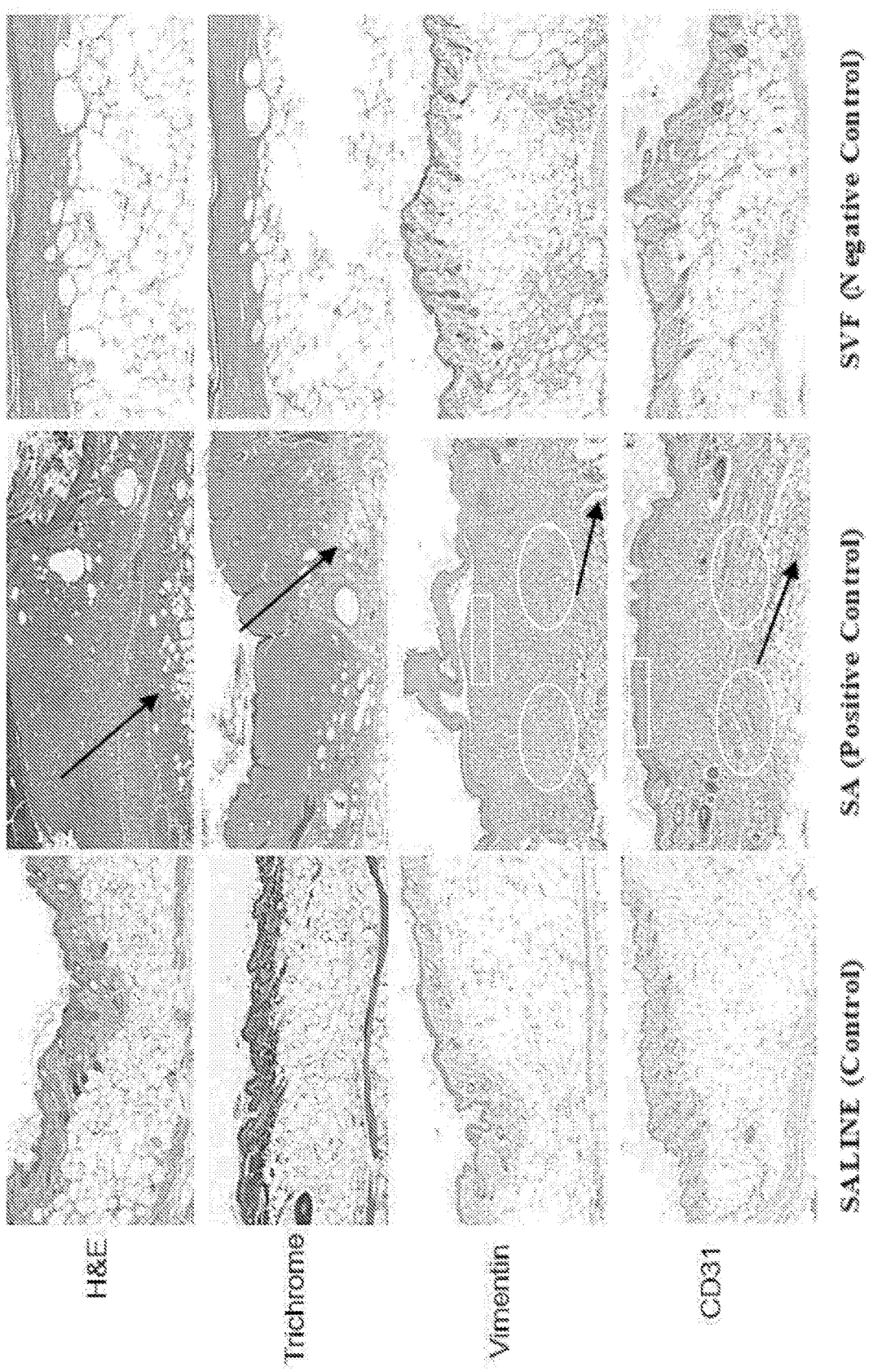
FIGS. 34A-34C show data related to wound healing using cells obtained by processing adipose samples using the systems and methods disclosed herein.
Figure 34B:
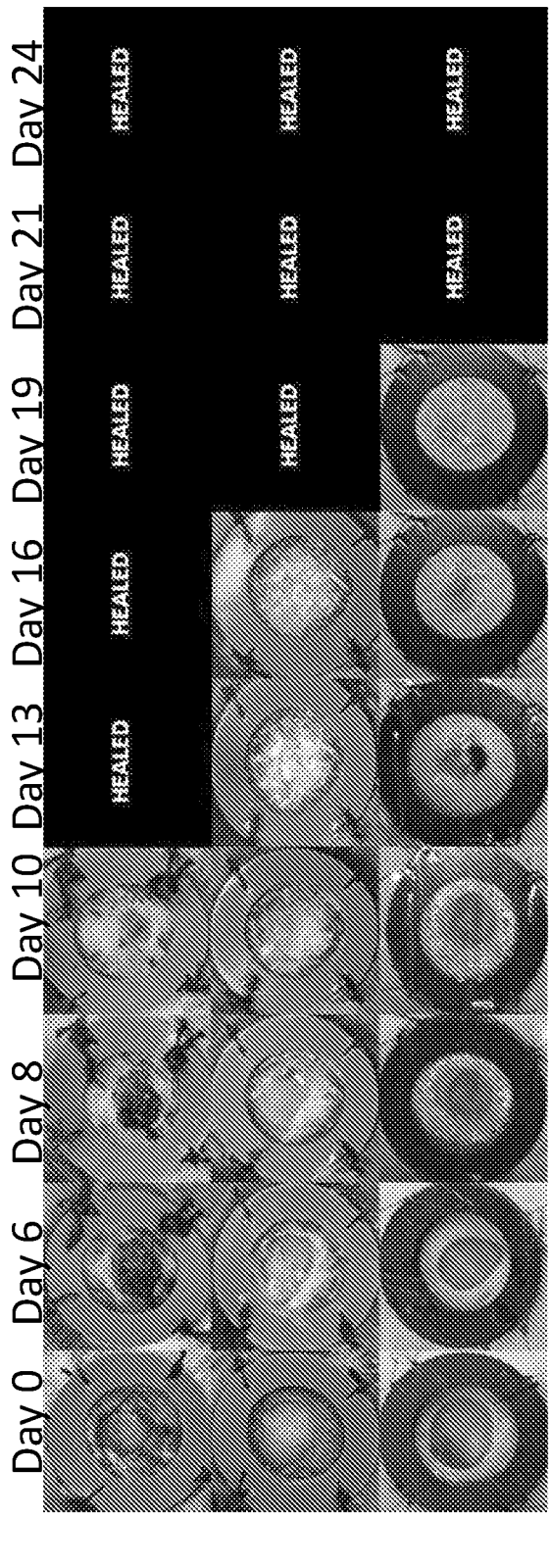
Figure 34C:
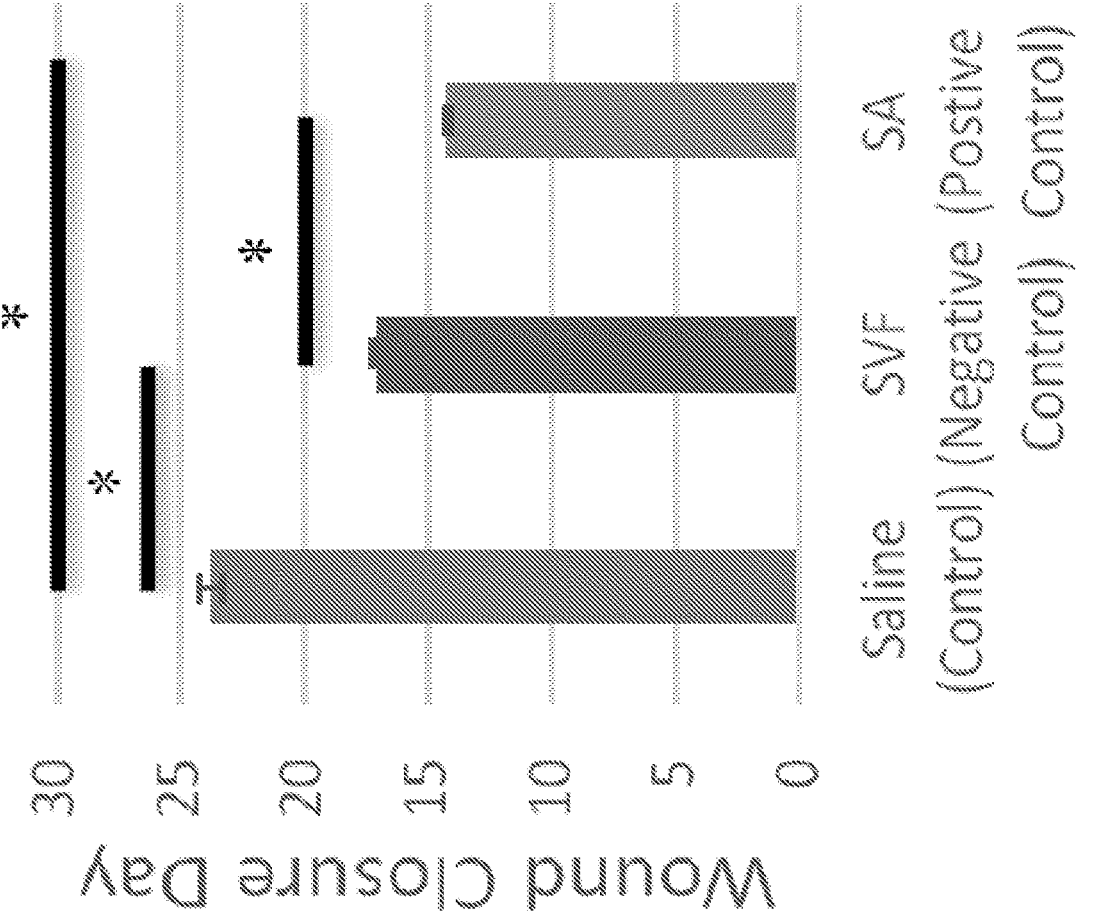

The data from this in vivo study are provided in FIGS. 34A through 34C. FIG. 34A shows the histology result from the wounds that were excised post-closure. The leftmost panel represents those wounds that were treated with saline, the central column represents those that were treated with adipose tissue processed according to embodiments disclosed herein, and the rightmost panel of figures relates to the negative control wounds, which received unprocessed SVF. The top row shows hematoxylin and eosin staining, the 2nd row shows Masson's trichrome staining, the 3rd row shows immunohistochemistry to detect vimentin, and the 4th row shows immunohistochemistry to detect CD31. In the central column, arrows point to the presence of adipose tissue that originates from the human processed adipose tissue. The presence of adipose derived stem cells are shown generally within the circles, while the rectangle generally shows areas of increased dermal regeneration. The enhanced degree of staining of vimentin using the SA adipose tissue is indicative of epithelial to mesenchymal transition, evidence of wound healing. Also, the increased expression of CD31 (also known as PECAM-1) indicates positive impacts on inflammatory responses and angiogenesis (notably, anti-PECAM-1 antibodies are known to block normal endothelial cell-cell contacts and influence cell migration, pointing to a role of PECAM-1 in angiogenesis and wound healing).

FIG. 34B shows the photographic evidence of treatment of the induced wound and the timeline for healing. As can be seen from these data, those wounds that were treated with Saline took longest duration of time to heal, 19 days to closure in the example shown in FIG. 34B. Similarly, those wounds treated with SVF took over 3 weeks to heal. In contrast, those wounds treated with adipose tissue processed as disclosed herein were healed in under 2 weeks. The photographic data is summarized in FIG. 34C. These data showed that as compared to either Saline or SVF administration, there was a statistically significant reduction in time to wound closure when adipose tissue processes disclosed herein was administered to the wound. (*p<0.0003 Saline vs. SVF; p<0.00003 saline vs. SA; p<0.001 SA vs. SVF via ANOVA or student's t-test. Error bars represent s.e.m). These data confirm that the methods, processes, and systems disclosed herein and used for the processing of adipose tissue results in a process tissue that has enhanced wound repair characteristics.

Although the embodiments of the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or sub-combinations of the specific features and aspects of the embodiments may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. For all of the embodiments described herein the steps of the methods need not be performed sequentially. Thus, it is intended that the scope of the present inventions herein disclosed should not be limited by the particular disclosed embodiments described above.

Statistical Method

A linear mixed effects regression analysis will be performed in which the unit of analysis is a wound of a mouse. The outcome variable is the percentage of healing area in the wound. The fix effects include the 2-category variable of treatment groups (activated diabetic SVF versus standard diabetic SVF) and an indicator for whether the wound is treated or placebo. The random effects include two wounds per mouse and two samples per patient. Based on this linear mixed effects model, the mean increases in percentages of healing area between the treated and placebo wound will be compared between the two treatment groups while accounting for patients and mice heterogeneity.

Sample Size and Power Analysis

With a total of 40 mice with bilateral wounds being treated with activated diabetic SVF or microfragmented diabetic fat tissue from fat samples collected from 20 diabetic patients (twp samples per patient), a 81% power will be achieved to test the hypothesis that the mean increase in % wound healing area is 95% among diabetic mice treated with microfragmented diabetic fat tissue as compared to 65% among diabetic mice treated standard diabetic SVF at day 14 after treatment receipt, based on a two-sided paired t-test with 5% significance level.

The present invention is not limited to the embodiments described above. Various changes and modifications can, of course, be made, without departing from the scope and spirit of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A system for processing biological samples comprising:
a support plate comprising:
    a central portion configured to reversibly interact with a motor for providing rotational force, and
    at least one lateral arm, wherein each of the at least one lateral arms includes a first opening and at least one securement opening;
at least one carriage assembly, wherein each of the at least one carriage assemblies is configured to reversibly interact with one of the at least one lateral arms, wherein each of the at least one carriage assemblies comprises:
    a base comprising:
        a top surface comprising at least one circular groove,
        a bottom surface comprising a post configured to extend through the first opening of one of the at least one lateral arms,
        a first arm, and a second arm;
    a spring platform comprising:
        at least one circular groove positioned on a bottom surface of the spring platform,
        a first engagement portion,
        a second engagement portion, and
        wherein the spring platform is positioned adjacent to the top surface of the base,
    at least one spring retained between the base and the spring platform, wherein the at least one spring is secured at a first end in the at least one circular groove of the base and at a top end in the at least one circular groove of the spring platform, wherein the at least one spring is configured to provide an upward force on the spring platform, and
    a securing element configured to secure a chip assembly on the at least one carriage assemblies; and
    wherein each of the at least one carriage assemblies is at least rotatable about 180 degrees.

2. The system of claim 1, wherein the spring platform is configured to move between a first position and a second position in response to the insertion or removal of the chip assembly.

3. The system of claim 2, wherein the spring platform further comprises a tab and the securing element further comprises a channel configured to receive the tab of the spring platform, and wherein the tab is configured to move within the channel of the securing element as the spring platform is configured to move between the first position and the second position.

4. The system of claim 1, wherein the securing element includes at least one guide rail configured to guide and position the chip assembly.

5. The system of claim 1, wherein the first engagement portion of the spring platform is configured to retain the first arm of the base, and wherein the second engagement portion of the spring platform is configured to retain the second arm of the base.

6. The system of claim 1, wherein the spring platform further comprises a platform configured to guide the chip assembly into the at least one carriage assemblies.

7. The system of claim 1, wherein the spring platform comprises a splash guard on the bottom surface of the spring platform, the splash guard configured to prevent fluid from being introduced to the at least one spring.

8. The system of claim 1, wherein the chip assembly comprises:
    a microfluidic chip comprising a fluid path that extends from a first end of the microfluidic chip to a second end of the microfluidic chip,
    a first sample chamber fluidly connected at a first end of the microfluidic chip, and chip,
    a second sample chamber fluidly connected at a second end of the microfluidic.

9. The system of claim 8, wherein the fluid path comprises at least one expansion region and a plurality of compression regions.

10. The system of claim 9, wherein the at least one expansion region increases in radius along a first, second, and third axis, wherein the first, second, and third axes are perpendicular to a central axis of the fluid path, and wherein at least one compression region of the plurality of compression regions has a diameter less than the diameter of the at least one expansion region, wherein the at least one compression region does not change in diameter.

11. The system of claim 10, wherein the first axis, the second axis, and the third axis are perpendicular to each other.

12. The system of claim 9, wherein the at least one expansion region increases in more than two dimensions.

13. The system of claim 8, wherein the fluid path comprises a plurality of tear drop expansion regions.

14. The system of claim 8, wherein the fluid path comprises a spherical or elliptical expansion region.

15. The system of any of claim 8, wherein the fluid path comprises a plurality of half tear drop expansion regions.

16. The system of claim 15, wherein the fluid path comprises at least one of a half spherical or half elliptical expansion region, a D-shaped expansion region, and an hour-glass.

17. The system of claim 8, wherein the fluid path comprises at least two expansion regions and at least one compression region positioned between the at least two expansion regions.

18. The system of claim 8, wherein the fluid path comprises at least three expansion regions and at least two compression regions positioned between the at least three expansion regions, wherein each of the at least two compression regions is positioned between adjacent expansion regions.

19. The system of claim 8, wherein a filter is positioned between the microfluidic chip and the first sample chamber or the microfluidic chip and the second sample chamber.

20. The system of claim 8, wherein the microfluidic chip comprises a luer lock on the first end of the microfluidic chip and on the second end of the microfluidic chip.

\* \* \* \* \*